United States Patent
Zhang et al.

(10) Patent No.: US 11,104,936 B2
(45) Date of Patent: Aug. 31, 2021

(54) COMPETITIVE COMPOSITIONS OF NUCLEIC ACID MOLECULES FOR ENRICHMENT OF RARE-ALLELE-BEARING SPECIES

(71) Applicant: WILLIAM MARSH RICE UNIVERSITY, Houston, TX (US)

(72) Inventors: David Yu Zhang, Houston, TX (US); Juexiao Wang, Houston, TX (US)

(73) Assignee: William Marsh Rice University, Houston, TX (US)

(*) Notice: Subject to any disclaimer, the term of this patent is extended or adjusted under 35 U.S.C. 154(b) by 737 days.

(21) Appl. No.: 15/295,170

(22) Filed: Oct. 17, 2016

(65) Prior Publication Data
US 2017/0029875 A1 Feb. 2, 2017

Related U.S. Application Data

(63) Continuation of application No. PCT/US2015/026330, filed on Apr. 17, 2015.

(60) Provisional application No. 61/981,588, filed on Apr. 18, 2014.

(51) Int. Cl.
*C07H 21/04* (2006.01)
*C12Q 1/6827* (2018.01)
*C12Q 1/6806* (2018.01)

(52) U.S. Cl.
CPC ......... *C12Q 1/6827* (2013.01); *C12Q 1/6806* (2013.01)

(58) Field of Classification Search
None
See application file for complete search history.

(56) References Cited

U.S. PATENT DOCUMENTS

| 6,444,661 | B1* | 9/2002 | Barton | C07F 15/008 |
| | | | | 514/185 |
| 2009/0011943 | A1* | 1/2009 | Drmanac | C12N 15/64 |
| | | | | 506/4 |
| 2011/0030675 | A1 | 12/2011 | Zhang et al. | |
| 2011/0306758 | A1 | 12/2011 | Zhang et al. | |
| 2013/0007183 | A1 | 3/2013 | Seelig et al. | |
| 2013/0071839 | A1 | 3/2013 | Seelig et al. | |
| 2013/0027413 | A1 | 10/2013 | Zhang et al. | |
| 2013/0274135 | A1 | 10/2013 | Zhang et al. | |
| 2019/0002971 | A1* | 1/2019 | Koslover | G01N 33/48 |

FOREIGN PATENT DOCUMENTS

CN 103328654 A 9/2013

OTHER PUBLICATIONS

"Oligonucleotide definition," Merriam-Webster.com; accessed Aug. 23, 2017).*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"Archaea," Wikipedia.com (accessed May 11, 2016).*
"Algae," Wikipedia.com (accessed Mar. 4, 2016).*
"Protozoa," Wikipedia.com (accessed May 11, 2016).*
"List of sequenced bacterial genomes" (Wikipedia.com; accessed Jan. 24, 2014).*
"Oligonucleotide definition," Merriam-Webster.com; accessed Aug. 23, 2017. (Year: 2017).*
"Oligonucleotide", Wikipedia.com, accessed Feb. 17, 2019. (Year: 2019).*
"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Clegg et al. Fluorescence resonance energy transfer analysis of the structure of the four-way DNA junction. Biochemistry May 26, 1992 vol. 31 No. 20 pp. 4846-4856. Especially p. 4847 fig 18.
Wang et al. Simulation-guided DNA probe design for consistently ultraspecific hybridization. Nature Chemistry ePub May 25, 2015 vol. 7 No. 7 pp. 545-553. Especially entire article.
Chinese Search Report issued in Chinese Application No. 201580032965.1 dated Apr. 3, 2019.

* cited by examiner

Primary Examiner — Bradley L. Sisson
(74) Attorney, Agent, or Firm — Parker Highlander PLLC

(57) ABSTRACT

The present disclosure describes the thermodynamic design and concentrations necessary to design probe compositions with desired optimal specificity that enable enrichment, detection, quantitation, purification, imaging, and amplification of rare-allele-bearing species of nucleic acids (prevalence <1%) in a large stoichiometric excess of a dominant-allele-bearing species (wildtype). Being an enzyme-free and homogeneous nucleic acid enrichment composition, this technology is broadly compatible with nearly all nucleic acid-based biotechnology, including plate reader and fluorimeter readout of nucleic acids, microarrays, PCR and other enzymatic amplification reactions, fluorescence barcoding, nanoparticle-based purification and quantitation, and in situ hybridization imaging technologies.

20 Claims, 18 Drawing Sheets
Specification includes a Sequence Listing.

FIG. 7
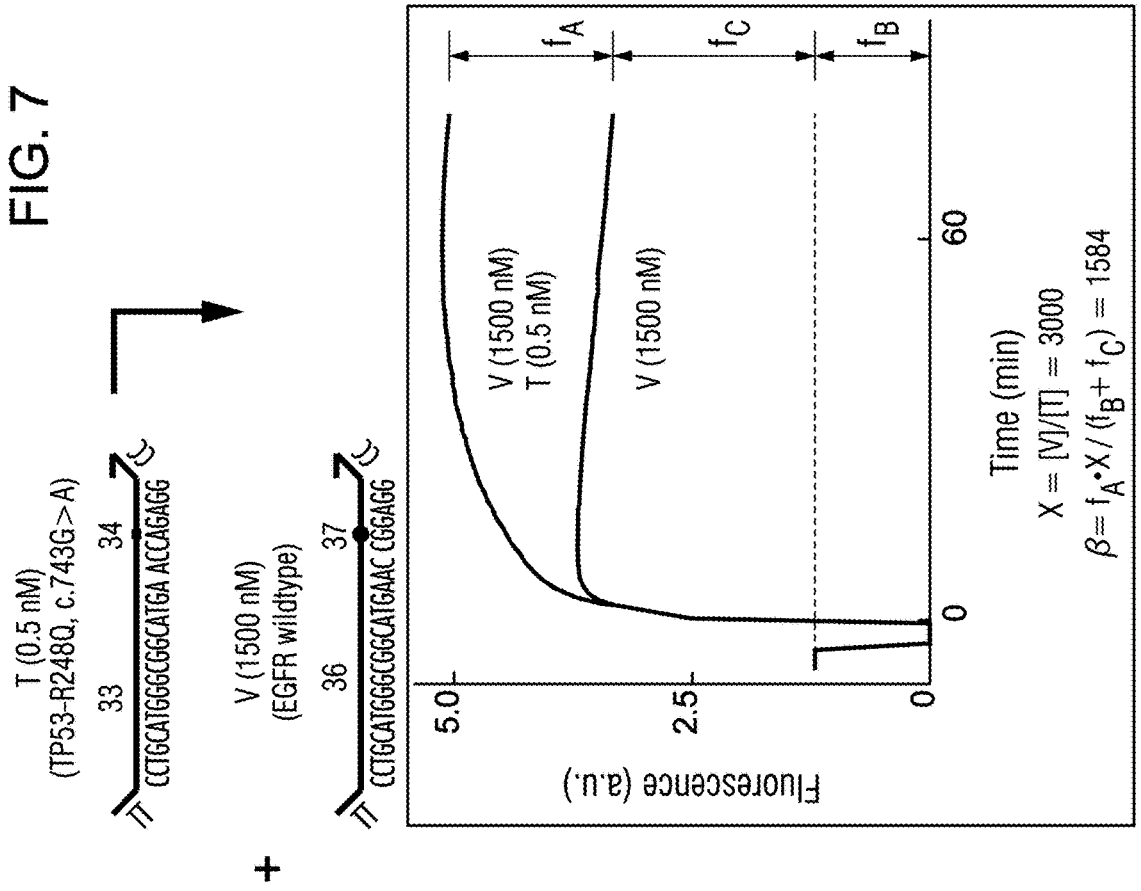
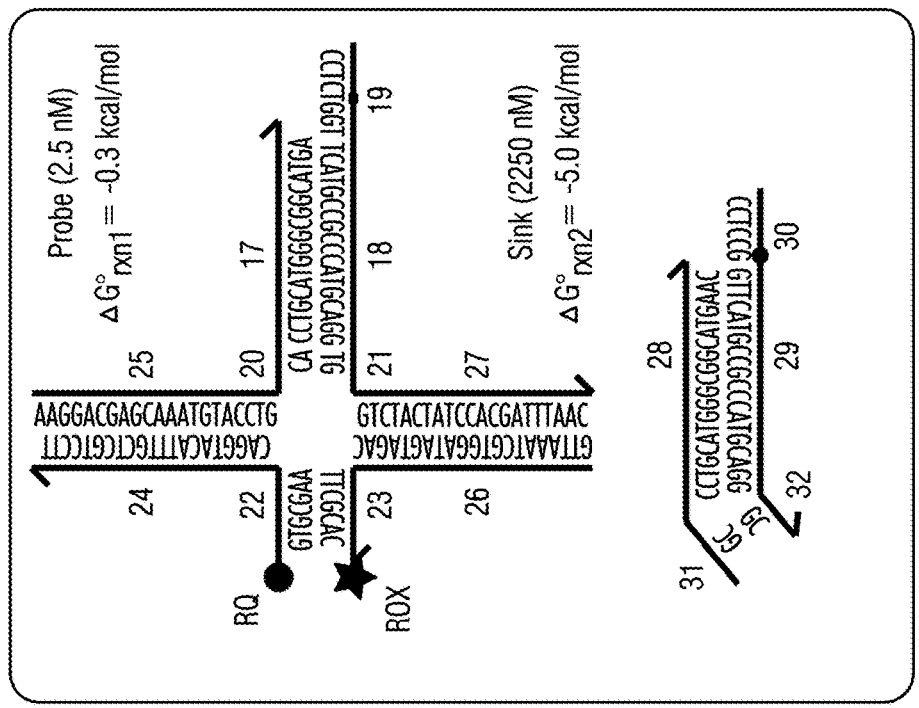

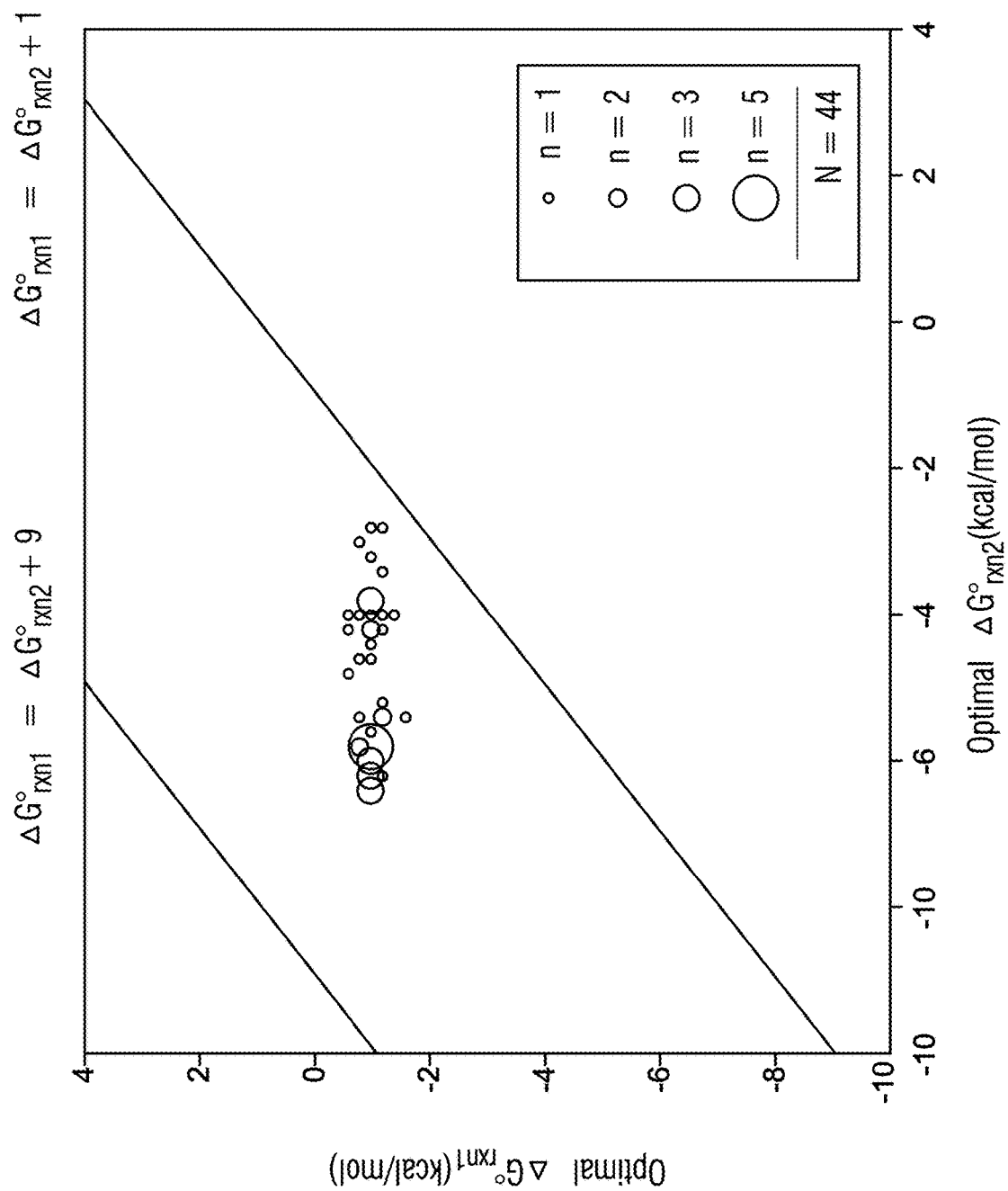

FIG. 10A
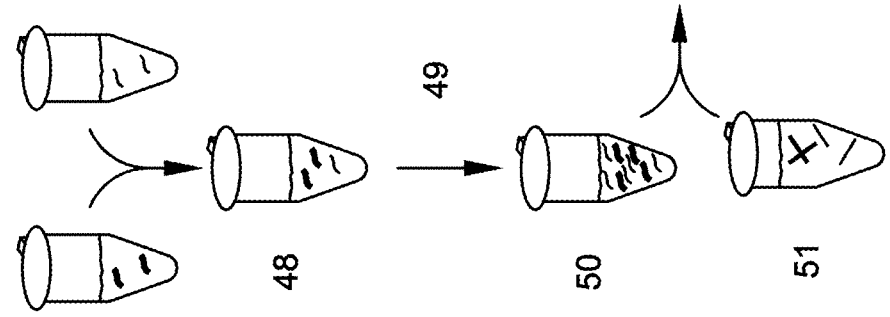
FIG. 10B
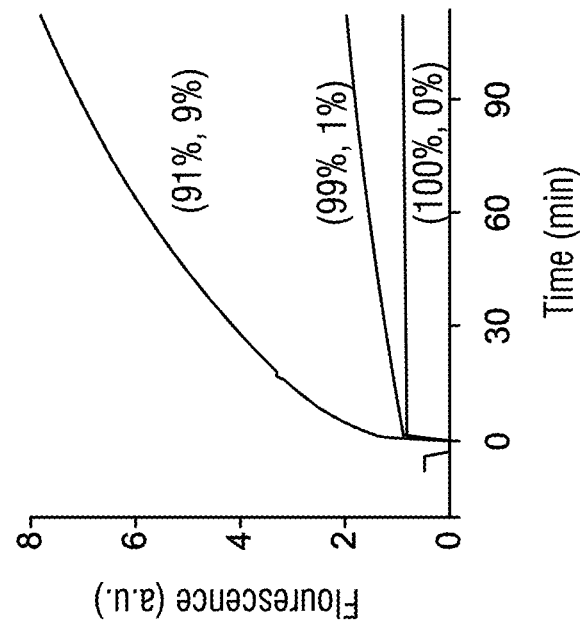
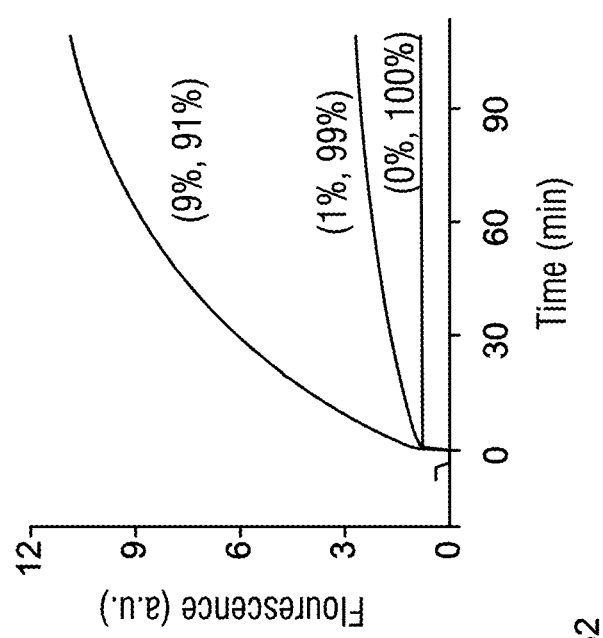

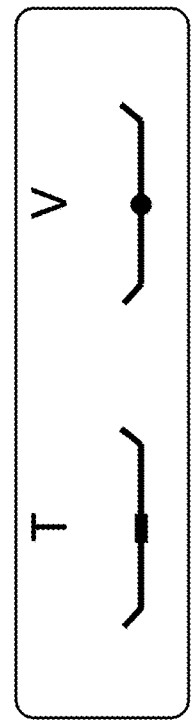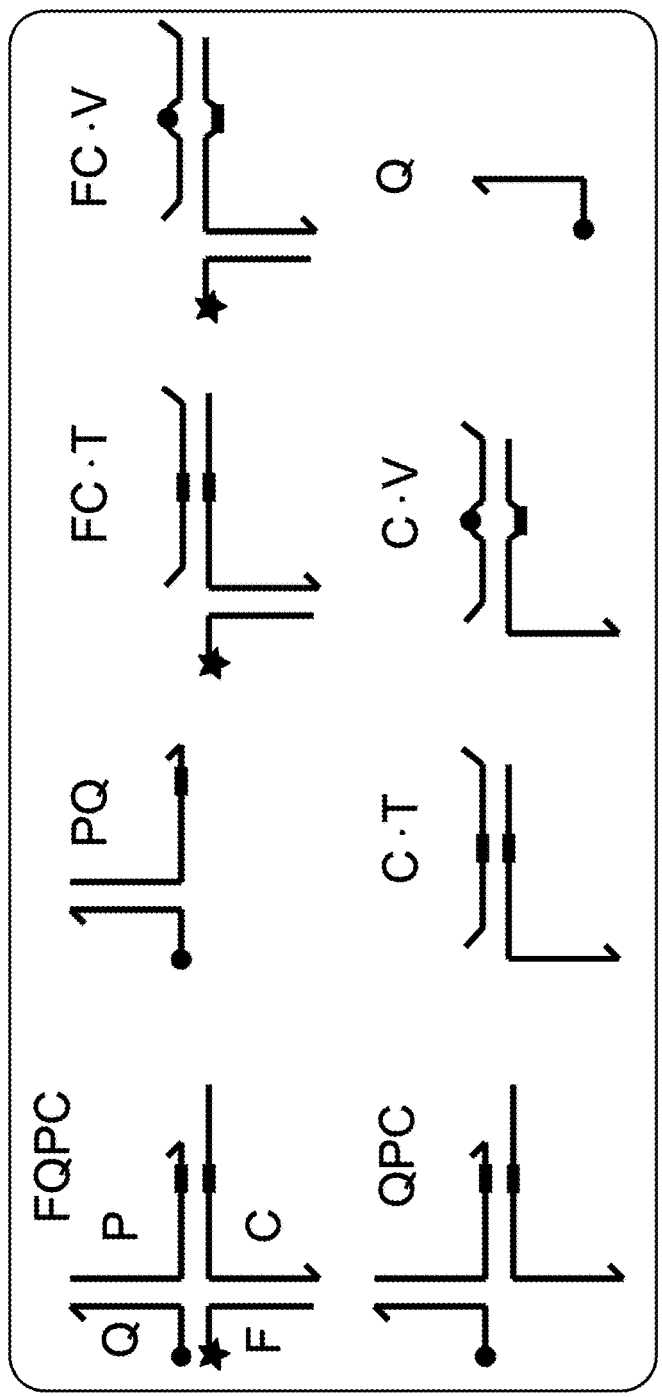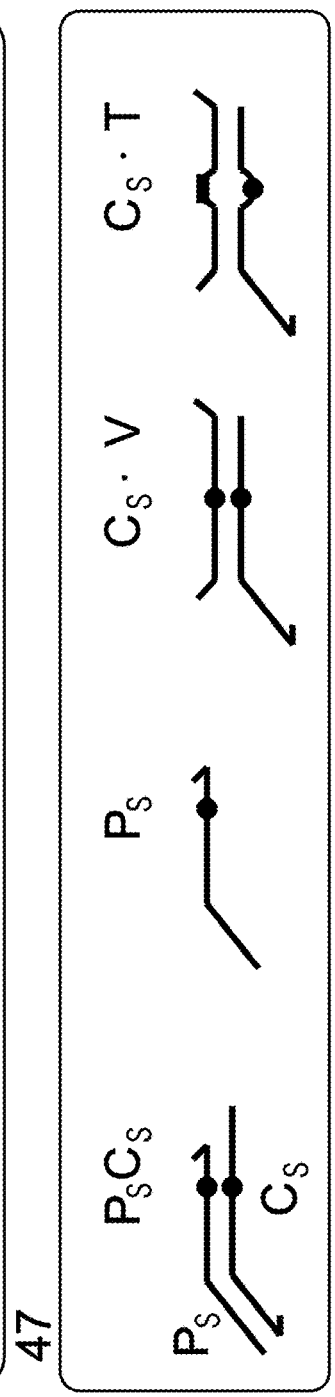
FIG. 11

SEQUENCE LISTING

<160> NUMBER OF SEQ ID NOS: 282

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gttaaatcgt ggatagtaga cttcgcac                                          28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgcgaacag gtacatttgc tcgtcctt                                          28

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccatgctcac agcctcatc                                                    19

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgtttcctga ggagtctgag g                                                 21

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaggacgagc aaatgtacct gcactcatcc aaaagaggaa a                           41

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggtcctgtt tcctcttttg gatgagtggt ctactatcca cgatttaac                   49

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgactctcat ccaaaagagg aa                                            22

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggtcctatt tcctcttttg gatgagagtc g                                  31

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aaggacgagc aaatgtacct gcactcatcc aaaagaggaa                         40

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggtcctatt tcctcttttg gatgagtggt ctactatcca cgatttaac               49

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acacactcat ccaaaagagg aaa                                           23

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggtcctgtt tcctcttttg gatgagtgtg t                                  31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ataggtggtt ttggtctagc tacagtgaaa                                       30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ataggtgatt ttggtctagc tacagtgaaa                                       30

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaggacgagc aaatgtacct gcaaggtggt tttggtctag c                          41

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttcactgtag ctagaccaaa accaccttgg tctactatcc acgatttaac                 50

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgttaataag gtgattttgg tctagc                                           26

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcactgtagc tagaccaaaa tcaccttatt aaca                                  34

```
<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ataggtgatt ttggtctagc tacagagaaa                                         30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ataggtgatt ttggtctagc tacagtgaaa                                         30

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaggacgagc aaatgtacct gcaaggtgat tttggtctag                              40

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctctgtagc tagaccaaaa tcaccttggt ctactatcca cgatttaac                    49

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgcaggtgat tttggtctag c                                                  21

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcactgtagc tagaccaaaa tcacctgcg                                          29

<210> SEQ ID NO 25
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttcaaaaaga tcaaagtgct ggcctccggt                                          30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttcaaaaaga tcaaagtgct gggctccggt                                          30

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaggacgagc aaatgtacct gcacaaaaag atcaaagtgc tgg                           43

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cggaggccag cactttgatc tttttgtggt ctactatcca cgatttaac                     49

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aggcaaaaag atcaaagtgc tgg                                                 23

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cggagcccag cactttgatc tttttgcct                                           29

<210> SEQ ID NO 31
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcctacgtga tggccatcgt ggacaacccc                                           30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcctacgtga tggccagcgt ggacaacccc                                           30

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaggacgagc aaatgtacct gcactacgtg atggccatcg t                              41

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggttgtccac gatggccatc acgtagtggt ctactatcca cgatttaac                      49

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agttctacgt gatggccagc gtg                                                  23

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggttgtccac gctggccatc acgtagaact                                           30

<210> SEQ ID NO 37
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 37
gtgcagctca tcatgcagct catgcccttc                                          30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtgcagctca tcacgcagct catgcccttc                                          30

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaggacgagc aaatgtacct gcagcagctc atcatgcagc tc                            42

<210> SEQ ID NO 40
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agggcatgag ctgcatgatg agctgctggt ctactatcca cgatttaac                     49

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgttaatagc agctcatcac gcagctc                                             27

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agggcatgag ctgcgtgatg agctgctatt aaca                                     34

<210> SEQ ID NO 43
<211> LENGTH: 30
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 43
atgtcaagat cacagatttt gggcgggcca                                         30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atgtcaagat cacagatttt gggctggcca                                         30

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaggacgagc aaatgtacct gcagtcaaga tcacagattt tgg                          43

<210> SEQ ID NO 46
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcccgcccaa aatctgtgat cttgactggt ctactatcca cgatttaac                    49

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgttaatagt caagatcaca gattttgg                                           28

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gccagcccaa aatctgtgat cttgactatt aaca                                    34

<210> SEQ ID NO 49
<211> LENGTH: 30
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 49
tggccaaaca gctgggtgcg aagagaaag                                      30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tggccaaact gctgggtgcg gaagagaaag                                     30

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aaggacgagc aaatgtacct gcagccaaac agctgggtgc g                        41

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttctcttcc gcacccagct gtttggctgg tctactatcc acgatttaac               50

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tagttgccaa actgctgggt gcg                                            23

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttctcttccg cacccagcag tttggcaact a                                   31

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
actacctttc tacggacgtg ggattctgca                                               30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
actacctttc tacggacgtg ggatcctgca                                               30

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaggacgagc aaatgtacct gcataccttt ctacggacgt g                                  41

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cagaatccca cgtccgtaga aaggtatggt ctactatcca cgatttaac                          49

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgttaatata cctttctacg gacgtg                                                   26

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
caggatccca cgtccgtaga aaggtatatt aaca                                          34

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ttccagtggc catcaaagtg tcgagggaaa                                30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttccagtggc catcaaagtg ttgagggaaa                                30

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aaggacgagc aaatgtacct gcaccagtgg ccatcaaagt g                   41

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tccctcgaca ctttgatggc cactggtggt ctactatcca cgatttaac           49

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gttaatacca gtggccatca aagtg                                     25

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tccctcaaca ctttgatggc cactggtatt aac                            33

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 67
ggatgtgcgg ctcatacaca gggacttggc                                     30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggatgtgcgg ctcgtacaca gggacttggc                                     30

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aaggacgagc aaatgtacct gcaatgtgcg gctcatacac a                        41

<210> SEQ ID NO 70
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
caagtccctg tgtatgagcc gcacattggt ctactatcca cgatttaac                49

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gttaataatg tgcggctcgt acaca                                          25

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
caagtccctg tgtacgagcc gcacattatt aac                                 33

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
```
cttgtggtag ttggagctgc tggc				24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cttgtggtag ttggagctgg tggc				24

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aaggacgagc aaatgtacct gcaacttgtg gtagttggag				40

<210> SEQ ID NO 76
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gccagcagct ccaactacca caagttggtc tactatccac gatttaac				48

<210> SEQ ID NO 77
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ccgctgtggt agttgga				17

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caccagctcc aactaccaca gcgc				24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cttgtggtag ttggagcttg tggc                                          24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cttgtggtag ttggagctgg tggc                                          24

<210> SEQ ID NO 81
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaggacgagc aaatgtacct gcaacttgtg gtagttggag c                       41

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gccacaagct ccaactacca caagttggtc tactatccac gatttaac                48

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ccgctgtggt agttgga                                                  17

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
caccagctcc aactaccaca gcgc                                          24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cttgtggtag ttggagctga tggc                                          24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cttgtggtag ttggagctgg tggc                                           24

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaggacgagc aaatgtacct gcaacttgtg gtagttggag                          40

<210> SEQ ID NO 88
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gccatcagct ccaactacca caagttggtc tactatccac gatttaac                 48

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcatctgtgg tagttgga                                                  18

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
caccagctcc aactaccaca gatgc                                          25

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cttgtggtag ttggagctcg tggc                                           24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cttgtggtag ttggagctgg tggc                                          24

<210> SEQ ID NO 93
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aaggacgagc aaatgtacct gcaacttgtg gtagttggag c                       41

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gccacgagct ccaactacca caagttggtc tactatccac gatttaac                48

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccgctgtggt agttgga                                                  17

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caccagctcc aactaccaca gcgc                                          24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cttgtggtag ttggagctag tggc                                          24

```
<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cttgtggtag ttggagctgg tggc                                              24

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aaggacgagc aaatgtacct gcaacttgtg gtagttggag                             40

<210> SEQ ID NO 100
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gccactagct ccaactacca caagttggtc tactatccac gatttaac                    48

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgctgtggt agttgga                                                      17

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caccagctcc aactaccaca gcgc                                              24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cttgtggtag ttggagctgt tggc                                              24

<210> SEQ ID NO 104
```

<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
cttgtggtag ttggagctgg tggc   24

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
aaggacgagc aaatgtacct gcaacttgtg gtagttggag   40

<210> SEQ ID NO 106
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
gccaacagct ccaactacca caagttggtc tactatccac gatttaac   48

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
ccgctgtggt agttgga   17

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
caccagctcc aactaccaca gcgc   24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
cttgtggtag ttggagctgg ttgc   24

<210> SEQ ID NO 110
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cttgtggtag ttggagctgg tggc                                           24

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aaggacgagc aaatgtacct gcaacttgtg gtagttggag                          40

<210> SEQ ID NO 112
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcaaccagct ccaactacca caagttggtc tactatccac gatttaac                 48

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
caggctgtgg tagttgga                                                  18

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caccagctcc aactaccaca gcctg                                          25

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cttgtggtag ttggagctgg tgacgtaggc                                     30

<210> SEQ ID NO 116
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
cttgtggtag ttggagctgg tggcgtaggc                                          30

<210> SEQ ID NO 117
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aaggacgagc aaatgtacct gcatgtggta gttggagctg g                             41

<210> SEQ ID NO 118
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ctacgtcacc agctccaact accacatggt ctactatcca cgatttaac                     49

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ttaatatgtg gtagttggag ctggt                                               25

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ctacgccacc agctccaact accacatatt aa                                       32

<210> SEQ ID NO 121
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cttgtggtag ttggagctgg tgtcgtaggc                                          30

<210> SEQ ID NO 122
<211> LENGTH: 30
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 122
cttgtggtag ttggagctgg tggcgtaggc                                          30

<210> SEQ ID NO 123
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
aaggacgagc aaatgtacct gcatgtggta gttggagctg g                             41

<210> SEQ ID NO 124
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ctacgacacc agctccaact accacatggt ctactatcca cgatttaac                     49

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
aggtgtggta gttggagctg gt                                                  22

<210> SEQ ID NO 126
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ctacgccacc agctccaact accacacct                                           29

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gcaggtcacg aggagtacag tgcaatgagg                                          30

<210> SEQ ID NO 128
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 128
gcaggtcaag aggagtacag tgcaatgagg                                      30

<210> SEQ ID NO 129
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
aaggacgagc aaatgtacct gcaaggtcac gaggagtaca g                         41

<210> SEQ ID NO 130
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tcattgcact gtactcctcg tgaccttggt ctactatcca cgatttaac                 49

<210> SEQ ID NO 131
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgttaataag gtcaagagga gtacag                                          26

<210> SEQ ID NO 132
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tcattgcact gtactcctct tgaccttatt aaca                                 34

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acccagaatc agaaggtggg agaactgaag                                      30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 134
acccagaagc agaaggtggg agaactgaag                                      30

<210> SEQ ID NO 135
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aaggacgagc aaatgtacct gcaccagaat cagaaggtgg g                         41

<210> SEQ ID NO 136
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ttcagttctc ccaccttctg attctggtgg tctactatcc acgatttaac                50

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aggccagaag cagaaggtgg g                                               21

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tcagttctcc caccttctgc ttctggcct                                       29

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gtggttggag catgtggtgt tgggaaaagc                                      30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gtggttggag caggtggtgt tgggaaaagc                                              30

<210> SEQ ID NO 141
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
aaggacgagc aaatgtacct gcaggttgga gcatgtggtg tt                                42

<210> SEQ ID NO 142
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cttttcccaa caccacatgc tccaacctgg tctactatcc acgatttaac                        50

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
aggggttgga gcaggtggtg t                                                       21

<210> SEQ ID NO 144
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ttttcccaac accacctgct ccaacccct                                               29

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gtggttggag cagatggtgt tgggaaaagc                                              30

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 146
gtggttggag caggtggtgt tgggaaaagc                                      30

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
aaggacgagc aaatgtacct gcaggttgga gcagatggtg tt                        42

<210> SEQ ID NO 148
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
cttttcccaa caccatctgc tccaacctgg tctactatcc acgatttaac                50

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aggggttgga gcaggtggtg t                                               21

<210> SEQ ID NO 150
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ttttcccaac accacctgct ccaaccct                                        29

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tacaaactgg tggtggttgg agcaagtggt                                      30

<210> SEQ ID NO 152
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
```

```
tacaaactgg tggtggttgg agcaggtggt                                    30
```

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153

```
aaggacgagc aaatgtacct gctcaaactg gtggtggttg ga                      42
```

<210> SEQ ID NO 154
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154

```
cacttgctcc aaccaccacc agtttgaggt ctactatcca cgatttaac               49
```

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
cgatcaaact ggtggtggtt gga                                           23
```

<210> SEQ ID NO 156
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156

```
cacctgctcc aaccaccacc agtttgatcg                                    30
```

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157

```
gtggttggag caggtgatgt tgggaaaagc                                    30
```

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158

```
gtggttggag caggtggtgt tgggaaaagc                                        30
```

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159

```
aaggacgagc aaatgtacct gcaggttgga gcaggtgatg tt                          42
```

<210> SEQ ID NO 160
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160

```
cttttcccaa catcacctgc tccaacctgg tctactatcc acgatttaac                  50
```

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161

```
aggggttgga gcaggtggtg t                                                 21
```

<210> SEQ ID NO 162
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162

```
ttttcccaac accacctgct ccaaccoct                                         29
```

<210> SEQ ID NO 163
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163

```
atactggata cagctggaca tgaagagtac                                        30
```

<210> SEQ ID NO 164
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

```
atactggata cagctggaca agaagagtac                                        30
```

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aaggacgagc aaatgtacct gcaactggat acagctggac                         40

<210> SEQ ID NO 166
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
actcttcatg tccagctgta tccagttggt ctactatcca cgatttaac               49

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgttaataac tggatacagc tggac                                         25

<210> SEQ ID NO 168
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
actcttcttg tccagctgta tccagttatt aaca                               34

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
atactggata cagctggaaa agaagagtac                                    30

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
atactggata cagctggaca agaagagtac                                    30

```
<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
aaggacgagc aaatgtacct gcaactggat acagctggaa                              40

<210> SEQ ID NO 172
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172 actcttctttt tccagctgta tccagttggt ctactatcca cgatttaac                   49

<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tgttaataac tggatacagc tggac                                              25

<210> SEQ ID NO 174
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
actcttcttg tccagctgta tccagttatt aaca                                    34

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggacatactg gatacagctg gactagaaga                                         30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggacatactg gatacagctg gacaagaaga                                         30
```

```
<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aaggacgagc aaatgtacct gcaacatact ggatacagct                              40

<210> SEQ ID NO 178
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ttctagtcca gctgtatcca gtatgttggt ctactatcca cgatttaac                    49

<210> SEQ ID NO 179
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gttaataaca tactggatac agctg                                              25

<210> SEQ ID NO 180
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
ttcttgtcca gctgtatcca gtatgttatt aac                                     33

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atactggata cagctggacg agaagagtac                                         30

<210> SEQ ID NO 182
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atactggata cagctggaca agaagagtac                                         30

<210> SEQ ID NO 183
```

```
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aaggacgagc aaatgtacct gcaactggat acagctggac g                                41

<210> SEQ ID NO 184
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tactcttctc gtccagctgt atccagttgg tctactatcc acgatttaac                       50

<210> SEQ ID NO 185
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gtgttaataa ctggatacag ctggac                                                 26

<210> SEQ ID NO 186
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
actcttcttg tccagctgta tccagttatt aacac                                       35

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ctctctaaaa tcactgagca ggagaaagat                                             30

<210> SEQ ID NO 188
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ctctctgaaa tcactgagca ggagaaagat                                             30

<210> SEQ ID NO 189
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aaggacgagc aaatgtacct gcactctaaa atcactgagc a                          41

<210> SEQ ID NO 190
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tctttctcct gctcagtgat tttagagtgg tctactatcc acgatttaac                 50

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
aggctctgaa atcactgagc a                                                21

<210> SEQ ID NO 192
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ctttctcctg ctcagtgatt tcagagcct                                        29

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
agatcctctc tctgaaatca ctaagcagga                                       30

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
agatcctctc tctgaaatca ctgagcagga                                       30

<210> SEQ ID NO 195
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 195
aaggacgagc aaatgtacct gcaatcctct ctctgaaatc ac                        42

<210> SEQ ID NO 196
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cctgcttagt gatttcagag agaggattgg tctactatcc acgatttaac                50

<210> SEQ ID NO 197
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ttaataatcc tctctctgaa atcac                                           25

<210> SEQ ID NO 198
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ctgctcagtg atttcagaga gaggattatt aa                                   32

<210> SEQ ID NO 199
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgatgcactt catggtggct ggacaacaaa                                      30

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tgatgcacat catggtggct ggacaacaaa                                      30

<210> SEQ ID NO 201
<211> LENGTH: 41
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 201
aaggacgagc aaatgtacct gcaatgcact tcatggtggc t                           41

<210> SEQ ID NO 202
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tgttgtccag ccaccatgaa gtgcattggt ctactatcca cgatttaac                   49

<210> SEQ ID NO 203
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tgttaataat gcacatcatg gtggct                                            26

<210> SEQ ID NO 204
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tgttgtccag ccaccatgat gtgcattatt aaca                                   34

<210> SEQ ID NO 205
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tgatgcacgt catggtggct ggacaacaaa                                        30

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tgatgcacat catggtggct ggacaacaaa                                        30

<210> SEQ ID NO 207
<211> LENGTH: 41
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 207
aaggacgagc aaatgtacct gcaatgcacg tcatggtggc t                          41

<210> SEQ ID NO 208
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tgttgtccag ccaccatgac gtgcattggt ctactatcca cgatttaac                  49

<210> SEQ ID NO 209
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtgttaataa tgcacatcat ggtggct                                          27

<210> SEQ ID NO 210
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tgttgtccag ccaccatgat gtgcattatt aacac                                 35

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
atcgactcca ccgaggtcat ctactagccg                                       30

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
atcgactcca ccgaggtcat ctaccagccg                                       30

<210> SEQ ID NO 213
<211> LENGTH: 41
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 213
aaggacgagc aaatgtacct gcacgactcc accgaggtca t          41

<210> SEQ ID NO 214
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gctggtagat gacctcggtg gagtcgtggt ctactatcca cgatttaac   49

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
caccacgact ccaccgaggt cat                              23

<210> SEQ ID NO 216
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gctggtagat gacctcggtg gagtcgtggt g                     31

<210> SEQ ID NO 217
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
atcccgggcg actgtggccc cctgctctct                       30

<210> SEQ ID NO 218
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
atcccgggcg actgtggccc cccgctctct                       30

<210> SEQ ID NO 219
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aaggacgagc aaatgtacct gcacccgggc gactgtggcc cc        42

<210> SEQ ID NO 220
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
agagcagggg gccacagtcg cccgggtggt ctactatcca cgatttaac        49

<210> SEQ ID NO 221
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tgttaatacc cgggcgactg tggcccc        27

<210> SEQ ID NO 222
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
agagcggggg gccacagtcg cccgggtatt aaca        34

<210> SEQ ID NO 223
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aggacctctt ggacatcgag gatgacatca        30

<210> SEQ ID NO 224
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
aggacctctt cgacatcgag gatgacatca        30

<210> SEQ ID NO 225
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aaggacgagc aaatgtacct gcagacctct tggacatcga g    41

<210> SEQ ID NO 226
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
atgtcatcct cgatgtccaa gaggtctggt ctactatcca cgatttaac    49

<210> SEQ ID NO 227
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gttaatagac ctcttcgaca tcgag    25

<210> SEQ ID NO 228
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
atgtcatcct cgatgtcgaa gaggtctatt aac    33

<210> SEQ ID NO 229
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gttgtgaggc actgccccca ccatgagcgc    30

<210> SEQ ID NO 230
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gttgtgaggc gctgccccca ccatgagcgc    30

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
aaggacgagc aaatgtacct gcatgtgagg cactgccccc ac                42

<210> SEQ ID NO 232
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gctcatggtg ggggcagtgc ctcacatggt ctactatcca cgatttaac         49

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gtcgaggcgc tgcccccacc atg                                     23

<210> SEQ ID NO 234
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
agcgctcatg gtgggggcag cgcctcgac                               29

<210> SEQ ID NO 235
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
actttttgac atagtgtggt ggtgccctat                              30

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
acttttcgac atagtgtggt ggtgccctat                              30

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
aaggacgagc aaatgtacct gcatttttga catagtgtgg tg    42

<210> SEQ ID NO 238
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
agggcaccac cacactatgt caaaaatggt ctactatcca cgatttaac    49

<210> SEQ ID NO 239
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
aagacaattt tcgacatagt gtggtg    26

<210> SEQ ID NO 240
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
agggcaccac cacactatgt cgaaaattgt ctt    33

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cgacatagtg tggtggtgcc ctgtgagccg    30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
cgacatagtg tggtggtgcc ctatgagccg    30

<210> SEQ ID NO 243
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
aaggacgagc aaatgtacct gcaacatagt gtggtggtgc cc    42

<210> SEQ ID NO 244
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gctcacaggg caccaccaca ctatgttggt ctactatcca cgatttaac          49

<210> SEQ ID NO 245
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tgttaataac atagtgtggt ggtgcc                                    26

<210> SEQ ID NO 246
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gctcataggg caccaccaca ctatgttatt aaca                           34

<210> SEQ ID NO 247
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ttcctgcatg ggcggcatga accagaggcc                                30

<210> SEQ ID NO 248
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ttcctgcatg ggcggcatga accggaggcc                                30

<210> SEQ ID NO 249
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
aaggacgagc aaatgtacct gcacctgcat gggcggcatg a                   41

<210> SEQ ID NO 250
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cctctggttc atgccgccca tgcaggtggt ctactatcca cgatttaac            49

<210> SEQ ID NO 251
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gccctgcatg ggcggcatga ac                                         22

<210> SEQ ID NO 252
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
cctccggttc atgccgccca tgcagggc                                   28

<210> SEQ ID NO 253
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
atgaactgga ggcccatcct caccatcatc                                 30

<210> SEQ ID NO 254
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
atgaaccgga ggcccatcct caccatcatc                                 30

<210> SEQ ID NO 255
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
aaggacgagc aaatgtacct gcagaactgg aggcccatcc t                    41

<210> SEQ ID NO 256
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tgatggtgag gatgggcctc cagttctggt ctactatcca cgatttaac           49

<210> SEQ ID NO 257
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgttaataga accggaggcc catcct                                    26

<210> SEQ ID NO 258
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
tgatggtgag gatgggcctc cggttctatt aaca                           34

<210> SEQ ID NO 259
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
acggaacagc tttgaggtgt gtgtttgtgc                                30

<210> SEQ ID NO 260
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
acggaacagc tttgaggtgc gtgtttgtgc                                30

<210> SEQ ID NO 261
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
aaggacgagc aaatgtacct gcaggaacag ctttgaggtg t                   41

<210> SEQ ID NO 262

<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 262
acaaacacac acctcaaagc tgttcctggt ctactatcca cgatttaac                49

<210> SEQ ID NO 263
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
tgttaatagg aacagctttg aggtgc                                          26

<210> SEQ ID NO 264
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 264
acaaacacgc acctcaaagc tgttcctatt aaca                                 34

<210> SEQ ID NO 265
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 265
aggtgcatgt ttgtgcctgt cctgggagag                                      30

<210> SEQ ID NO 266
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
aggtgcgtgt ttgtgcctgt cctgggagag                                      30

<210> SEQ ID NO 267
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 267
aaggacgagc aaatgtacct gcagtgcatg tttgtgcctg t                         41

<210> SEQ ID NO 268
<211> LENGTH: 49

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ctcccaggac aggcacaaac atgcactggt ctactatcca cgatttaac         49

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
agttgtgcgt gtttgtgcct gtc                                      23

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ctcccaggac aggcacaaac acgcacaact                               30

<210> SEQ ID NO 271
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gggagagact ggcgcacaga ggaagagaat                               30

<210> SEQ ID NO 272
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gggagagacc ggcgcacaga ggaagagaat                               30

<210> SEQ ID NO 273
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aaggacgagc aaatgtacct gcagagagac tggcgcacag a                  41

<210> SEQ ID NO 274
<211> LENGTH: 49
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 274
tctcttcctc tgtgcgccag tctctctggt ctactatcca cgatttaac        49

<210> SEQ ID NO 275
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gttaatagag agaccggcgc acaga        25

<210> SEQ ID NO 276
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tctcttcctc tgtgcgccgg tctctctatt aac        33

<210> SEQ ID NO 277
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gcagtttggc ccgcccaaaa tctgtgatct tgacatgctg cg        42

<210> SEQ ID NO 278
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cggtgtcagg catgtcaaga tcacagattt gggcggg        38

<210> SEQ ID NO 279
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
aatctgtgat cttgacatgc ctgacaccg        29

<210> SEQ ID NO 280
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 280
aagatcacag attttgggct ggccaaactg catctt                                 36

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
aagatgcagt ttggccagcc c                                                 21

<210> SEQ ID NO 282
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gcagtttggc cagcccaaaa tctgtgatct tgacatgctg cg                          42
```

COMPETITIVE COMPOSITIONS OF NUCLEIC ACID MOLECULES FOR ENRICHMENT OF RARE-ALLELE-BEARING SPECIES

CROSS-REFERENCE TO RELATED APPLICATIONS

The present application is a continuation application of International Application No. PCT/US15/26330, filed Apr. 17, 2015, which claims priority to U.S. Provisional Application No. 61/981,588 filed on Apr. 18, 2014, the disclosure of which is incorporated herein by reference in its entirety.

STATEMENT OF GOVERNMENT INTEREST

This invention was made with government support under Grant Number EB015331 awarded by the National Institute of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 15, 2015, is named 14-21011-WO_260947_00237_SL.txt and is 66,959 bytes in size.

BACKGROUND

Nucleic acids serve as important molecular markers for disease, and accurate detection of specific DNA and RNA sequences form the basis for many research and diagnostic products. However, many, if not most, current technology platforms struggle with distinguishing closely related nucleic acid sequences, such as those differing by a single nucleotide.

Discrimination of single nucleotide differences possesses two main applications: single nucleotide polymorphism (SNP) genotyping; and rare allele detection. In SNP genotyping, the target DNA sample is 100% of one allele, or 50% distributed between two alleles, and thus, SNP genotyping is generally a solved problem with commercially available solutions.

In rare allele detection, a target DNA sample may possess less than 1% of a particular rare allele (referred to herein as a "a rare-allele-bearing species"). For example, circulating cell-free nucleic acids bearing cancer mutation can be indicative of cancer emergence or recurrence, and there is strong interest in detecting such species. Specialized technology platforms have been marketed that are capable of detecting rare alleles down to between 0.1% and 0.001% frequencies, but these generally require expensive instruments that are not commonly available. Simultaneously, manufacturers of more broad-based equipment, are interested in novel molecular technologies that can enhance the capabilities of their platforms to enable rare allele and mutation detection. However, to date, there is currently not an accurate and inexpensive detection system that can be used with a variety of probe species.

SUMMARY

The present disclosure provides compositions and methods for use in probe systems. In one embodiment, a nucleic acid detection composition is provided for detecting a rare-allele-bearing nucleic acid species in a sample comprising an excess of a dominant-allele-bearing nucleic acid species, wherein the sequences of the rare-allele-bearing and dominant-allele-bearing nucleic acid species are conserved except for one or more nucleotides in a common, aligned region. The common aligned region in the dominant-allele-bearing nucleic acid is referred to as a non-target nucleic acid sequence (Variant) and the common region on the rare-allele-bearing nucleic acid species is referred to as a target nucleic acid sequence (Target). In one instance, the composition comprises two probe complexes and two separate oligonucleotides. The first probe complex is specific to the target nucleic acid sequence and is referred to herein as a "target nucleic acid probe" or "Probe," whereas the second probe complex is specific to the variant nucleic acid sequence and is referred to herein as a "variant nucleic acid probe" or "Sink." The Probe comprises a first target probe oligonucleotide and a second target probe oligonucleotide. The first target probe oligonucleotide comprises a target probe complement region that is complementary to the target nucleic acid sequence and one or more non-complement regions that are not complementary to the target nucleic acid sequence. The second target probe oligonucleotide comprises a target probe protector region that is complementary to a first target probe complement subsequence of the target probe complement region and one or more nonprotector regions. Given that the first and second target probe oligonucleotide possess complementary sequence, the Probe comprises a target double-stranded probe portion and a target single-stranded probe portion, wherein the target double-stranded probe portion comprises the first target probe complement subsequence and the target probe protector region, and the target single-stranded probe portion comprises a second target probe complement subsequence of the target probe complement region.

The variant nucleic acid probe also comprises a first and second variant probe oligonucleotide. The first variant probe oligonucleotide comprises a variant probe complement region that is complementary to the variant nucleic acid sequence and one or more variant non-complement regions that are not complementary to the variant nucleic acid sequence. The second variant probe oligonucleotide comprises a variant probe protector region that is complementary to a first variant probe complement subsequence of the variant probe complement region and one or more variant non-protector regions. Similar to the Probe, the variant Sink comprises a variant double-stranded probe portion and a variant single-stranded probe portion, wherein the variant double-stranded probe portion comprises the first variant probe complement subsequence and the variant probe protector region, whereas the variant single-stranded probe portion comprises a second variant probe complement subsequence of the variant probe complement region.

The target probe complement region and the variant probe complement region share at least two conserved sequences separated by a non-conserved sequence. The non-conserved sequence can be a single nucleotide difference between the Probe and Sink complement regions thereby contributing to each probe's specificity for the target nucleic acid sequence and the variant nucleic acid sequence, respectively. The non-conserved sequence may encompass a single nucleotide at a common position, such as in the instance of a single nucleotide polymorphism (SNP) in the target nucleic acid sequence. In the instance that the target nucleic acid sequence and the variant nucleic acid sequence differ by a single nucleotide at multiple common positions, the target and variant complement regions may share more than two conserved sequences. It should also be understood that the target and variant complement regions may not be directed to entirely the same sequence region or frame on the target and variant nucleic acid sequence. For example, the target complement region may be directed to a sequence on the target nucleic acid that begins several nucleotides 5' of the beginning of the variant nucleic acid sequence that the variant complement region is targeting. Thus, there may be other non-conserved sequences in the target and variant complement regions that are not located between the conserved sequences and instead, are located at the 3' or 5' ends of the target and variant complement regions.

In certain embodiments, the first target probe oligonucleotide comprises a detectable label or a capture moiety conjugated thereto and the second target probe oligonucleotide comprises a quencher sufficient to prevent detection of the detectable label or capture of the capture moiety.

In certain other embodiments, the composition may further comprise a third target probe oligonucleotide hybridized to a target probe non-complement region of the first target probe oligonucleotide, wherein the third target probe oligonucleotide comprises a detectable label or a capture moiety conjugated thereto. In addition, the composition may further comprise a fourth target probe oligonucleotide hybridized to a target probe non-protector region of the second target probe oligonucleotide, wherein the fourth target probe oligonucleotide comprises a quencher sufficient to prevent detection of the detectable label or capture of the capture moiety.

The composition also comprises a target auxiliary oligonucleotide and a variant auxiliary oligonucleotide. Each of these oligonucleotides are identical in length and sequence to the second target probe oligonucleotide and the second variant probe oligonucleotide, respectively. Thus, the second target and variant probe oligonucleotides are present in the composition in excess of the first target and variant probes oligonucleotides thereby yielding a concentration of second target and variant probe oligonucleotides that are separate from the Probe and Sink complexes, this excess provides the target and variant auxiliary oligonucleotides. In other embodiments, the target and variant auxiliary oligonucleotides may differ slightly in length and/or sequence to the second target and variant probe oligonucleotides.

As discussed in more detail herein below, the target nucleic acid probe and variant nucleic acid probes may comprise different morphologies. In one instance, the target nucleic acid probe may comprise an X-probe morphology while the variant nucleic acid probe may also comprise an X-probe morphology or a ultra-specific, toehold morphology, similar to that described in the above embodiment. The description of the X-probe morphology is described with respect to the target nucleic acid probe, but it should be understood that the same design could also apply to the variant probe. In the X-probe morphology, the target probe, variant probe, or both may further comprise a third oligonucleotide and a fourth oligonucleotide, wherein the third oligonucleotide comprises a first target (or variant) probe oligonucleotide-specific subsequence and a fourth oligonucleotide specific subsequence, wherein the first target (or variant) probe oligonucleotide-specific subsequence is complementary to a target (or variant) probe non-complement region of the first target (or variant) probe oligonucleotide, wherein the fourth oligonucleotide comprises a second target (or variant) probe oligonucleotide-specific subsequence and a third oligonucleotide-specific subsequence, wherein the second target (or variant) probe oligonucleotide-specific subsequence is complementary to a target (or variant) probe non-protector region of the second target (or variant) probe oligonucleotide, wherein the target (or variant) probe non-protector region of the second target (or variant) probe oligonucleotide does not overlap with the target (or variant) probe protector region, wherein the fourth oligonucleotide-specific subsequence is complementary to the third oligonucleotide-specific subsequence, and wherein the target (or variant) auxiliary oligonucleotide further comprises the fourth oligonucleotide.

In the X-probe morphology, the fourth oligonucleotide-specific subsequence of the third oligonucleotide may comprises a detectable label or capture moiety conjugated thereto and the third oligonucleotide-specific subsequence of the fourth oligonucleotide comprises a quencher sufficient to prevent detection of the detectable label or capture of the capture moiety.

In one embodiment, the target nucleic acid probe has a target reaction standard free energy ($\Delta G°_{rxn1}$), wherein the variant nucleic acid probe has a variant reaction standard free energy ($\Delta G°_{rxn2}$), and wherein $\Delta G°_{rxn1}$ is greater than the sum of $\Delta G°_{rxn2}$+1 kcal/mol.

In another embodiment, the target nucleic acid probe has a concentration-adjusted target reaction standard free energy defined as $\Delta G°_{rxn1}+R\tau \ln([P_t]/[P_tC_t])$, wherein the variant nucleic acid probe has a variant reaction standard free energy defined as $\Delta G°_{rxn2}+R\tau \ln([P_v]/[P_vC_v])$, where R is the ideal gas constant, $\tau$ is the temperature in Kelvin, $P_t$ is the initial concentration of the target auxiliary oligonucleotide, $P_tC_t$ is the initial concentration of the target nucleic acid probe, $P_v$ is the initial concentration of the variant auxiliary oligonucleotide, $P_vC_v$ is the initial concentration of the variant nucleic acid probe, wherein the concentration-adjusted reaction standard free energy of the target nucleic acid probe is greater than the sum of the concentration-adjusted reaction standard free energy of the variant nucleic acid probe +1 kcal/mol.

In another embodiment, the target nucleic acid probe has a target reaction standard free energy ($\Delta G°_{rxn1}$), wherein the variant nucleic acid probe has a variant reaction standard free energy ($\Delta G°_{rxn2}$), and wherein $\Delta G°_{rxn1}$ is greater than $\Delta G°_{rxn2}$, and $G°_{rxn2}$ is greater than −7 kcal/mol.

In certain embodiments, the concentration of the variant nucleic acid probe relative to the concentration of the target nucleic acid probe is from greater than 1:1 to about less than 100000:1. In other embodiments, the concentration of the variant nucleic acid probe relative to the concentration of the target nucleic acid probe is from greater than 10:1 to less than 10000:1. In other embodiments, the concentration of the variant nucleic acid probe relative to the concentration of the target nucleic acid probe is from greater than 100:1 to less than 1000:1. In yet another embodiment, the concentration of the variant nucleic acid probe relative to the concentration of the target nucleic acid probe is about 900:1.

In certain embodiments, the concentration of the target auxiliary oligonucleotide relative to the concentration of the target nucleic acid probe is from greater than 1:1000 to less than 100000:1. In other embodiments, the concentration of the target auxiliary oligonucleotide relative to the concentration of the target nucleic acid probe is from greater than 1:100 to less than 10000:1. In other embodiments, the concentration of the target auxiliary oligonucleotide relative to the concentration of the target nucleic acid probe is from greater than 1:10 to less than 1000:1.

In certain embodiments, the concentration of the variant auxiliary oligonucleotide relative to the concentration of the variant nucleic acid probe is from greater than 1:1000 to less than 100000:1. In other embodiments, the concentration of the variant auxiliary oligonucleotide relative to the concentration of the variant nucleic acid probe is from greater than 1:100 to less than 10000:1. In other embodiments, the concentration of the variant auxiliary oligonucleotide relative to the concentration of the variant nucleic acid probe is from greater than 1:10 to less than 1000:1.

In the above or other applicable embodiments, the target nucleic acid probe (Probe) and the variant nucleic acid probe (Sink) comprise single or double Blocks, where a Block is either a strand or a complex that comprises 2 or more oligonucleotides formed through Watson-Crick hybridization reactions.

In one or more of any of the applicable above embodiments, the equilibrium yield of hybridization between the variant nucleic acid probe and the variant nucleic acid sequence (Variant) as determined in isolation is greater than the equilibrium yield of hybridization between the target nucleic acid probe and the target nucleic acid sequence (Target) as determined in isolation.

In one or more of any of the applicable above embodiments, the target nucleic acid probe is an ultraspecific probe, a fine-tuned ultraspecific probe, an X-Probe, a Yin-Yang probe, or any other nucleic acid probe molecule which comprises double Blocks, a Target-binding Block and an Auxiliary Block or protector, and releases the Auxiliary Block concurrently with the hybridization of the Target. In this instance, the probe may include an excess of Auxiliary Block species separate from and in addition to the Auxiliary Block species that is part of the composition (also referred to as "target auxiliary oligonucleotide").

In one or more of any of the applicable above embodiments, the reaction standard free energy $\Delta G°_{rxn1}$ between the target nucleic acid probe and the Target satisfies the inequalities $\Delta G°_{rxn1} > -6$ kcal/mol and $\Delta G°_{rxn1} < +6$ kcal/mol at operational temperature and buffer conditions.

In one or more of any of the applicable above embodiments, the initial concentrations of the target auxiliary oligonucleotide [A] and the initial concentration of the target nucleic acid probe [P] satisfy the inequalities [A]/[P]>0.001 and [A]/[P]<1000.

In one or more of any of the applicable above embodiments, the reaction standard free energy between the target nucleic acid probe and the Target ($\Delta G°_{rxn1}$), the initial concentrations of the target auxiliary oligonucleotide [A], and the initial concentration of the target nucleic acid probe [Probe] satisfy the inequalities $\Delta G°_{rxn1}+R\tau \ln([A]/[Probe])>-4$ kcal/mol and $\Delta G°_{rxn1}+R\tau \ln([A]/[Probe])<+3$ kcal/mol at the operational temperature and buffer conditions, where R is the ideal gas constant and $\tau$ is the temperature in Kelvin.

In one or more of any of the applicable above embodiments, the the target nucleic acid probe is a molecular beacon, a hairpin probe, a triple-stem probe, or any other nucleic acid probe molecule which comprises single Blocks, the Target-binding Block, and does not release an auxiliary nucleic acid species concurrently with the hybridization of the Target. In this embodiment, the reaction standard free energy $\Delta G°_{rxn1}$ between the target nucleic acid probe and the Target and the concentration of the target nucleic acid probe [Probe] satisfies the inequalities $\Delta G°_{rxn1}-R\tau \ln([Probe])>-4$ kcal/mol and $\Delta G°_{rxn1}-R\tau \ln([Probe])<+3$ kcal/mol at the operational temperature and buffer conditions, where R is the ideal gas constant and $\tau$ is the temperature in Kelvin.

In one or more of any of the applicable above embodiments, the variant nucleic acid probe (Sink) is an ultra-specific probe, a fine-tuned ultra-specific probe, an X-Probe, a Yin-Yang probe, or any other nucleic acid molecule which comprises double Blocks, a Target-binding Block and an Auxiliary Block, and releases the Auxiliary Block concurrently with the hybridization of the Variant. In this instance, the composition may include an excess of Auxiliary Block species separate from and in addition to the Auxiliary Block species that is part of the probe molecule (also referred to herein as the "variant auxiliary oligonucleotide").

In one or more of any of the applicable above embodiments, the reaction standard free energy between the variant nucleic acid probe and the Variant ($\Delta G°_{rxn2}$) satisfies the inequalities $\Delta G°_{rxn2} > -11$ kcal/mol and $\Delta G°_{rxn2} < +4$ kcal/mol at operational temperature and buffer conditions.

In one or more of any of the applicable above embodiments, the initial concentrations of the variant auxiliary oligonucleotide [B] and the initial concentration of the variant nucleic acid probe [S] satisfy the inequalities [B]/[S]>0.001 and [B]/[S]<1000.

In one or more of any of the applicable above embodiments, the reaction standard free energy between the variant nucleic acid probe and the Variant ($\Delta G°_{rxn2}$), the initial concentrations of the variant auxiliary oligonucleotide [B], and the initial concentration of the variant nucleic acid probe [Sink] satisfy the inequalities $\Delta G°_{rxn2}+R\tau \ln([B]/[Sink])>-7$ kcal/mol and $\Delta G°_{rxn2}+R\tau \ln([B]/[Sink])<+1$ kcal/mol at the operational temperature and buffer conditions, where R is the ideal gas constant and $\tau$ is the temperature in Kelvin.

In one or more of any of the applicable above embodiments, the variant nucleic acid probe is a molecular beacon, a hairpin probe, a triple-stem probe, or any other nucleic acid probe molecule which comprises single Blocks, the Target-binding Block, and does not release an auxiliary (protector) nucleic acid species concurrently with the hybridization of the Variant. In this embodiment, the reaction standard free energy between the variant nucleic acid probe and the Variant ($\Delta G°_{rxn2}$), and the concentration of the variant nucleic acid probe [Sink] satisfies the inequalities $\Delta G°_{rxn2}-R\tau \ln([Sink])>-7$ kcal/mol and $\Delta G°_{rxn2}-R\tau \ln([Sink])<+1$ kcal/mol at the operational temperature and buffer conditions, where R is the ideal gas constant and $\tau$ is the temperature in Kelvin.

In one embodiment, the target nucleic acid probe reacts with the Target with a reaction standard free energy ($\Delta G°_{rxn1}$), the variant nucleic acid probe reacts with the Variant with a reaction standard free energy ($\Delta G°_{rxn2}$), the initial concentration of the target auxiliary oligonucleotide [A], and the initial concentration of the variant auxiliary oligonucleotide [B] satisfies one or more of the following: $(\Delta G°_{rxn1}+R\tau \ln([A]/[Probe]))-(\Delta G°_{rxn2}-R\tau \ln([B]/[Sink])$ is between +8 kcal/mol and 0 kcal/mol; $(\Delta G°_{rxn1}+R\tau \ln([A]/[Probe])-\Delta G°_{rxn2}+R\tau \ln([Sink]))$ is between $-8$ kcal/mol and $-1$ kcal/mol; $(\Delta G°_{rxn1}+R\tau \ln[Probe])-(\Delta G°_{rxn2}-R\tau \ln[B]/[Sink])$ is between +8 kcal/mol and 0 kcal/mol; or $(\Delta G°_{rxn1}-R\tau \ln[Probe])-(\Delta G°_{rxn2}+R\tau \ln([Sink])$ is between +8 kcal/mol and 0 kcal/mol each as evaluated at operational temperature and buffer conditions.

In one or more of any of the applicable above embodiments, the first target probe oligonucleotide is functionalized with at least one chemical moiety for detection, localization, or reinforcement of hybridization, such as a fluorophore, a hapten, a biotin, an azide, a succinimide, or a minor groove binder.

In one or more of any of the applicable above embodiments, the first target probe oligonucleotide is joined via one or more hybridization interactions with an oligonucleotide that is functionalized with at least one chemical moiety for detection, localization, or reinforcement of hybridization, such as a fluorophore, a hapten, a biotin, an azide, a succinimide, or a minor groove binder.

In one or more of any of the applicable above embodiments, the first variant probe oligonucleotide is functionalized with at least one chemical moiety for localization or reinforcement of hybridization, such as a hapten, a biotin, an azide, a succinimide, a minor groove binder, or an intercalating fluorophore.

A method is also provided for use of any of the above described compositions in a reaction to isolate, identify, quantify, or detect a Target in a heterogeneous mixture of nucleic acids. In one embodiment, the method includes providing or obtaining a heterogeneous mixture of nucleic acids (sample), comprising a dominant allele-bearing species (Variant) and a rare allele-bearing species (Target), such that the aligned Variant and the Target differ by at least one nucleotide (polymorphic nucleotide(s)) in a subsequence. A target nucleic acid probe consistent with any of the composition embodiments described herein is admixed with the sample wherein the target nucleic acid probe hybridizes more favorably to the Target than to the Variant, and results in a reaction product in which a polymorphic nucleotide in the Target is Watson-Crick base paired to a corresponding nucleotide on the Probe. The method further comprises admixing a variant nucleic acid probe with the sample that hybridizes more favorably to the Variant than to the Target, and results in a product in which the polymorphic nucleotide in the Variant is Watson-Crick base paired to a corresponding nucleotide on the variant nucleic acid probe. In this method, the molar quantity or concentration of the variant nucleic acid probe admixed is in excess of the concentration of the target nucleic acid probe. In addition, the method may further comprise admixing a target auxiliary oligonucleotide and a variant auxiliary oligonucleotide, such as those described herein in the relative concentrations as disclosed herein. The target nucleic acid probe and the variant nucleic acid probe, along with any auxiliary oligonucleotides, may be added as a single composition to the sample.

In one or more of any of the applicable above embodiments, the ratio of sample concentration of the Variant divided by the sample concentration of the Target is X, where X is at least 20.

In one or more of any of the applicable above embodiments, subsequent to reaction with the Competitive Composition (Probe and Sink), the quantity of Variant that is bound to the Probe divided by the quantity of Target that is bound to the Probe is no more than (X/10), (X/30), (X/100), (X/300), or (X/1000).

In one or more of any of the applicable above embodiments, the reaction between the Competitive Composition (Probe and Sink) and the sample occurs isothermally and homogeneously in a well-mixed solution.

In one or more of any of the applicable above embodiments, the reaction between the Competitive Composition and the sample occurs in a well-mixed solution with a time-varying temperature profile.

In one or more of any of the applicable above embodiments, the time-varying temperature profile comprises a heating step to a temperature no less than 70° C., followed by a cooling step to a temperature no more than 65° C.

In one or more of any of the applicable above embodiments, the reaction between the Competitive Composition and the sample occurs in a well-mixed solution with a time-varying reaction buffer profile, such as via wash steps.

In one or more of any of the applicable above embodiments, the reaction between the Competitive Composition and the sample occurs on a surface, such as that of a slide for imaging or a nanoparticle.

In one or more of any of the applicable above embodiments, the Variant and Target molecules hybridized to Probe molecule induces a localized detectable fluorescence, chemiluminescence, or metallic precipitation suitable for imaging.

In one or more of any of the applicable above embodiments, the Variant and Target molecules hybridized to Probe molecule induces an enzymatic reaction, conditional fluorescence, or surface localization to enable detection or quantitation of the Target.

In one or more of any of the applicable above embodiments, the Variant and Target molecules hybridized to Probe molecule induces surface localization or other separation to enable purification or enrichment of Target from Variant and other species in the initial sample.

In one or more of any of the applicable above embodiments, Target imaging, detection, quantitation, enrichment, or purification is used for purposes of molecular diagnosis or characterization of a disease pathogen or biomarker, such as for cancer, for infectious diseases, or for genetic disorders.

BRIEF DESCRIPTION OF THE DRAWINGS

FIG. 7: Example Competitive Composition 42 (SEQ ID NOS 2, 249, 1, 250, 251 and 252, respectively, in order of appearance) for fluorescent detection of the rare TP53 R248Q (c.743G>A) mutation (T) (SEQ ID NO: 247) in a background of TP53 wildtype sequence (V) (SEQ ID NO: 248). Experiments were performed at 37° C. in 5×PBS buffer using synthetic oligonucleotides of the given sequences.

FIG. 9D provides an exemplary distribution of optimal $\Delta G°_{rxn}$ combinations at 1 hour reaction time. The figure shows optimal $\Delta G°_{rxn1}$ and $\Delta G°_{rxn2}$ values given by ordinary differential equation simulation for the 44 mutations discussed in FIG. 9A-9C with $\Delta\Delta G°$ values ranging from +1.8 kcal/mol to +5.9 kcal/mol at 37° C. Probe and Sink with $\Delta G°_{rxn1}$ and $\Delta G°_{rxn2}$ exhibit maximum specificity at 1 hour. As can be seen, optimal $\Delta G°_{rxn1}$ and $\Delta G°_{rxn2}$ for different $\Delta\Delta G°$ values. For the 44 SNV/WT pairs we have tested, optimal $\Delta G°_{rxn1}$ and $\Delta G°_{rxn2}$ values can vary from −1.6 to −0.6 kcal/mol and −6.4 to −2.8 kcal/mol, respectively.

FIG. 10A provides an experimental workflow diagram for Competitive Composition assays on PCR amplicons of human genomic DNA samples. Two extracted DNA samples from Coriell Cell Repository (NA18537 and NA18546) bearing single nucleotide polymorphisms at the SMAD7 locus are mixed 48 at 100:0, 99:1, 90:10, 10:90, 1:99, and 0:100 ratios to total concentrations of 2 ng/μL (50 μL), and amplified by asymmetric non-allele-specific PCR 49 to generate single-stranded amplicon 50. Competitive Compositions 51 that are designed to each allele are mixed with the assigned PCR product for detection 52.

FIG. 10B provides the fluorescence responses of Competitive Composition to each SNP for the experiment diagramed in FIG. 10A. In each experiment, 0.5 nM Probe and 10 nM Sink were reacted with 40 μL PCR product. Allele frequencies of SMAD7-C (as shown in black) and SMAD7-T (as shown in grey) in genomic DNA mixture prior to PCR are displayed in parentheses.

FIG. 11: List of incidental species present in the example Competitive Composition consisting of a conditionally fluorescent X-probe as Probe and a toehold probe as Sink. The additional species in solution are due to the formulation of the Probe 46 and Sink 47, which intentionally result in excess of certain species. All species shown here are considered and modeled in simulations.

FIG. 15 discloses SEQ ID NOS 277-282, respectively, in order of appearance.

DESCRIPTION OF THE INVENTION

Figure 1:
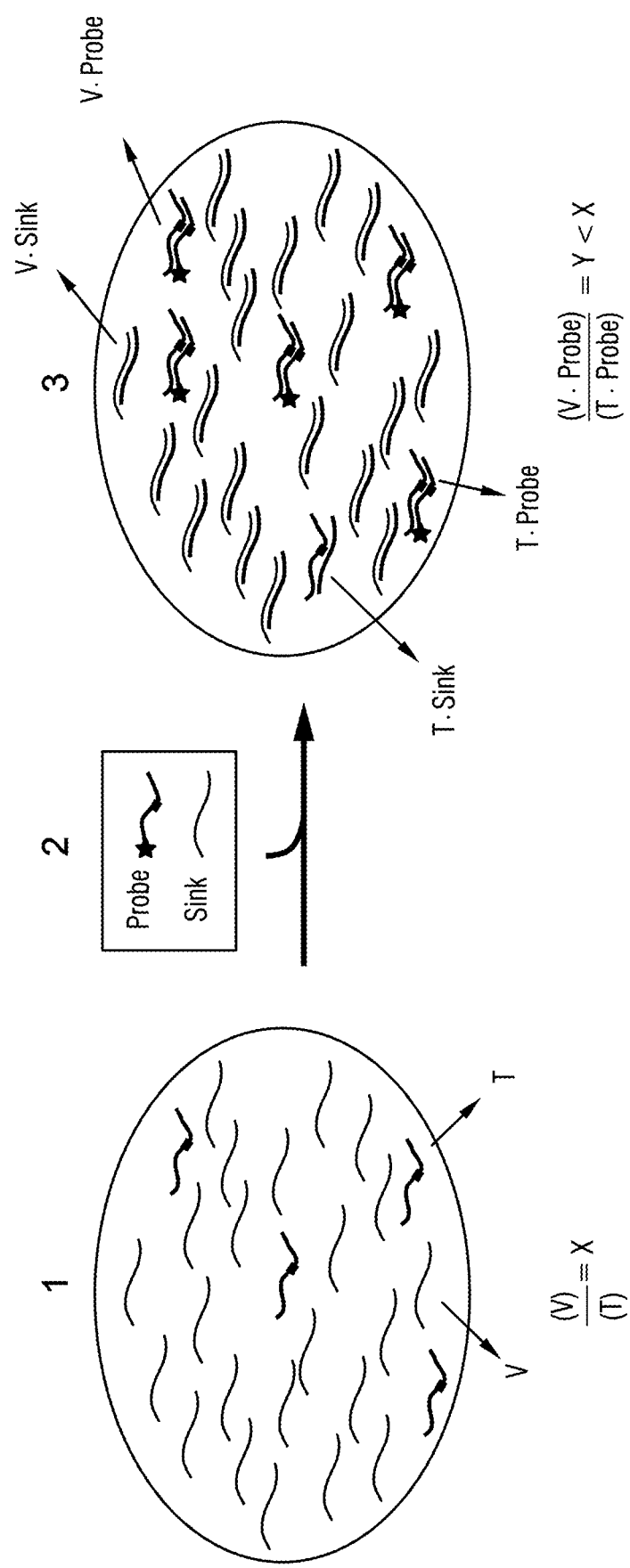
FIG. 1: Competitive Composition invention overview. The nucleic acid probe compositions of the present disclosure (also referred to as Competitive Composition) 2 is a reagent mixture that comprises target nucleic acid probe (Probe) that is specific to a Target species T and a variant nucleic acid probe (Sink) that is specific to a Variant species V. Here, the Probe binds more favorably to the Target than the Variant, and the Sink binds more favorably to the Variant than to the Target. The nucleic acid compositions of the present disclosure are used to isolate, identify, quantify, or detect a Target in a heterogeneous mixture of nucleic acids sample 1. The initial concentration ratio of the Variant to the Target in the sample is X. Upon completion of the reaction 3, the ratio of the amount of Target that is bound to the Probe (T•Probe) to the amount of Variant that is bound to be Probe (V•Probe) Y will be enriched relative to the initial ratio of Target and Variant in the Sample.

In the present disclosure, a novel reagent mixture composition (referred to herein as a "Competitive Composition) is provided. The Competitive Composition reacts with a heterogeneous sample mixture containing at last two closely related nucleic acid species: a dominant-allele-bearing species (Variant) and a rare-allele-bearing species (Target), with the former typically in excess of the latter (FIG. 1). The Variant and the Target molecules contain a highly similar subsequence, with length between, for example, 5 and 200 nucleotides, that differs by at least 1 nucleotide, known as the polymorphic nucleotide(s).

The Competitive Composition comprises a target nucleic acid probe (Probe) and a variant nucleic acid probe (Sink), with the later in excess concentration of the former, with the Sink reacting more favorably with the Variant than with the Target (due to the Sink's complementarity to the dominant allele nucleotide(s)) and the Probe reacting more favorably with the Target than with the Variant (due to the Probe's complementarity to the rare allele nucleotide(s)).

Mathematically, the concentration ratio of Variant to Target ([Variant]/[Target]) in the initial sample is here denoted as X, and the concentration ratio of Variant to Target that is bound to the Probe after the reaction is denoted as Y. By using Competitive Compositions designed based on the guidelines described here, Y will be much smaller than X; our experimental data across 44 different cancer-related mutations shows an average enrichment ratio (X/Y) of around 1000.

This enrichment ratio for the present Competitive Composition is significantly higher than prior art regarding the use of a single probes alone. In addition to showing experimental results that compare favorably to prior art, the present disclosure additionally includes validated theoretical analysis and simulations explaining why the Competitive Compositions described here provide an advantage over strategies.

Components of Competitive Composition

Figure 2:
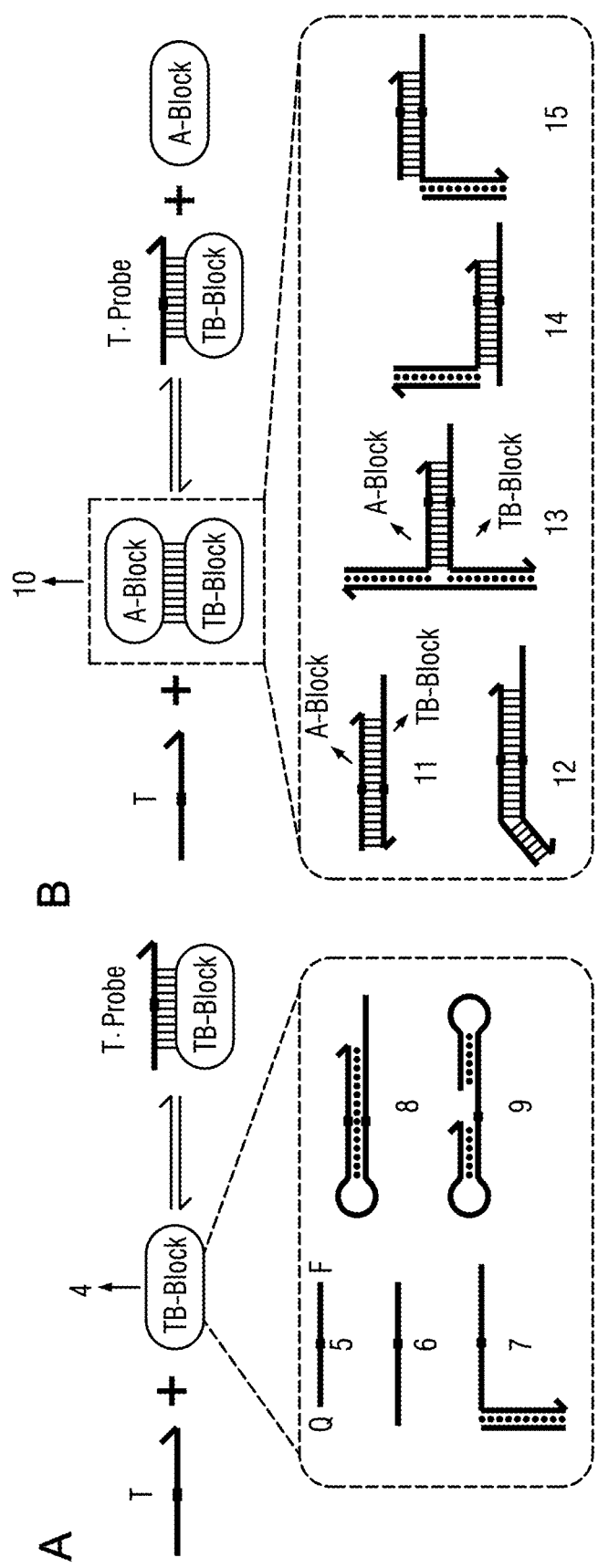
FIG. 2: Potential morphologies of Competitive Composition components. The Competitive Composition comprises a target nucleic acid probe (referred to hereinafter generally as "Probe") and a variant nucleic acid probe (referred to herein generally as "Sink"). Each can adopt one of a number of different nucleic acid molecule morphologies previously reported in literature, or yet to be reported. This figure shows a partial list of morphologies the Probe may adopt. Morphologies the Sink can adopt are similar. Importantly, the morphology of the Probe and the Sink may be different. Both the Probe and the Sink can comprises single Block or double Blocks, where a Block is either a strand or a complex that comprises 2 or more oligonucleotides formed through Watson-Crick hybridization reactions. The left panel shows the reaction between a Target and a single-Block Probe 4 that comprises a Target-binding Block (TB-Block). The right panel shows the reaction between a Target and a double-Block Probe 10 that comprises a Target-binding Block (TB-Block) and an Auxiliary Block (A-Block). The expended panel displaces exemplary structures of single-Block (5-9) and double-Block Probes (11-15). The black dots between strands represent base pairs within each Block, while the vertical black lines represent base pairs between Blocks and between the Target-binding Block and the bound Target (TProbe). The thick black portions of the Probe represent the nucleotide(s) dependent on the polymorphic nucleotide(s) that differ between the Target and Variant species. The half-arrow at one end of each strand represents the 3' end.

There components of the Competitive Composition comprise a target nucleic acid probe (Probe), a variant nucleic acid probe (Sink), and a target auxiliary oligonucleotide and a target auxiliary oligonucleotide. Both the Probe and Sink can comprise single or double Blocks, where a Block is either a strand or a complex that comprises 2 or more oligonucleotides formed through Watson-Crick hybridization reactions. Single-Block Probe or Sink comprises Target-binding Block, while double-Block Probe or Sink further comprises an Auxiliary Block in addition to the Target-binding Block. The Auxiliary Block releases from the Target-binding Block concurrently with the hybridization of the Target or Variant. Each of these components is a nucleic acid molecule and can adopt any of a number of different morphologies (FIG. 2). Example single-Block embodiments of the Probe and the Sink include (but are not limited to) molecular beacons, hairpin probes, and triple-stem probe. Example double-Block embodiments of the Probe and the Sink include (but are not limited to) Yin-Yang probes, toehold probes, and X-probes.

Each of these designs generally possesses some degree of tunability in reaction favorability with their intended target (i.e. Target for Probe, Variant for Sink). For example, the standard free energy of hybridization ($\Delta G°_{rxn}$) can be modulated via the length of the single-stranded toehold regions for Yin-Yang probes, toehold probes, X-probes, and hairpin probes; the length of nonhomologous regions for toehold probes and X-probes. For single-stranded components (e.g. molecular beacons, hairpin probes, triple-stem probes), reaction favorability can be tuned via component concentration.

For purposes of illustrating one embodiment of the present disclosure, a particular exemplary Competitive Composition comprising an X-probe for the Probe and an toehold probe for the Sink will be described. It should be understood that this specific embodiment is to provide an example of the Competitive Composition, and is not meant to limit the Competitive Composition to this embodiment.

Figure 3:
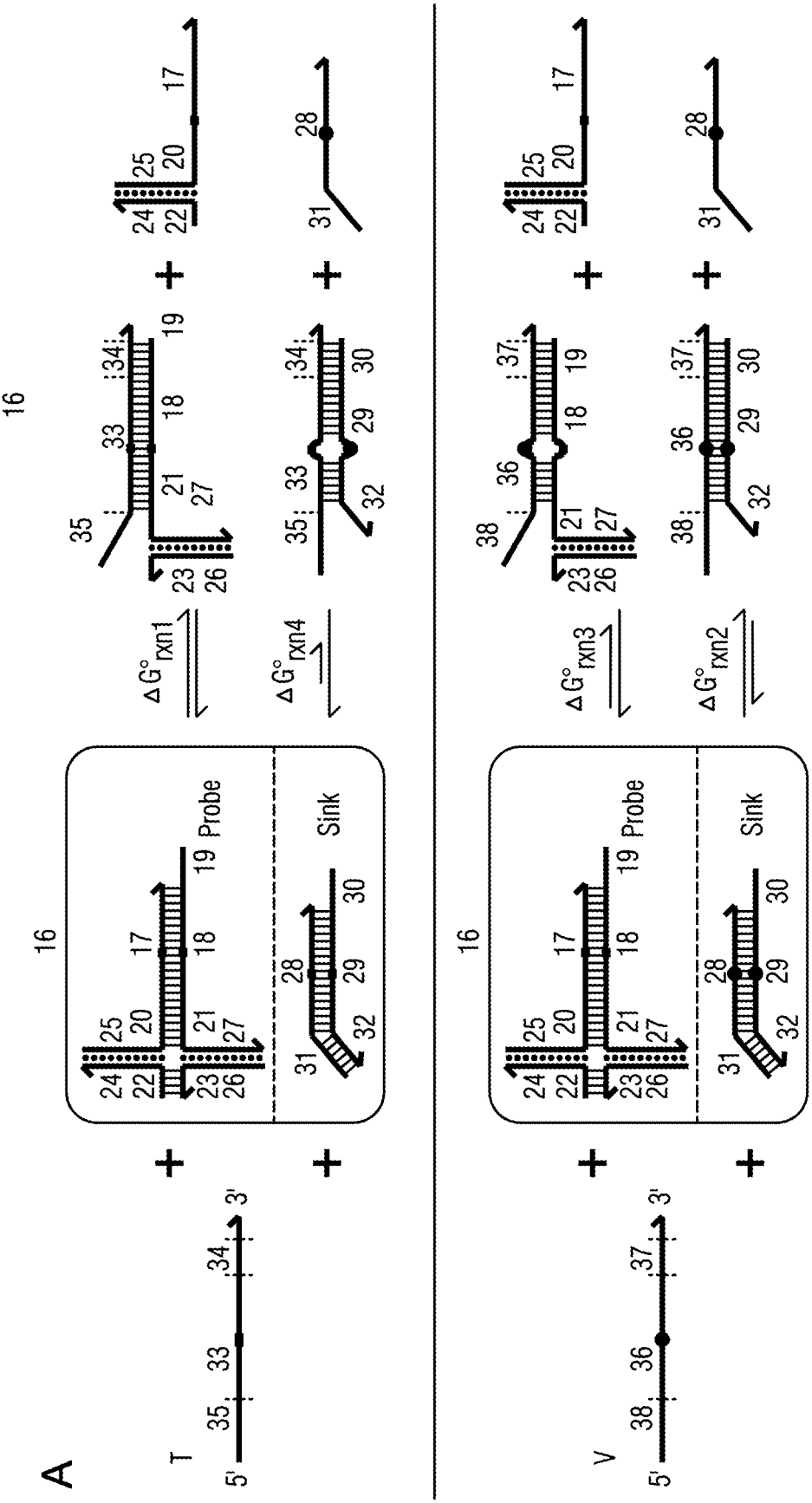
FIG. 3: Primary reactions between the Sample and an exemplary Competitive Composition 16. Here each oligonucleotide strand is subdivided into regions denoted by numbers. Each region comprises contiguous nucleotide bases, and acts as a functional unit in hybridization and disassociation. The four primary reactions are (1) the Target T binding to the Probe, (2) the Variant V binding to the Sink, (3) the Variant V binding to the Probe, and (4) the Target T binding to the Sink. Each of these reactions has a corresponding reaction standard free energy $\Delta G°_{rxn}$ that characterizes their favorability. The first two reactions are desirable reactions that properly pair the Target to the Probe and the Variant to the Sink, and the latter two reactions are undesirable.

As shown in FIG. 3, for example, in one embodiment, the target nucleic acid probe (Probe) is an X-probe and the non-target nucleic acid probe (Sink) is a toehold probe. Here, the X-probe (Probe) comprises four oligonucleotides or strands as follows: the first target oligonucleotide comprising subsequences 19, 18, 21, and 27; the second target oligonucleotide comprising subsequences 17, 20, and 25; the third oligonucleotide comprising subsequences 23 and 26; and the fourth oligonucleotide comprising subsequences 22 and 24. The first target nucleotide can be further characterized as including a target sequence region which is directed to subsequences 18 and 19 (and in some instances 20). It should also be noted that not all of the subsequences for each oligonucleotide are required for proper function. For example, subsequences 20-23 could be removed, or just subsequences 20 and 21 could be removed, or moreover, subsequences 22 and 23 could be removed. Each subsequence, represented by a number in FIG. 3, denotes a portion of the oligonucleotide that functionally acts as a unit in hybridization or dissociation. One subsequence is said to be complementary to another subsequence if the nucleotides of each subsequence can simultaneously form several Watson-Crick base pairs with each other. In this particular example, the first and second target oligonucleotides are designed such that subsequence 17 is partially or fully complementary to subsequence 18 thereby forming a first double-stranded region of the probe; optional subsequence 20 is partially or fully complementary to region 21 thereby forming a second double-stranded region of the probe (or simply an extension of the first double-stranded region); subsequence 26 is partially or fully complementary to region 27 thereby forming a third double-stranded region of the probe; optional subsequence 22 is partially or fully complementary to region 23 thereby forming a fourth double-stranded region of the probe; and subsequence 24 is partially or fully complementary to region 25 thereby forming a fifth double-stranded region of the probe. In addition, the first target oligonucleotide comprises a single-stranded region comprising subsequence 19 that is complementary to the target nucleic acid sequence (as is subsequence 18). Although not depicted in FIG. 3, subsequences 22 and 23 (or optionally subsequence 26 and 24 in the instance the probe is not designed with subsequences 22 and 23) provide sites for conjugation of detectable labels and quenchers thereof.

As the X-probe is introduced into a sample containing target T and under the proper temperature and buffer conditions as shown in FIG. 3, subsequences 18 and 19 of the first target oligonucleotide hybridize to subsequences 33 and 34, respectively, of the target T. Upon such hybridization, the third oligonucleotide bearing subsequence 26 will remain hybridized to subsequence 27 of the first target oligonucleotide ("target complex") whereas second target oligonucleotide and forth oligonucleotide (the "protector complex") will dissociate from the target complex. In the instance a fluorophore F is conjugated to the end of second oligonucleotide at subsequence 23 and a quencher Q is conjugated to the of the fourth oligonucleotide at subsequence 22, the dissociation of the protector complex from the target complex upon binding to the target will remove the quencher Q and allow the fluorophore F to fluoresce as the third oligonucleotide remains hybridized to subsequence 27 of the first target oligonucleotide.

Continuing with FIG. 3, in one embodiment, the Sink comprises a toehold or ultra-specific probe. The Sink comprises a first non-target oligonucleotide comprising subsequences 32, 29, and 30, and a second non-target oligonucleotide comprising subsequences 28 and 31. As can be appreciated in FIG. 3, the sink forms at least a first double-stranded region resulting from the hybridization of subsequences 28 and 29 and a second double-stranded region resulting from the hybridization of subsequences 31 and 32. This leaves the first non-target oligonucleotide having a single-stranded region of subsequence 30. Upon exposure to a sample comprising the target T and non-target nucleic acid variant V, subsequences 29 and 30 will hybridize to subsequences 36 and 37, respectively of variant V thereby causing release of the second non-target oligonucleotide from the probe complex. As discussed above, the Sink can comprise a label on the first non-target oligonucleotide and a quencher on the second non-target nucleotide at the end of subsequences 32 and 31, respectively. In this instance, the label will become detectable upon the first non-target oligonucleotide binding to variant V as the second non-target oligonucleotide bearing the quencher is displaced.

Although not shown in FIG. 3, the composition may comprise a target auxiliary oligonucleotide and a non-target auxiliary oligonucleotide. The target auxiliary oligonucleotide, in certain embodiments, comprises the second target oligonucleotide hybridized to the fourth oligonucleotide separate and free from the probe complex. Thus, the target auxiliary oligonucleotide or complex is in excess of the first target oligonucleotide and third oligonucleotide thereby resulting in an initial concentration of free first target oligonucleotide complexed with the third oligonucleotide. Similarly, the non-target auxiliary oligonucleotide, in this embodiment, comprises the second non-target oligonucleotide separate and free from the Sink probe complex. Stated another way, the second non-target oligonucleotide will be in excess of the first non-target oligonucleotide.

In another embodiment, the target nucleic acid probe of the competitive composition may comprise a toehold probe instead of a X-probe, and the non-target nucleic acid probe or Sink probe may comprise a toehold probe or an X-probe. In yet another embodiment, the target nucleic acid probe may comprise a toehold probe or an X probe and the non-target nucleic acid probe or Sink probe may comprise a single oligonucleotide. In yet another embodiment, the target nucleic acid probe may comprise a single oligonucleotide and the Sink probe may comprise either a toehold probe or a X-probe.

As explained in more detail below, based on its sequence, the target nucleic acid probe (Probe) has a target reaction standard free energy with the target nucleic acid sequence T defined as $\Delta G°_{rxn1}$, whereas the reaction of the Probe with the variant or non-target nucleic acid strand V will have a reaction standard free energy $\Delta G°_{rxn3}$ that will be weaker (more positive or less negative) than $\Delta G°_{rxn1}$ due to the mismatch base. Moreover, the Sink will act in the opposite fashion where its reaction standard free energy with the target ($\Delta G°_{rxn4}$) will be weaker that its reaction standard free energy with the variant ($\Delta G°_{rxn2}$) due to the mismatch base in the target T. Moreover, in certain embodiments, $\Delta G°_{rxn1}$ will be weaker (more positive or less negative) then $\Delta G°_{rxn2}$. More specifically, in certain embodiments, the relationship between $\Delta G°_{rxn1}$ and $\Delta G°_{rxn2}$ can be defined as, for example, $\Delta G°_{rxn1}$ is greater than the sum of $\Delta G°_{rxn2}+1$ kcal/mol, or alternatively $\Delta G°_{rxn1}$ is greater than $\Delta G°_{rxn2}$ where $\Delta G°_{rxn2}$ is greater than −7 kcal/mol. As used herein, the term "greater than" as used in connection with the standard reaction free energies of the Probe to target T and Sink to variant V means more positive or less negative (e.g. −4 kcal/mol is "greater than" −7 kcal/mol). Thus, in many instances, the composition of the present disclosure comprises a target nucleic acid probe that interacts with the target nucleic acid T less favorably than the non-target nucleic acid probe (Sink) interacts with the non-target nucleic acid variant V. In most samples in which the competitive compositions described above will be used, the non-target nucleic acid species or variant V is present on the dominant allele and will therefore be in excess of the target nucleic acid species T present on the rare allele.

In any of the above embodiments, any one of the strands of the probe may further comprise a synthetic nucleic acid analog such as LNA, PNA, 2′O-methyl substituted RNA, L-DNA, and speigelmers. In an alternative, any one of the strands of the probe may further comprise synthetic or natural analogs such as isosine, methylated nucleotides, iso-cytosine and iso-guanine, spiegelmer nucleotides, and xDNA.

The terms "polynucleotide," "nucleic acid," "oligonucleotide," "nucleic acid species," and "nucleic acid molecule" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component.

A process for preparing an X-probe is provided. In one embodiment, the third oligonucleotide (A), the fourth oligonucleotide (B), the second target (or non-target) oligonucleotide (P), and the first target (or non-target) oligonucleotide (C) are mixed together in aqueous solution. In one embodiment, the concentration of the first target (or non-target) oligonucleotide C is in excess of the third oligonucleotide A, the concentration of the second target (or non-target) oligonucleotide (P) is in excess of the first target (or non-target) oligonucleotide (C), and the concentration of the fourth oligonucleotide (B) is in excess of the protector strand such that a probe mixture is formed comprising complex BPCA, complex BPC, complex BP, and strand B. In another embodiment, the concentration of P is in excess of B, the concentration of C is in excess of P, and the concentration of A is in excess of C such that a probe mixture formed comprises complex BPCA, complex PCA, complex CA, and strand A.

In any of the above embodiments, the probe components are thermally annealed following mixing. In one embodiment, the thermal annealing includes heating the mixture to a temperature no less than 65° C., and cooling to a temperature no higher than 45° C. In another embodiment, the thermal annealing includes heating the mixture to a temperature no less than 80° C., and cooling to a temperature no higher than 60° C. In yet another embodiment, the thermal annealing includes heating the mixture to a temperature no less than 95° C., and cooling to a temperature no higher than 75° C.

In an alternative embodiment, the probe components are isothermally annealed through addition of salt or high salinity solutions. In yet another embodiment, the probe components are isothermally annealed through removal or dilution of formamide or other denaturants.

The probes of the present disclosure can be used in a variety of assays including, but not limited to the following: specific DNA or RNA detection or quantitation via fluorescence; specific DNA or RNA imaging via fluorescence; specific DNA or RNA detection, quantitation, or imaging via chromagenic methods (e.g. haptenated probes, and subsequent antibody-based recruitment of horseradish peroxidase (HRP) or alkaline phosphate (AP).

Competitive Composition Reactions

FIG. 3 shows the target T, variant V, Probe, and Sink decomposed as a number of regions or subsequences, denoted by numbers. Each region is a number of continuous nucleotide bases that act as a unit in hybridization and dissociation. Regions may be partially or fully Watson-Crick complementary to other regions (e.g. region 17 to region 18), and different regions may possess identical sequences to each other (e.g. regions 34 and 37).

The Variant and the Target species are here assumed to differ only from each other by a single polymorphic nucleotide, shown as a thick black line segment or black circle. In this example, the polymorphic nucleotide resides in the 33 and 36 regions. Here, it was assumed that regions 18 and 29 differ in sequence only at the nucleotide complementary to the polymorphic nucleotide, and that regions 19 and 30 are identical in sequence. In actuality, this does not need to be the case: for example, the complements to polymorphic nucleotide could reside in region 2 of the Probe and in region 30 of the Sink that is to say, the positions in which the Probe binds the Target/Variant need not be the same as the positions in which the Sink binds the Variant/Target. Regions 35 and 38 on the Variant and Target in FIG. 3 are optional and may not exist for short Variant and Target. If they do exist, however, region 35 and 38 are specifically not complementary to regions 21 and 23 of the Probe and region 32 of the Sink. Four distinct primary reactions occur between the two pairs of species: (1) the Target with the Probe, (2) the Variant with the Sink, (3) the Variant with the Probe, and (4) the Target with the Sink. From the point of view of enriching the fraction of Target bound to the Probe, the first two reactions are desirable: reaction (1) is the proper binding of the Target to the Probe, and reaction (2) reduces the amount of Variant available to bind to the Probe. In contrast, the other two are undesirable; reaction (3) is the improper binding of Variant to the Probe, and reaction (4) reduces the amount of Target available to bind to the Probe. The standard free energies of the four reactions are defined as $\Delta G°_{rxn1}$, $\Delta°_{rxn2}$, $\Delta G°_{rxn3}$, $\Delta G°_{rxn4}$, respectively.

Hypothetically, it would be desirable for $\Delta G°_{rxn1}$ and $\Delta G°_{rxn2}$ to be as negative (favorable) as possible, and simultaneously $\Delta G°_{rxn3}$ and $\Delta G°_{rxn4}$ should be as positive (unfavorable) as possible. However, these values are necessarily coupled:

$$\Delta\Delta G°_1 = \Delta G°_{rxn3} - \Delta G°_{rxn1}$$

$$\Delta\Delta G°_2 = \Delta G°_{rxn4} - \Delta G°_{rxn2}$$

The values of $\Delta\Delta G°_1$ and $\Delta\Delta G°_2$, in turn, are influenced by the relative thermodynamics of a single-base mismatch (in general, $\Delta\Delta G°_1 \neq \Delta\Delta G°_2$). Based on experimental data and analysis, it has been determined that optimal values of $\Delta G°_{rxn1}$ and $\Delta G°_{rxn2}$ depend to some degree on $\Delta\Delta G°$ values.

Figure 4A:
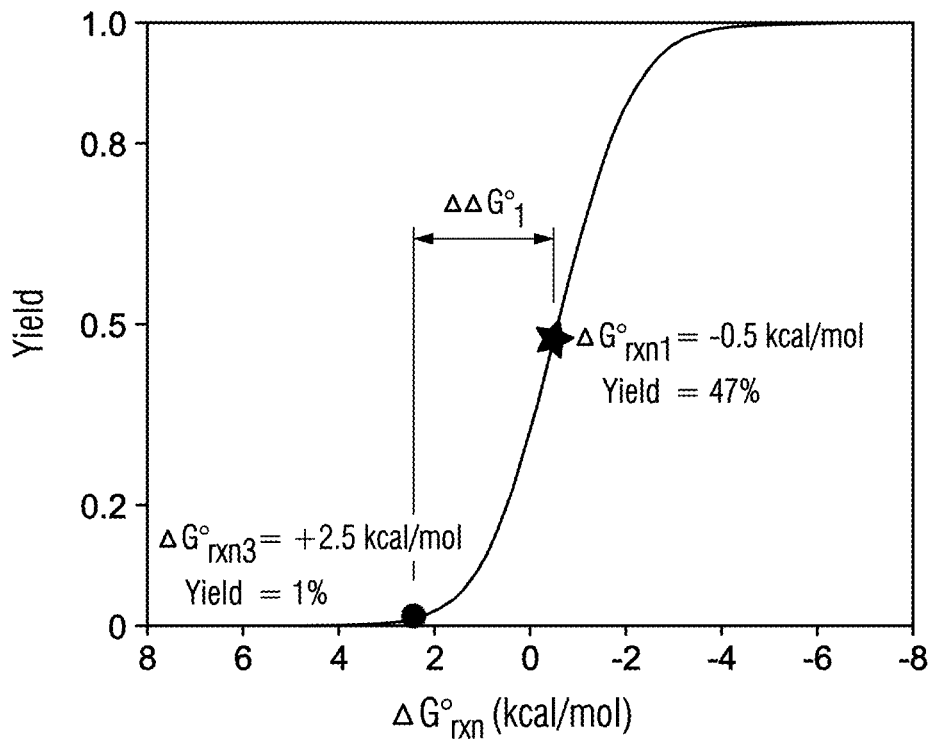
FIG. 4A: depicts reaction equilibrium behavior of the Probe and Sink at a first reaction standard free energy value. The analytical dependence of the equilibrium binding yield to the Probe (assuming excess Probe) on reaction $\Delta G°_{rxn}$ is shown, as well as the yields for $\Delta G°_{rxn1}=-0.5$ kcal/mol and $\Delta G°_{rxn3}=+2.5$ kcal/mol, corresponding to a $\Delta\Delta G°_1$ of 3.0 kcal/mol. There is an almost 50-fold difference in binding yield between the Target and the Variant to the Probe for these values.
Figure 4B:
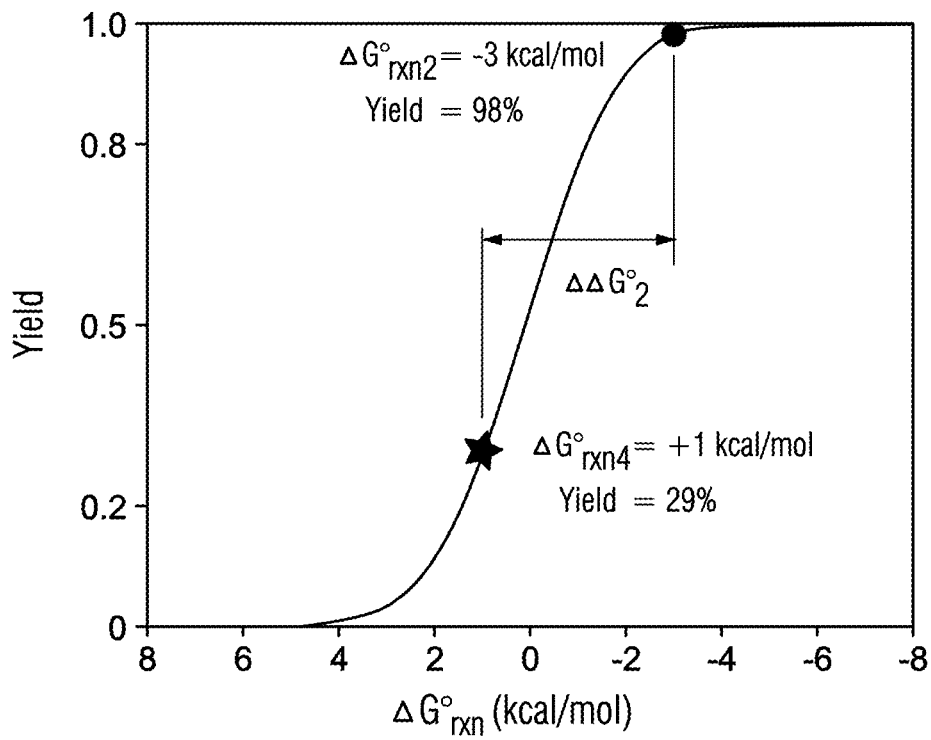
FIG. 4B depicts reaction equilibrium behavior of the Probe and Sink at a second reaction standard free energy value different from that in FIG. 4A. The analytical dependence of the equilibrium binding yield to the Sink based on reaction $\Delta G°_{rxn}$ follows a sigmoid. Because the intent of the Sink is to deplete the Variant concentration without too much impact on the Target concentration, a different set of $\Delta G°_{rxn}$ values are desirable than for the Probe. Here, $\Delta G°_{rxn2}=-3$ kcal/mol and $\Delta G°_{rxn4}=+1$ kcal/mol, resulting in 98% depletion of Variant (2% remaining) and 29% depletion of the Target (71% remaining). This set of values would improve the enrichment factor by over 30-fold (71%/2%).

One way to conceptualize the coupling between the different $\Delta G°_{rxn}$ terms and their effects on the Competitive Composition performance is to consider the equilibrium for each of the Probe's and the Sink's individual reactions with the Target and the Variant. In such a simplified scenario, each reaction yield (defined as the fraction of the Target or Variant that is hybridized to the Probe or Sink at equilibrium) can be analytically computed based on the value of $\Delta G°_{rxn}$ (FIGS. 4A and 4B). When there exists a large excess of Variant over Target, it is desirable from the point of view of enrichment for the Probe to possess higher specificity while the Sink possesses higher sensitivity.

Design Principles

The values of $\Delta\Delta G°_1$ and $\Delta\Delta G°_2$ are influenced by the single-base mismatch bubbles generated between the Variant-Probe complex (V•Probe) and the Target-Sink complex (T•Sink), respectively. Larger values of these two terms offer greater potential enrichment, but this potential can only be tapped via proper design of Probe and Sink with optimized $\Delta G°_{rxn1}$ and $\Delta G°_{rxn2}$ values.

Referring back to FIG. 3 and FIGS. 4A and 4B, an important tradeoff between specificity and sensitivity needs to be considered. For example, maximization of only the enrichment factor (X/Y), a proxy for the specificity, results from values of $\Delta G°_{rxn1}$ and $\Delta G°_{rxn2}$ being $\sim\infty$ and $-\infty$, respectively; unfortunately, such a Competitive Composition design would give no yield of either the Target or Variant bound to the Probe. Such a result is clearly undesirable from an application perspective of rare allele detection, quantitation, imaging, and purification, as this Competitive Composition would have zero sensitivity to the Target.

To explore these tradeoffs in realistic settings, the conditionally fluorescent X-Probe was considered as a model application for Target detection. The Binding affinity fold-change $\beta=(f_A \cdot X)/(f_B+f_C)$ represents the detectable fluorescence difference due to a small amount of the Target. Given the large number of species and reaction parameters in the Competitive Composition, analytical solution and optimization is unlikely to yield simple solutions conducive to intuitive understanding. Therefore, ordinary differential equation (ODE) simulations of the Competitive Composition system were performed in order to examine the landscape of Binding affinity fold-change due to various factors. The simulation follows the rate laws of chemical reaction and integrates the reaction process numerically.

For accuracy, modeled incidental species in the Probe and Sink components were also considered (FIG. 11). Additional investigations suggest these have very minor impact on the overall behavior of the system. The chemical reactions modeled are:

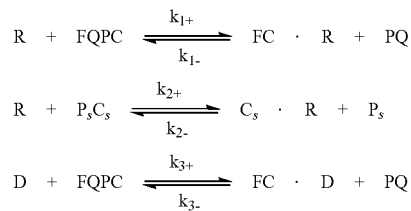

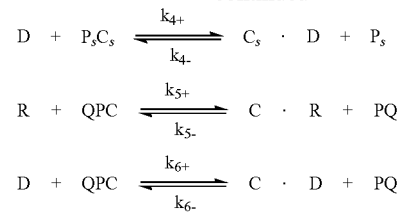

where R represents the Target, D represents the Variant, k+ and k− represent the forward and the reverse rate constants respectively. The names and structures of other species are illustrated in FIG. 11. The values of all forward reaction rate constants k+ are assumed to be $3\times10^5$ $M^{-1}s^{-1}$; this is estimated based on previous studies and our own calibration experiments (data not shown). The values of the reverse reaction rate constants k− are calculated based on $k_+$ on the $\Delta G°$ of the reaction:

$$k_- = \frac{k_+}{K_{eq}} = \frac{k_+}{e^{-\Delta G°_{rxn}/RT}}$$

For $k_{1-}$, $\Delta G°_{rxn1}$ was used; for $k_{2-}$, $\Delta G°_{rxn2}$, for $k_{3-}$, $\Delta G°_{rxn3} \equiv \Delta G°_{rxn1} + \Delta\Delta G°_1$; for $k_{4-}$, $\Delta G°_{rxn4} \equiv \Delta G°_{rxn2} + \Delta\Delta G°_2$; for $k_{5-}$, $\Delta G°_{rxn5} \equiv \Delta G°_{rxn1} + \Delta G°_{NH}$; for $k_{6-}$, $\Delta G°_{rxn6} \equiv \Delta G°_{rxn1} + \Delta\Delta G°_1 + \Delta G°_{NH}$. The term $\Delta G°_{NH}$ denotes the nonhomologous region that is missing for the incomplete QPC species of the Probe, and has value −8.46 kcal/mol. For all simulations here, $\Delta\Delta G°_1 = +3$ kcal/mol and $\Delta\Delta G°_2 = +4$ kcal/mol. The ODE simulation of the above reactions consists of the following rate law equations:

$$\frac{d[R]}{dt} = -k_{1+}[FQPC][R] + k_{1-}[FC \cdot R][PQ] -$$
$$k_{2+}[P_sC_s][R] + k_{2-}[C_s \cdot R][P_s] - k_{5+}[QPC][R] + k_{5-}[C \cdot R][PQ]$$

$$\frac{d[D]}{dt} = -k_{3+}[FQPC][D] + k_{3-}[FC \cdot D][PQ] - k_{4+}[P_sC_s][D] +$$
$$k_{4-}[C_s \cdot D][P_s] - k_{6+}[QPC][D] + k_{6-}[C \cdot D][PQ]$$

$$\frac{d[PQ]}{dt} = k_{1+}[FQPC][R] - k_{1-}[FC \cdot R][PQ] +$$
$$k_{3+}[FQPC][D] - k_{3-}[FC \cdot D][PQ] + k_{5+}[QPC][R] -$$
$$k_{5-}[C \cdot R][PQ] + k_{6+}[QPC][D] - k_{6-}[C \cdot D][PQ]$$

$$\frac{d[FQPC]}{dt} = -k_{1+}[FQPC][R] + k_{1-}[FC \cdot R][PQ] -$$
$$k_{3+}[FQPC][D] + k_{3-}[FC \cdot D][PQ]$$

$$\frac{d[P_s]}{dt} = k_{2+}[P_sC_s][R] - k_{2-}[C_s \cdot R][P_s] + k_{4+}[P_sC_s][D] - k_{4-}[C_s \cdot D][P_s]$$

$$\frac{d[P_sC_s]}{dt} =$$
$$-k_{2+}[P_sC_s][R] - k_{2-}[C_s \cdot R][P_s] - k_{4+}[P_sC_s][D] + k_{4-}[C_s \cdot D][P_s]$$

$$\frac{d[FC \cdot R]}{dt} = k_{1+}[FQPC][R] - k_{1-}[FC \cdot R][PQ]$$

$$\frac{d[FC \cdot D]}{dt} = k_{3+}[FQPC][D] - k_{3-}[FC \cdot D][PQ]$$

$$\frac{d[C_s \cdot R]}{dt} = k_{2+}[P_sC_s][R] - k_{2-}[C_s \cdot R][P_s]$$

$$\frac{d[C_s \cdot D]}{dt} = k_{4+}[P_sC_s][D] - k_{4-}[C_s \cdot D][P_s]$$

-continued $$\frac{d[QPC]}{dt} = -k_{5+}[QPC][R] + k_{5-}[C \cdot R][PQ] - k_{6+}[QPC][D] + k_{6-}[C \cdot D][PQ]$$

$$\frac{d[C \cdot R]}{dt} = k_{5+}[QPC][R] - k_{5-}[C \cdot R][PQ]$$

$$\frac{d[C \cdot D]}{dt} = k_{6+}[QPC][D] - k_{6-}[C \cdot D][PQ]$$

Figure 12A:
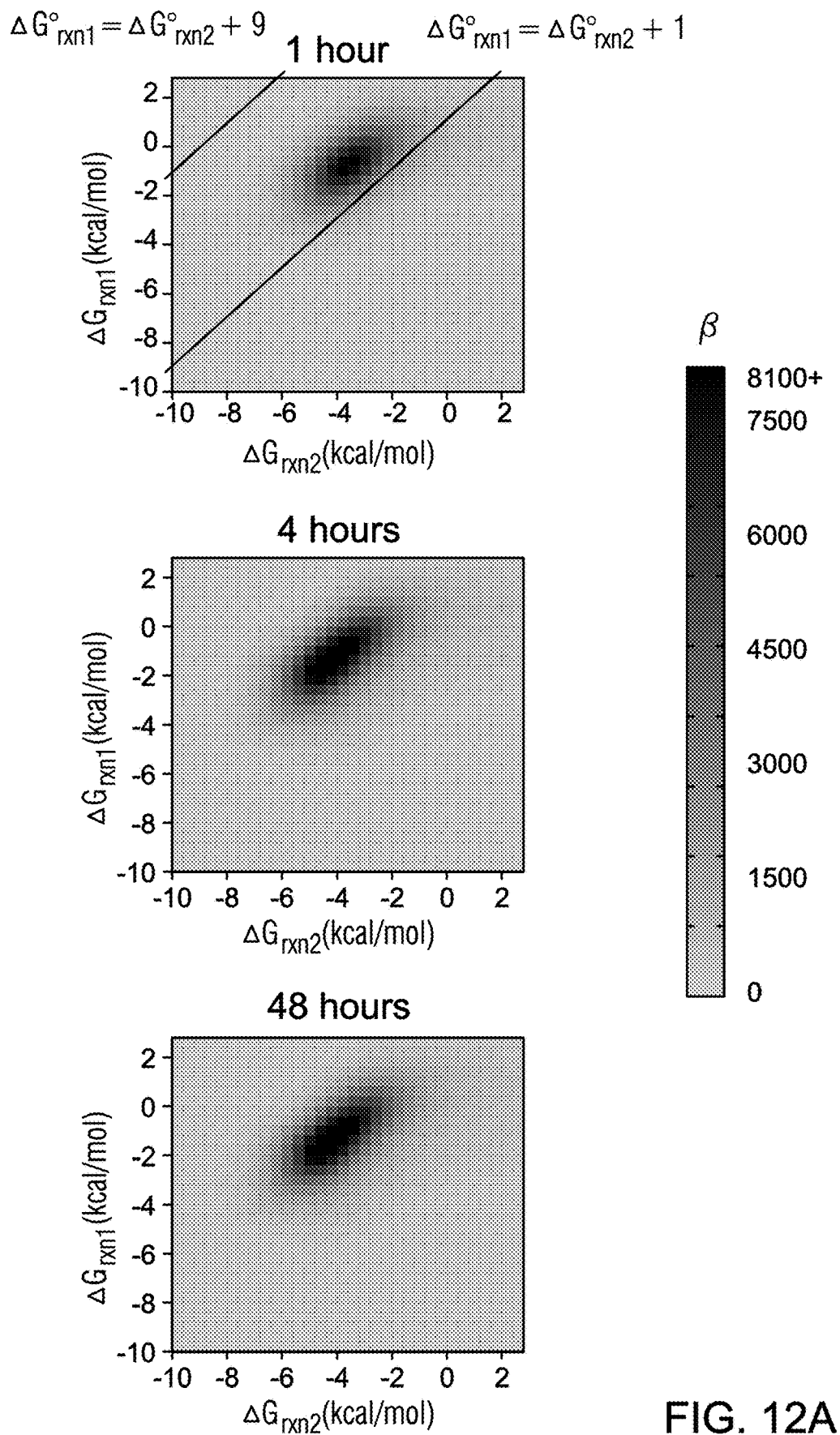
FIG. 12A provides simulations of the Competitive Composition reacting with a low fraction (0.01%) of Target. These simulations are performed based on the Ordinary Differential Equation model described in the text of the example conditionally fluorescent system. Shown are binding affinity fold-change β due to the low quantity of Target after 1 hour of reaction, 4 hours of reaction, and 48 hours of reaction, due to varying values of $\Delta G°_{rxn1}$ and $\Delta G°_{rxn2}$. Longer reaction times broaden the range of $\Delta G°_{rxn}$ values that yield high β.
Figure 12B:
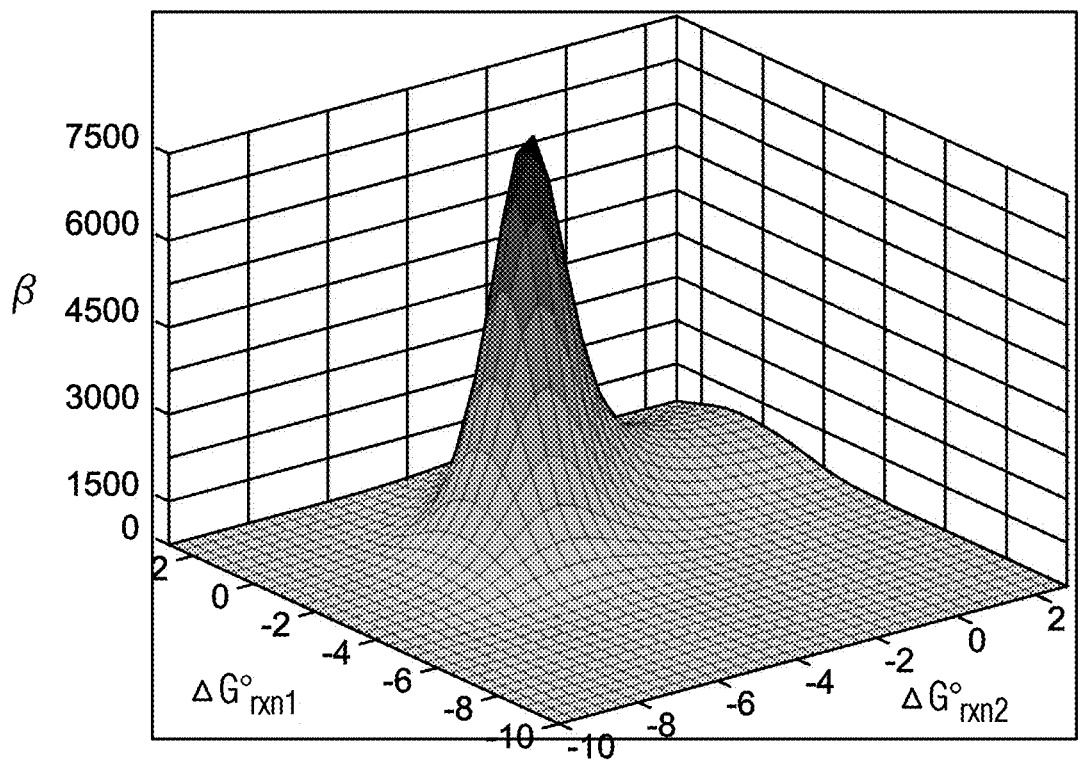
FIG. 12B provides a three-dimensional representation of the β value shown in FIG. 12A based on $\Delta G°_{rxn1}$ and $\Delta G°_{rxn2}$ after 1 hour of reaction.

FIG. 12 shows summary simulation results for the Competitive Composition system. For these simulations, the initial concentration of species were [Target]=0.15 nM, [Variant]=1500 nM, [FQPC]=2.5 nM, [QPC]=1.25 nM, [QP]=3.75 nM, [$P_SC_S$]=2250 nM, and [$P_S$]=450 nM. The background fluorescence $f_B$ is equivalent to the fluorescence from 0.04 nM of unquenched fluorophore-labeled strands, and is consistent with observed values in experiments (FIG. 6-9).

There is an optimal value range for $\Delta G°_{rxn1}$ and $\Delta G°_{rxn2}$ that yields high Binding affinity fold-change (FIG. 12AB). When the longer reaction times are allowed, the range of desirable $\Delta G°_{rxn1}$ and $\Delta G°_{rxn2}$ values broadens slightly: For example, after 1 hour of reaction, Signal Increase is high when $\Delta G°_{rxn1}$ is between 0 and −1.5 kcal/mol and $\Delta G°_{rxn2}$ is between −2.5 and −4.5 kcal/mol. After 48 hours, the range broadens to between 0 and −4.5 kcal/mol for $\Delta G°_{rxn1}$ and between −2.5 and −7 kcal/mol for $\Delta G°_{rxn2}$.

Figure 12C:
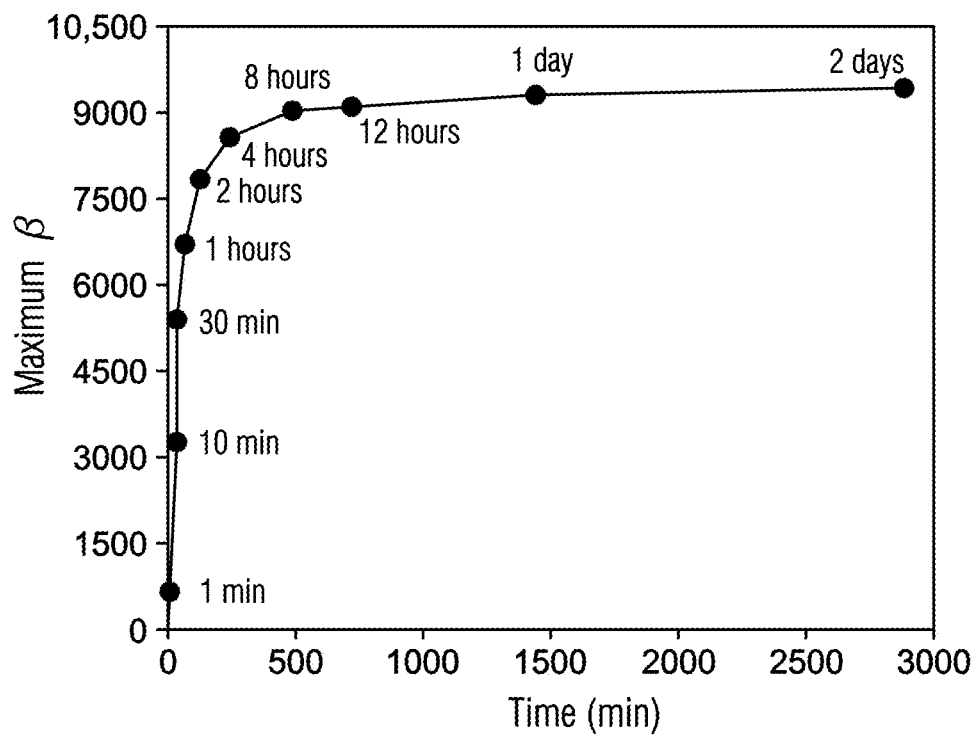
FIG. 12C demonstrates the maximum β value that can be achieved following different durations of reaction time based on the simulation of FIG. 12A.
Figure 13:
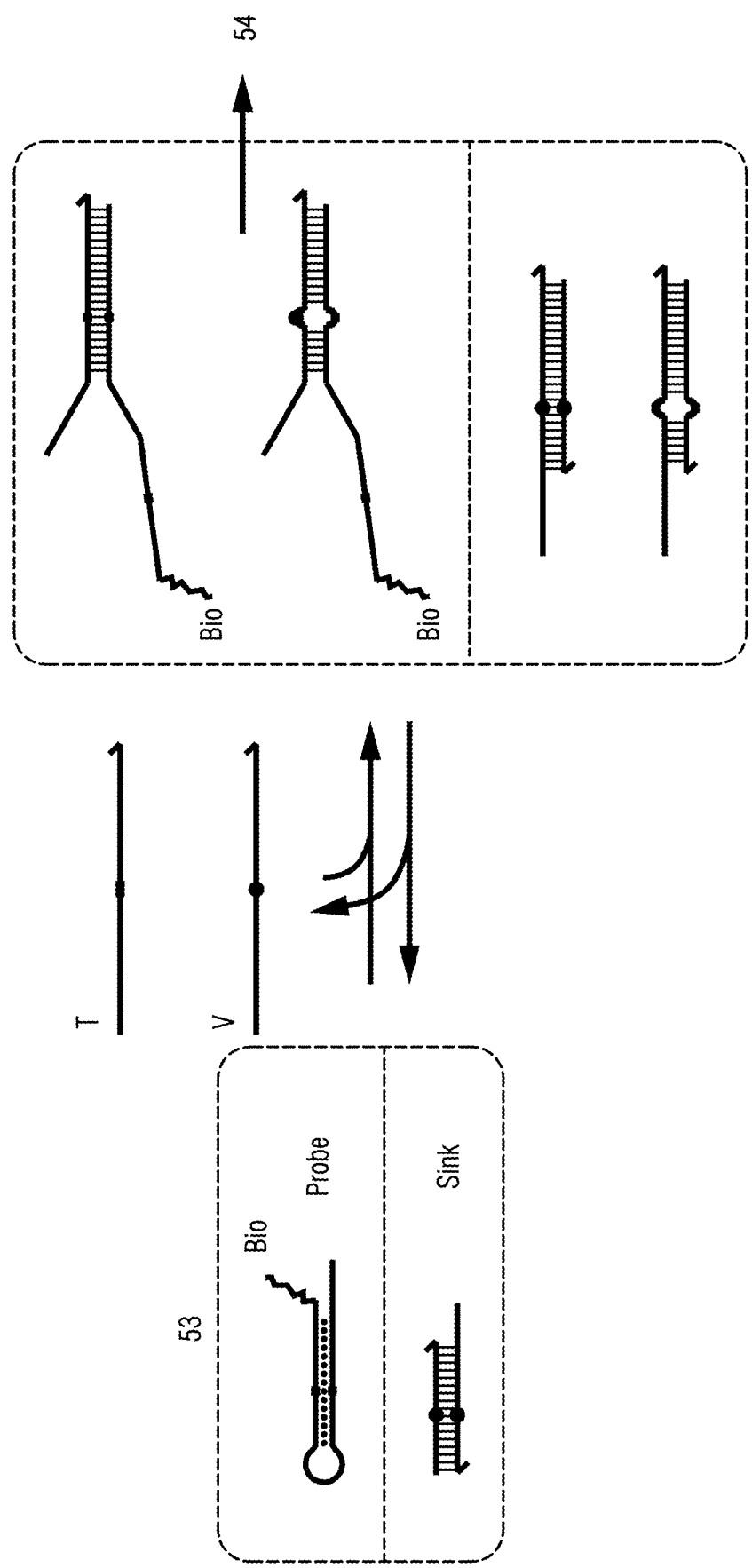
FIG. 13: Competitive composition 53 with different Probe and Sink component morphologies, here a biotin-functionalized (Bio) hairpin probe for the Probe and a Yin-Yang probe for the Sink. With the probes properly designed based on thermodynamics, the fraction of Target T to Variant V that will be captured by a streptavidin-coated surface 54 will be highly enriched over the original sample. Due to the single-stranded nature of the hairpin probe, there is an additional $R\tau \ln([\text{Probe}])$ term in the evaluation of optimal $\Delta G°_{rxn1}$. The black dots between strands represent base pairs within each Block, while the vertical black lines represent base pairs between Blocks and between the Target-binding Block and the bound Target or Variant.

Furthermore, FIG. 12C shows that the maximum signal increase achievable increases with reaction time, though improvement becomes marginal after about 4 hours. In many applications, rapid assays and reactions are desirable; thus there is a tradeoff between short and long reaction times. It is expected that between 30 minutes and 4 hours will be typical.

In the above simulations, $\Delta\Delta G°_1$ and $\Delta\Delta G°_2$ were assumed to be +3 and +4 kcal/mol. Through the course of our simulations and investigations, it has been determined that the optimal $\Delta G°_{rxn1}$ and $\Delta G°_{rxn2}$ ranges are relatively insensitive to parameters such as Probe concentration [FQPC], Sink concentration [$P_SC_S$], reaction time, and background fluorescence level $f_B$. They are, however, sensitive to the stoichiometric ratios ([QP]/[FQPC]), ([$P_S$]/[$P_SC_S$]), and $\Delta\Delta G°$ values, consistent with prior art on double-stranded probes.

Consequently, the following ranges of $\Delta G°_{rxn}$ values are reasonable for this embodiment (X-Probe as Probe, ultra-specific probes as Sink) of Competitive Compositions:

−4 kcal/mol≤$\Delta G°_{rxn1}$+$R\tau$ ln([QP]/[FQPC])≤+3 kcal/mol

−7 kcal/mol≤$\Delta G°_{rxn2}$+$R\tau$ ln([$P_S$]/[$P_SC_S$])≤+1 kcal/mol   (1)

where R is the ideal gas constant and is the temperature in Kelvin, and concentrations shown are initial concentrations before addition of sample. As can be seen, high performance is generally observed when the Sink binds more favorably to the Variant than the Probe to the Target ($\Delta G°_{rxn1} < \Delta G°_{rxn2}$). Competitive Compositions utilizing other Probe and Sink morphologies that result in auxiliary species release follow the same range guidelines for $\Delta G°_{rxn}$ values. Use of Probe morphologies that do not release auxiliary species (e.g. molecular beacons, hairpin probes, and triple-stem probes instead follows:

−4 kcal/mol≤$\Delta G°_{rxn1}$−$R\tau$ ln([Probe])≤+3 kcal/mol   (2)

Similarly, use of Sink morphologies that do not release auxiliary species follows:

−7 kcal/mol≤$\Delta G°_{rxn2}$−$R\tau$ ln([Sink])≤+1 kcal/mol   (3)

The values of $\Delta G°_{rxn1}$ and $\Delta G°_{rxn2}$ for a given Probe and Sink design can be calculated using software such as NUPACK or mFold based on their sequences; such calculations are described in more detail in literature describing the component probes themselves and is considered accessible by people of ordinary skill in the art of thermodynamics-guided nucleic acid probe design. Simultaneous use of multiple Probes with different morphologies targeting the same Target species is not recommended; simultaneous use of multiple Sinks with different morphologies targeting the same Variant species is not recommended.

For example, the standard reaction free energy of the interaction between the target nucleic acid probe (Probe) and target nucleic acid T of FIG. 3 may be expressed as:

$$\Delta G°_{rxn1} = \Delta G°_{34-19} - \Delta G°_{22-23} - \Delta G°_{20-21} - \Delta G°_{ML} + (\Delta G°_{33-18} - \Delta G°_{17-18}) - \Delta G°_{label}$$

where $\Delta G°_{34-19}$ is the standard free energy of the hybridization between subsequence 34 and subsequence 19, $\Delta G°_{22-23}$ is the standard free energy of the hybridization between subsequence 22 and subsequence 23, $\Delta G°_{20-21}$ is the standard free energy of the hybridization between subsequence 20 and subsequence 21, $\Delta G°_{ML}$ is the standard free energy of the hybridization in the multi-loop provided at the intersection of the four oligonucleotides, $\Delta G°_{33-18}$ is the standard free energy of the hybridization between subsequence 33 and subsequence 18, $\Delta G°_{17-18}$ is the standard free energy of the hybridization between subsequence 17 and subsequence 18, and $\Delta G°_{label}$ is the standard free energy difference between the thermodynamic contribution of the label on the third oligonucleotide when it is in close proximity to the label on the fourth oligonucleotide (not shown) versus when they are delocalized.

Additionally, the standard reaction free energy of the interaction between the non-target nucleic acid probe (Sink) and non-target nucleic acid V of FIG. 3 may be expressed as:

$$\Delta G°_{rxn2} = \Delta G°_{t-TC} - \Delta G°_{nh-PC} + (\Delta G°_{v-TC} - \Delta G°_{h-PC})$$

where $\Delta G°_{t-TC}$ is the standard free energy of the hybridization between subsequence 37 and subsequence 30, $\Delta G°_{nh-PC}$ is the standard free energy of the hybridization between subsequence 31 and subsequence 32, $\Delta G°_{v-TC}$ is the standard free energy of the hybridization between subsequence 36 and subsequence 29, $\Delta G°_{h-PC}$ is the standard free energy of the hybridization between subsequence 28 and subsequence 29.

Finally, although Signal Increase is a metric specific to conditionally fluorescent Competitive Compositions for detection of Target, other applications that utilize the enrichment capabilities of the Competitive Composition, such as in situ hybridization-based imaging or enzyme-based amplification, likely also face a tradeoff between specificity and sensitivity, so that the guidelines for $\Delta G°_{rxn1}$ and $\Delta G°_{rxn2}$ are likely to be generally suitable.

Other Applications of Competitive Compositions

Figure 14:
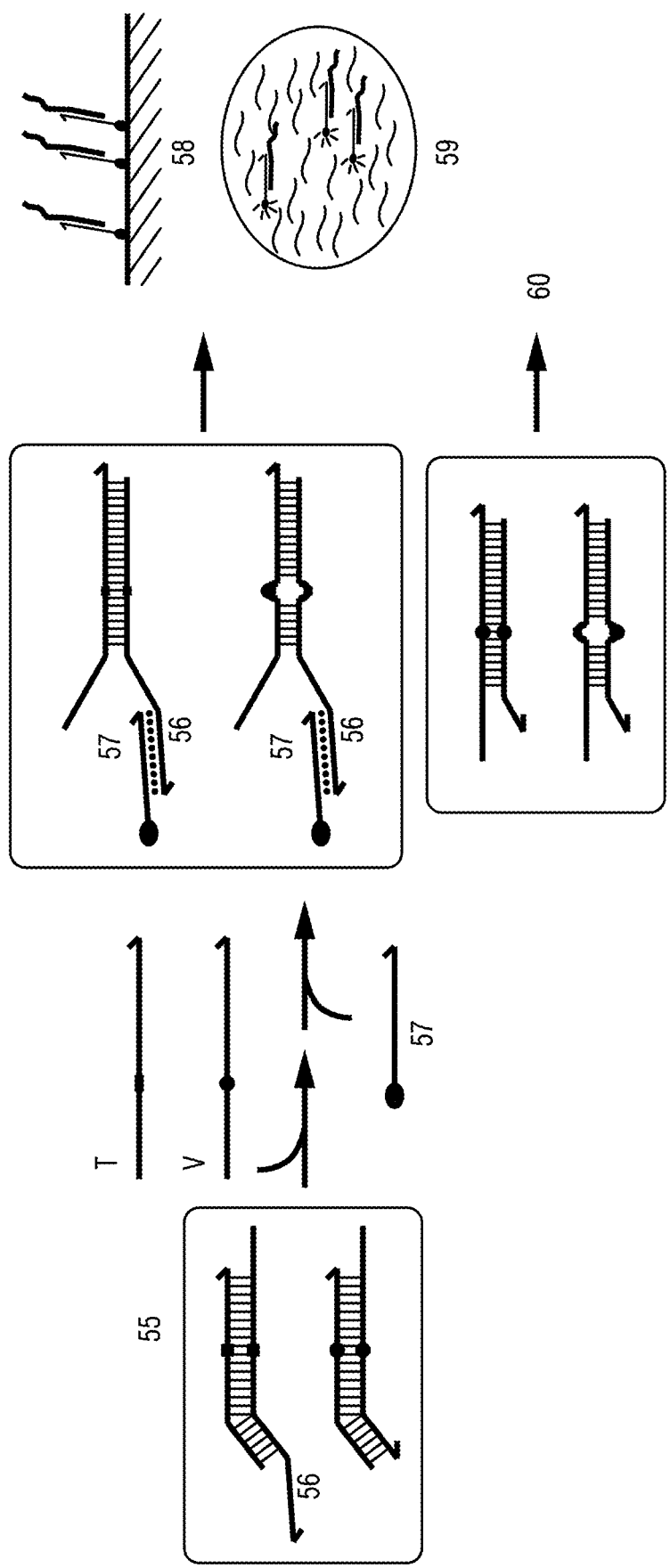
FIG. 14: Competitive Composition 55 with unfunctionalized Probe and Sink components. Instead the enrichment capabilities are realized via a functionalized nucleic acid molecule 57 of universal sequence that is complementary to an additional region of the Probe (region 56). The indirect linkage between the Probe and the functionalized oligonucleotide need not be through only one hybridization interaction: for example, the Probe could be hybridized partially to an unfunctionalized strand, which is itself hybridized partially to a secondary functionalized strand. The product that a colocalized with the functionalized group will simultaneously or sequentially be captured 58, imaged 59, or assayed through any other methods, while the rest of the molecules will usually be washed away 60.

Another example embodiment of Competitive Composition involves indirect linkage of the Probe species to a functionalized oligo (known as a Universal Functionalized Strand) via one or more hybridization interactions on additional domains (FIG. 14). The Target and Variant molecules that react with the Probe become colocalized to the Universal Functionalized Strand, which facilitates the enrichment of Target via surface or nanoparticle capture, or enables detection/imaging via direct or downstream fluorescence, metallic precipitation, or chemoluminescence. Target and Variant molecules not bound to the Probe, in some embodiments, are dark or washed away prior to downstream reaction.

Figure 15:
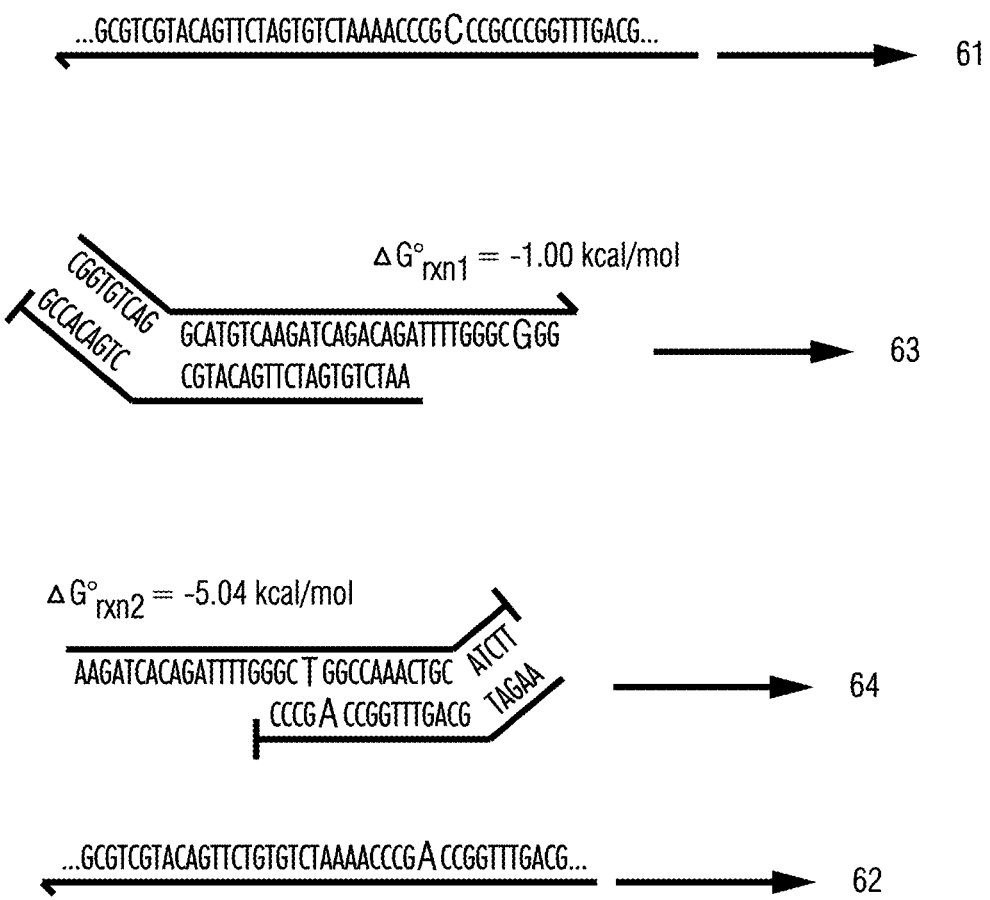
FIG. 15: Competitive Composition for enrichment of allele-specific enzymatic amplification. The Target and Variant species are based on the antisense strands for the EGFR L858R (c.2573T>G) mutation 61 and the corresponding wildtype sequence 62. Values of $\Delta G°_{rxn}$ shown are calculated at 60° C. in 0.18 M Na$^+$, consistent with the environment of a typical PCR anneal step. The Probe 63 is the only species that is not blocked at the 3' end by a non-extensible group, and capable of serving as primer. Thus, the enrichment of Target to Variant in binding to the Probe serves to increase the fraction of Target that is amplified by PCR.

Another example embodiment of Competitive Composition involves the usage of the Probe as a primer for enzymatic amplification (FIG. 15). The Target may be a biological sequence bearing a rare mutation or allele, and the Variant may represent the wildtype sequence. In this example, the 3' end of the Sink is functionalized with a chemical moiety that prevents enzymatic extension, such as a dideoxy nucleotide, a 3-carbon spacer group, or a minor groove binder.

Design Process

Many potential design processes can be used to generate the sequences employed in a Competitive Composition. The following provides one example.

1) Select the Target and Variant as subsequences from a target nucleic acid. The Target and Variant must contain the polymorphic nucleotide(s) of interest, and are otherwise identical. Considerations, such as Target and Variant secondary structure, can be used to inform Target and Variant sequence selection.

(2) Determine operation conditions, including temperature, buffer salinity, crowding/denaturing agents, reaction time, and readout mechanism.

(3) Select morphologies of the Probe and the Sink. Considerations, such as cost and complexity of the components, can be used to guide/inform morphology selection.

(4) Calculate or estimate $\Delta\Delta G°_1$ and $\Delta\Delta G°_2$ based on the Target and Variant sequences at desired operation conditions. Thermodynamic values for DNA-DNA and RNA-RNA mismatch bubbles for certain operation conditions are available in literature; for other nucleic acids or conditions, $\Delta\Delta G°$ values can only be coarsely estimated.

(5) Determine optimal values of $\Delta G°_{rxn1}$ and $\Delta G°_{rxn2}$ via ordinary differential equation simulations, such as described in this document. Binding affinity fold-change (or other relevant metric) will be calculated for many different $\Delta G°_{rxn}$ values based on $\Delta\Delta G°$ values, predetermined background signal, Target and Variant concentrations, and Probe and Sink concentrations.

(6) Design Target-specific Probe based on selected morphology and selected $\Delta G°_{rxn1}$ value, with iterative fine-tuning of sequence as necessary. Other considerations such as oligonucleotide lengths, functionalizations utilized, etc. can be used for further guide and inform Probe sequence selection.

(7) Design Variant-specific Sink based on selected morphology and selected $\Delta G°_{rxn2}$ value, with iterative fine-tuning of sequence as necessary. Other considerations such as oligonucleotide lengths, functionalizations utilized, etc. can be used for further guide and inform Sink sequence selection.

Examples

Experimental Results on Conditionally Fluorescent Competitive Compositions

Figure 5:
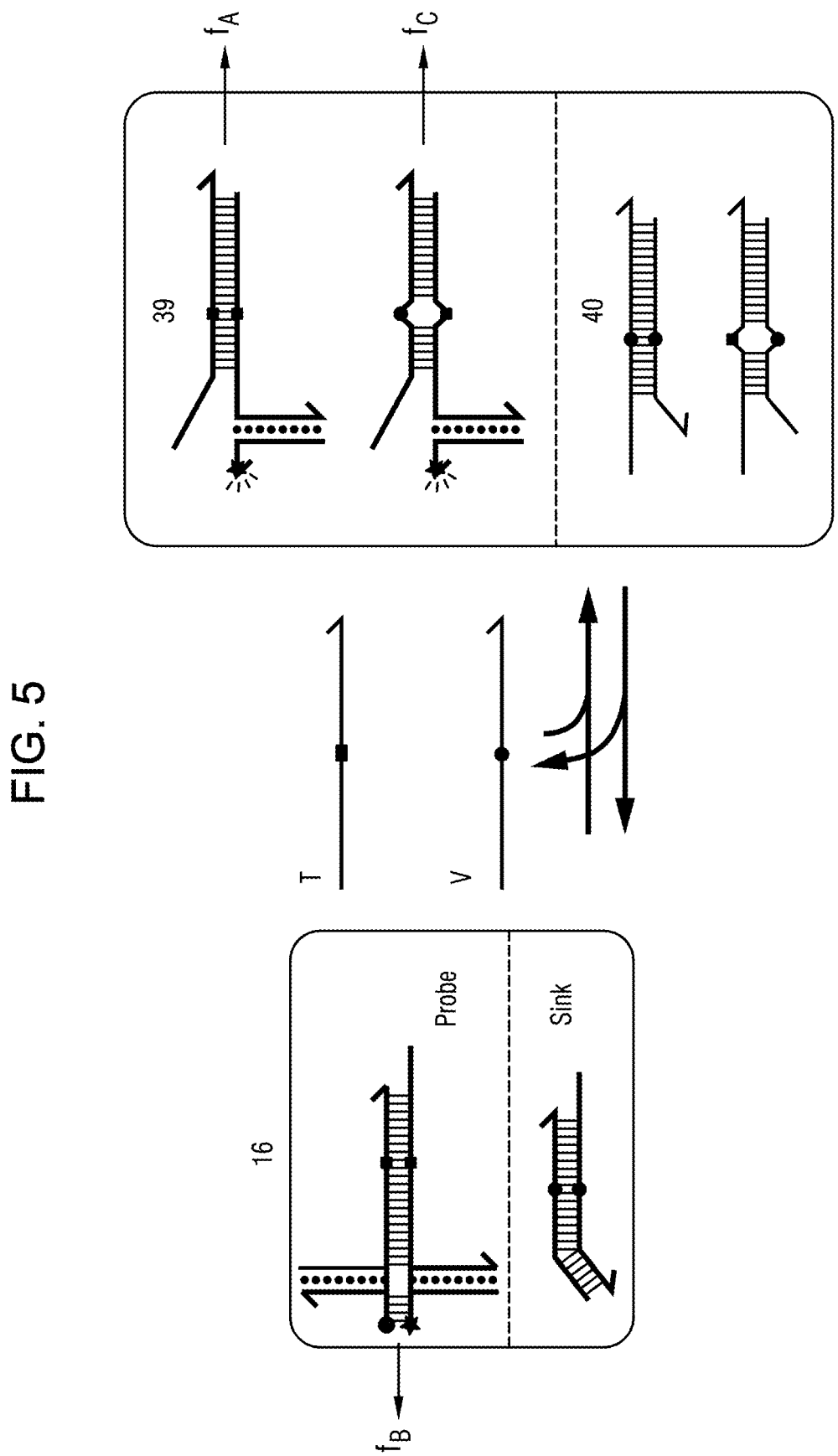
FIG. 5: An embodiment of Competitive Compositions 16 using an X-Probe as Probe and a toehold probe as Sink, in which the Probe exhibits conditional fluorescence upon hybridization to Target T or Variant V. Conditional fluorescence is achieved because a fluorophore (shown as star) is initially in close proximity to a quencher (shown as large dot); after reaction, the quencher is delocalized and fluorescence increases. There are three contributions to observed fluorescence: the fluorescence due to Target bound to the Probe ($f_A$), the fluorescence due to Variant bound to the Probe ($f_C$), and the fluorescence of the unbound Probe due to incomplete quenching ($f_B$).

To experimentally validate the ability for Competitive Compositions to enrich Target over Variant in binding to the probe, experiments were designed and performed on a conditionally fluorescent version of the Probe (FIG. 5). The Probe is natively dark until it hybridizes to either the Target or the Variant. By observing the fluorescence response of a sample of Variant with a small amount (load) of Target, and comparing to the response of the same quantity of Variant in absence of Target, it can be inferred that the enrichment is provided by the Competitive Composition.

Referring now to FIG. 5, four major products are formed via the reactions described in FIG. 3; of these, the two products involving the Probe yield high fluorescence. The fluorescence generated by the Target bound to the Probe is denoted by $f_A$, the fluorescence generated by the Variant bound to the Probe is denoted by $f_C$, and the total background fluorescence due to incomplete quenching, dark current of the photon detector, autofluorescence of the cuvettes and water Roman spectra is denoted by $f_B$.

Figure 6:
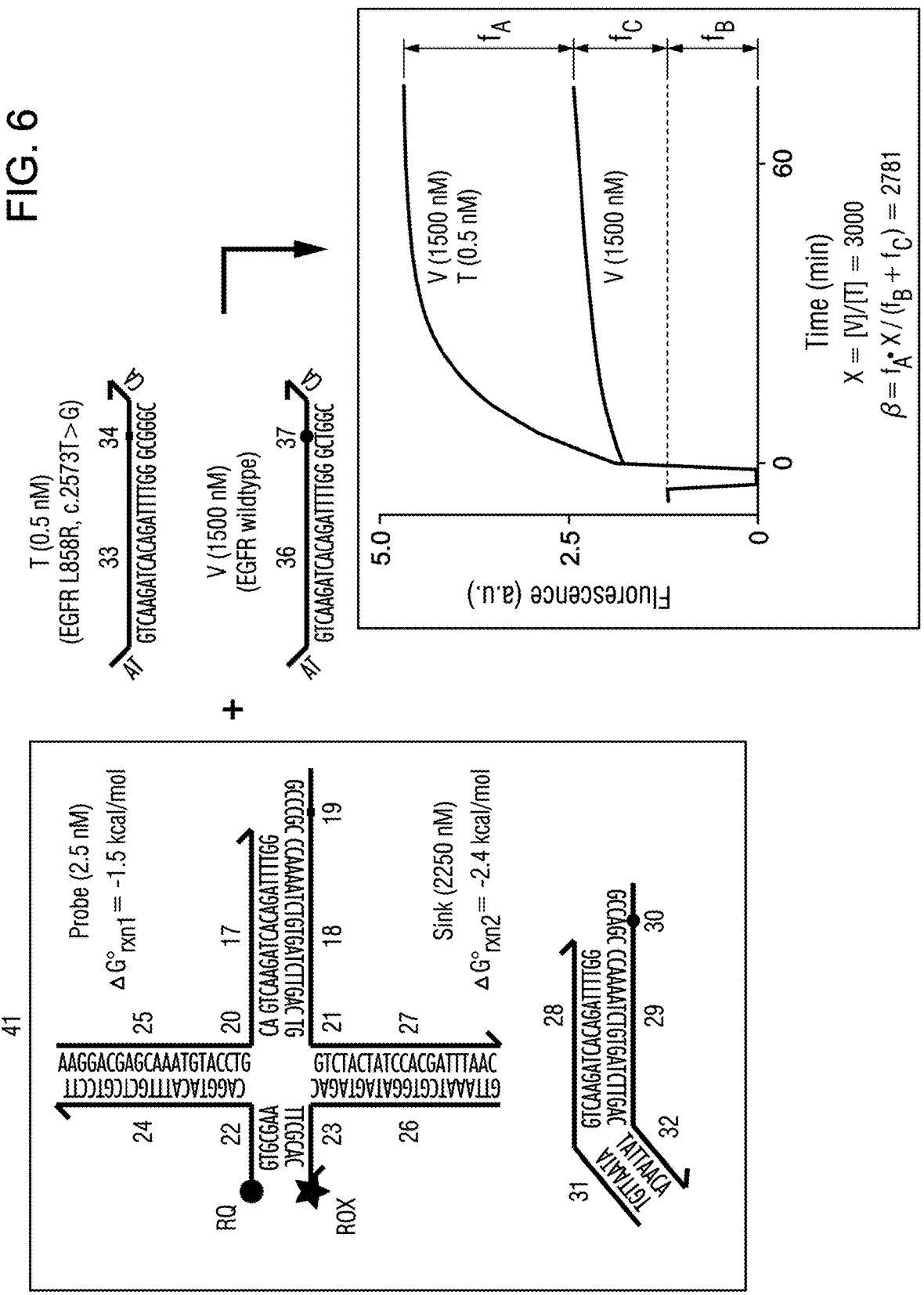
FIG. 6: Example Competitive Composition 41 (SEQ ID NOS 2, 45, 1, 46, 47 and 48, respectively, in order of appearance) for fluorescent detection of the rare EGFR L858R (c.2573T>G) mutation (T) (SEQ ID NO: 43) in a background of EGFR wildtype sequence (V) (SEQ ID NO: 44). The polymorphic nucleotide is shown in bold. The differential fluorescence responses of Variant alone (1500 nM) and Variant (1500 nM) with a small amount of Target (0.5 nM) are shown. The latter conditions correspond to X=3000-fold excess of Variant over Target, and comparison of $f_A$ and $f_C$ values suggest a 2781-fold binding affinity difference (as measured by β) of Target bound to Probe as compare to Variant bound to Probe. Experiments were performed at 37° C. in 5×PBS buffer using synthetic oligonucleotides of the given sequences.
Figure 8:
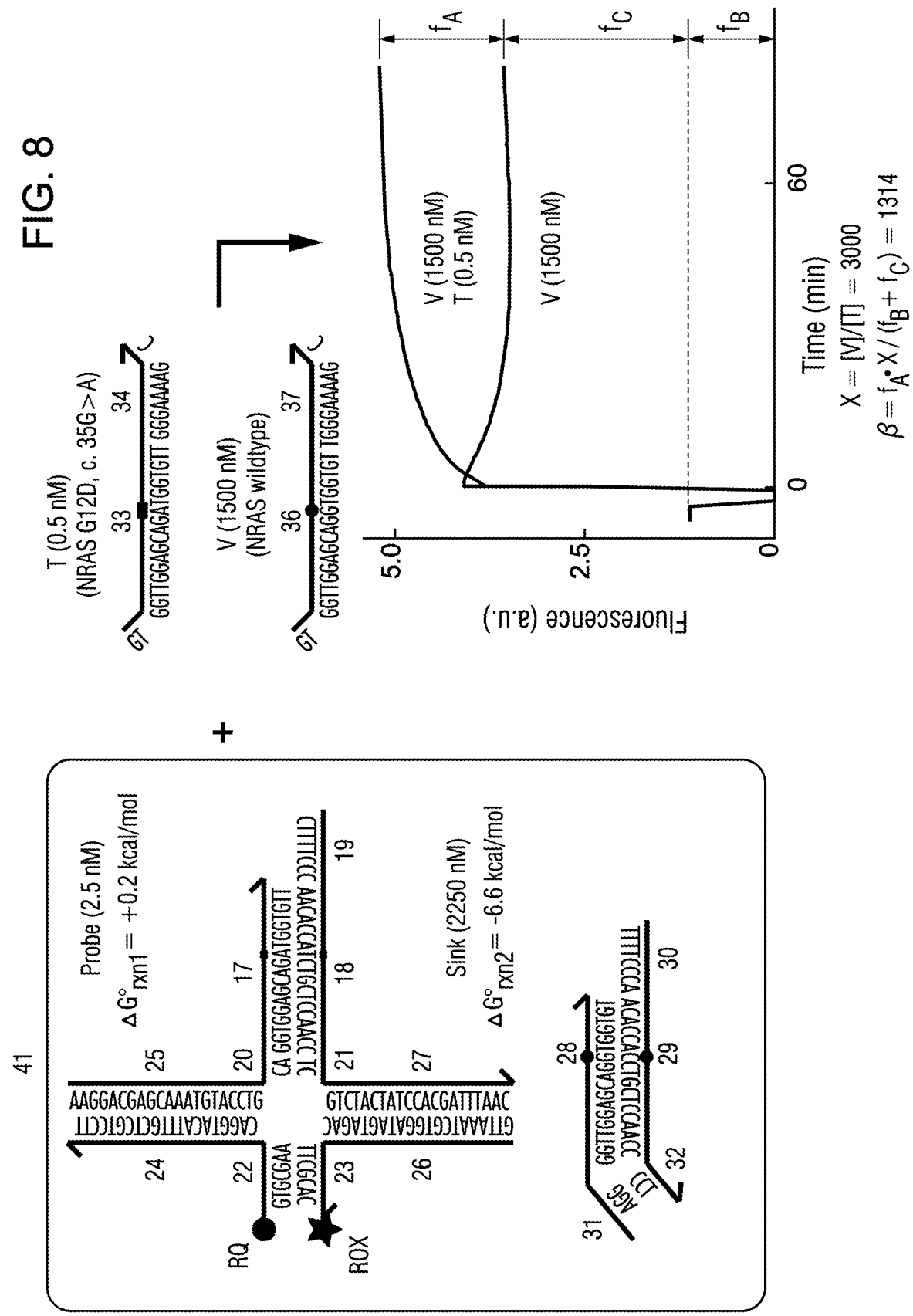
FIG. 8: Example Competitive Composition 43 (SEQ ID NOS 2, 147, 1, 148, 143 and 144, respectively, in order of appearance) for fluorescent detection of the rare NRAS G12D (c.35G>A) mutation (T) (SEQ ID NO: 145) in a background of NRAS wildtype sequence (V) (SEQ ID NO: 146). Experiments were performed at 37° C. in 5×PBS buffer using synthetic oligonucleotides of the given sequences.

FIG. 6-8 show the sequence designs for the Probe, Sink, Target, and Variant based on 3 different cancer-related mutation sequences, drawn from the COSMIC database. In each of these, the Variant is the wildtype gene sequence, and the Target is a single nucleotide variant; the concentration of Variant was 3000 times that of the concentration of Target in each case (X=3000), yet the 0.033% load of the Target contributed similar additional fluorescence signal as the Variant. This indicates that of the molecules bound to the Probe, the Target has been enriched by a factor of over 1000.

A different metric to utilize is "Binding affinity fold-change β", defined as $(f_A*X)/(f_B+f_C)$. Binding affinity fold-change is likely the most reproducible and robust metric because the background fluorescence level $f_B$ may vary due to autofluorescence from different cuvettes, or differences in sample holder positions, or other changes. A lower bound for the enrichment factor (X/Y) can be calculated as the Binding affinity fold-change.

Figure 9A:
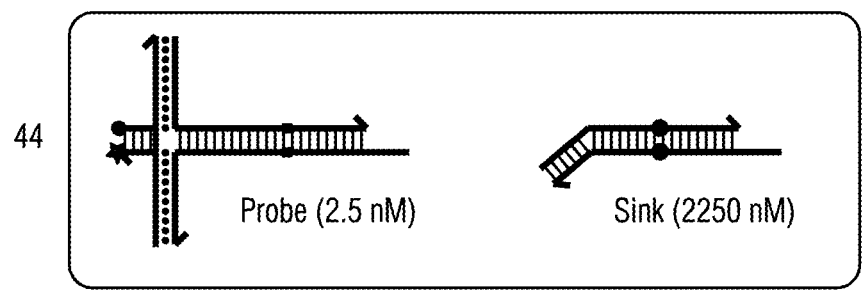
FIG. 9A provides the morphologies of the Probe and Sink used in the Competitive Composition to test 44 different cancer-related single nucleotide polymorphisms. The sequences for the probes and target/variant sequences used are shown in Tables 1-3.

Similar experiments to FIG. 6-8 were conducted for 44 different cancer-related mutations for Competitive Compositions with X=1000 using the Probe and Sink morphologies shown in FIG. 9A. Tables 1-3 below represents the sequences used in these experiments where: P—first target probe oligonucleotide; C—second target probe oligonucleotide; F—third target probe oligonucleotide with label; Q—fourth target probe oligonucleotide with quencher; $P_s$—first variant probe oligonucleotide; $C_s$—second variant probe oligonucleotide; T—target nucleic acid sequence; V—variant nucleic acid species. It should be noted that the third and fourth target probe oligonucleotides were commonly with every Probe (Probe for each experiment comprises P-C-F-Q complex with only the P-C sequences varying). The F and P functionalized strands were post-synthesis HPLC purified by IDT; all other strands were ordered with standard desalt and not purified. In functionalized sequences, /3Rox N/ denotes the IDT entry code for the 3' ROX (carboxy-X-rhodamine) fluorophore functionalized by NHS ester chemistry, and /5IAbRQ/ the IDT entry code for the 5' Iowa Black Red Quencher group.

TABLE 1

Sequences for the Probes, Sinks, Targets, and Variants used in the Experiments of FIG. 9A-9D.

| Allele | dGorxn1 | dGorxn2 | Species | SEQ ID NO. | Sequence |
|---|---|---|---|---|---|
| SMAD7-C | -1.38 | -4.33 | P | 5 | AAGGACGAGCAAATGTACCTG CACTCATCCAAAAGAGGAAA |
|  |  |  | C | 6 | GGGTCCTGTTTCCTCTTTTGGATGAGTG GTCTACTATCCACGATTTAAC |
|  |  |  | Ps | 7 | CGACTCTCATCCAAAAGAGGAA |
|  |  |  | Cs | 8 | GGGTCCTATTTCCTCTTTTGGATGAGAGTCG |

TABLE 1-continued

Sequences for the Probes, Sinks, Targets, and Variants used in the Experiments of FIG.9A-9D.

| Allele | dGorxn1 | dGorxn2 | Species | SEQ ID NO. | Sequence |
|---|---|---|---|---|---|
| SMAD7-T | -0.90 | -5.07 | P | 9 | AAGGACGAGCAAATGTACCTG CACTCATCCAAAAGAGGAA |
| | | | C | 10 | GGGTCCTATTTCCTCTTTTGGATGAGTG GTCTACTATCCACGATTTAAC |
| | | | Ps | 11 | ACACACTCATCCAAAAGAGGAAA |
| | | | Cs | 12 | GGGTCCTGTTTCCTCTTTTGGATGAGTGTGT |
| BRAF-D594G (c.1781A > G) | -0.66 | -2.35 | T | 13 | ATAGGTGGTTTTGGTCTAGCTACAGTGAAA |
| | | | V | 14 | ATAGGTGATTTTGGTCTAGCTACAGTGAAA |
| | | | P | 15 | AAGGACGAGCAAATGTACCTG CAAGGTGGTTTTGGTCTAGC |
| | | | C | 16 | TTCACTGTAGCTAGACCAAAACCACCTTG GTCTACTATCCACGATTTAAC |
| | | | Ps | 17 | TGTTAATAAGGTGATTTTGGTCTAGC |
| | | | Cs | 18 | TCACTGTAGCTAGACCAAAATCACCTTATTAACA |
| BRAF-V600E (c.1799T > A) | -1.59 | -4.29 | T | 19 | ATAGGTGATTTTGGTCTAGCTACAGAGAAA |
| | | | V | 20 | ATAGGTGATTTTGGTCTAGCTACAGTGAAA |
| | | | P | 21 | AAGGACGAGCAAATGTACCTG CAAGGTGATTTTGGTCTAG |
| | | | C | 22 | TCTCTGTAGCTAGACCAAAATCACCTTG GTCTACTATCCACGATTTAAC |
| | | | Ps | 23 | CGCAGGTGATTTTGGTCTAGC |
| | | | Cs | 24 | TCACTGTAGCTAGACCAAAATCACCTGCG |
| EGFR-G719A (c.2156G > C) | 0.35 | -5.21 | T | 25 | TTCAAAAAGATCAAAGTGCTGGCCTCCGGT |
| | | | V | 26 | TTCAAAAAGATCAAAGTGCTGGGCTCCGGT |
| | | | P | 27 | AAGGACGAGCAAATGTACCTG CACAAAAAGATCAAAGTGCTGG |
| | | | C | 28 | CGGAGGCCAGCACTTTGATCTTTTTGTG GTCTACTATCCACGATTTAAC |
| | | | Ps | 29 | AGGCAAAAAGATCAAAGTGCTGG |
| | | | Cs | 30 | CGGAGCCCAGCACTTTGATCTTTTTGCCT |
| EGFR-S768I (c.2303G > T) | -0.72 | -5.18 | T | 31 | GCCTACGTGATGGCCATCGTGGACAACCCC |
| | | | V | 32 | GCCTACGTGATGGCCAGCGTGGACAACCCC |
| | | | P | 33 | AAGGACGAGCAAATGTACCTG CACTACGTGATGGCCATCGT |
| | | | C | 34 | GGTTGTCCACGATGGCCATCACGTAGTG GTCTACTATCCACGATTTAAC |
| | | | Ps | 35 | AGTTCTACGTGATGGCCAGCGTG |
| | | | Cs | 36 | GGTTGTCCACGCTGGCCATCACGTAGAACT |
| EGFR-T790M (c.2369C > T) | -0.10 | -2.75 | T | 37 | GTGCAGCTCATCATGCAGCTCATGCCCTTC |
| | | | V | 38 | GTGCAGCTCATCACGCAGCTCATGCCCTTC |
| | | | P | 39 | AAGGACGAGCAAATGTACCTG CAGCAGCTCATCATGCAGCTC |
| | | | C | 40 | AGGGCATGAGCTGCATGATGAGCTGCTG GTCTACTATCCACGATTTAAC |
| | | | Ps | 41 | TGTTAATAGCAGCTCATCACGCAGCTC |
| | | | Cs | 42 | AGGGCATGAGCTGCGTGATGAGCTGCTATTAACA |
| EGFR-L858R (c.2573T > G) | -1.28 | -2.69 | T | 43 | ATGTCAAGATCACAGATTTTGGGCGGGCCA |
| | | | V | 44 | ATGTCAAGATCACAGATTTTGGGCTGGCCA |
| | | | P | 45 | AAGGACGAGCAAATGTACCTG CAGTCAAGATCACAGATTTTGG |
| | | | C | 46 | GCCCGCCCAAAATCTGTGATCTTGACTG GTCTACTATCCACGATTTAAC |
| | | | Ps | 47 | TGTTAATAGTCAAGATCACAGATTTTGG |
| | | | Cs | 48 | GCCAGCCCAAAATCTGTGATCTTGACTATTAACA |
| EGFR-L861Q (c.2582T > A) | -0.39 | -4.45 | T | 49 | TGGCCAAACAGCTGGGTGCGGAAGAGAAAG |
| | | | V | 50 | TGGCCAAACTGCTGGGTGCGGAAGAGAAAG |
| | | | P | 51 | AAGGACGAGCAAATGTACCTG CAGCCAAACAGCTGGGTGCG |
| | | | C | 52 | TTTCTCTTCCGCACCCAGCTGTTTGGCTG GTCTACTATCCACGATTTAAC |
| | | | Ps | 53 | TAGTTGCCAAACTGCTGGGTGCG |
| | | | Cs | 54 | TTCTCTTCCGCACCCAGCAGTTTGGCAACTA |
| ERBB2-S310F (c.929C > T) | -0.41 | -3.90 | T | 55 | ACTACCTTTCTACGGACGTGGGATTCTGCA |
| | | | | V | 56 | ACTACCTTTCTACGGACGTGGGATCCTGCA |
| | | | P | 57 | AAGGACGAGCAAATGTACCTG CATACCTTTCTACGGACGTG |

TABLE 1-continued

Sequences for the Probes, Sinks, Targets, and Variants used in the Experiments of FIG. 9A-9D.

| Allele | dGorxn1 | dGorxn2 | Species | SEQ ID NO. | Sequence |
|---|---|---|---|---|---|
| | | | C | 58 | CAGAATCCCACGTCCGTAGAAAGGTATG GTCTACTATCCACGATTTAAC |
| | | | Ps | 59 | TGTTAATATACCTTTCTACGGACGTG |
| | | | Cs | 60 | CAGGATCCCACGTCCGTAGAAAGGTATATTAACA |
| ERBB2-L755S (c.2264T > C) | -1.44 | -4.49 | T | 61 | TTCCAGTGGCCATCAAAGTGTCGAGGGAAA |
| | | | V | 62 | TTCCAGTGGCCATCAAAGTGTTGAGGGAAA |
| | | | P | 63 | AAGGACGAGCAAATGTACCTG CACCAGTGGCCATCAAAGTG |
| | | | C | 64 | TCCCTCGACACTTTGATGGCCACTGGTG GTCTACTATCCACGATTTAAC |
| | | | Ps | 65 | GTTAATACCAGTGGCCATCAAAGTG |
| | | | Cs | 66 | TCCCTCAACACTTTGATGGCCACTGGTATTAAC |
| ERBB2-V842I (c.2524G > A) | -0.84 | -4.92 | T | 67 | GGATGTGCGGCTCATACACAGGGACTTGGC |
| | | | V | 68 | GGATGTGCGGCTCGTACACAGGGACTTGGC |
| | | | P | 69 | AAGGACGAGCAAATGTACCTG CAATGTGCGGCTCATACACA |
| | | | C | 70 | CAAGTCCCTGTGTATGAGCCGCACATTG GTCTACTATCCACGATTTAAC |
| | | | Ps | 71 | GTTAATAATGTGCGGCTCGTACACA |
| | | | Cs | 72 | CAAGTCCCTGTGTACGAGCCGCACATTATTAAC |
| KRAS-G12A (c.35G > C) | -1.99 | -3.40 | T | 73 | CTTGTGGTAGTTGGAGCTGCTGGC |
| | | | V | 74 | CTTGTGGTAGTTGGAGCTGGTGGC |
| | | | P | 75 | AAGGACGAGCAAATGTACCTG CAACTTGTGGTAGTTGGAG |
| | | | C | 76 | GCCAGCAGCTCCAACTACCACAAGTTG |
| | | | Ps | 77 | CCGCTGTGGTAGTTGGA |
| | | | Cs | 78 | CACCAGCTCCAACTACCACAGCGC |
| KRAS-G12C (c.34G > T) | 1.28 | -3.40 | T | 79 | CTTGTGGTAGTTGGAGCTTGTGGC |
| | | | V | 80 | CTTGTGGTAGTTGGAGCTGGTGGC |
| | | | P | 81 | AAGGACGAGCAAATGTACCTG CAACTTGTGGTAGTTGGAGC |
| | | | C | 82 | GCCACAAGCTCCAACTACCACAAGTTG GTCTACTATCCACGATTTAAC |
| | | | Ps | 83 | CCGCTGTGGTAGTTGGA |
| | | | Cs | 84 | CACCAGCTCCAACTACCACAGCGC |
| KRAS-G12D (c.35G > A) | -0.66 | -3.77 | T | 85 | CTTGTGGTAGTTGGAGCTGATGGC |
| | | | V | 86 | CTTGTGGTAGTTGGAGCTGGTGGC |
| | | | P | 87 | AAGGACGAGCAAATGTACCTG CAACTTGTGGTAGTTGGAG |
| | | | C | 88 | GCCATCAGCTCCAACTACCACAAGTTG GTCTACTATCCACGATTTAAC |
| | | | Ps | 89 | GCATCTGTGGTAGTTGGA |
| | | | Cs | 90 | CACCAGCTCCAACTACCACAGATGC |
| KRAS-G12R (c.34G > C) | 0.26 | -3.40 | T | 91 | CTTGTGGTAGTTGGAGCTCGTGGC |
| | | | V | 92 | CTTGTGGTAGTTGGAGCTGGTGGC |
| | | | P | 93 | AAGGACGAGCAAATGTACCTG CAACTTGTGGTAGTTGGAGC |
| | | | C | 94 | GCCACGAGCTCCAACTACCACAAGTTG GTCTACTATCCACGATTTAAC |
| | | | Ps | 95 | CCGCTGTGGTAGTTGGA |
| | | | Cs | 96 | CACCAGCTCCAACTACCACAGCGC |
| KRAS-G12S (c.34G > A) | -0.34 | -3.40 | T | 97 | CTTGTGGTAGTTGGAGCTAGTGGC |
| | | | V | 98 | CTTGTGGTAGTTGGAGCTGGTGGC |
| | | | P | 99 | AAGGACGAGCAAATGTACCTG CAACTTGTGGTAGTTGGAG |
| | | | C | 100 | GCCACTAGCTCCAACTACCACAAGTTG GTCTACTATCCACGATTTAAC |
| | | | Ps | 101 | CCGCTGTGGTAGTTGGA |
| | | | Cs | 102 | CACCAGCTCCAACTACCACAGCGC |
| KRAS-G12V (c.35G > T) | -0.92 | -3.40 | T | 103 | CTTGTGGTAGTTGGAGCTGTTGGC |
| | | | V | 104 | CTTGTGGTAGTTGGAGCTGGTGGC |
| | | | P | 105 | AAGGACGAGCAAATGTACCTG CAACTTGTGGTAGTTGGAG |

TABLE 1-continued

Sequences for the Probes, Sinks, Targets, and Variants used in the Experiments of FIG.9A-9D.

| Allele | dGorxn1 | dGorxn2 | Species | SEQ ID NO. | Sequence |
|---|---|---|---|---|---|
| | | | C | 106 | GCCAACAGCTCCAACTACCACAAGTTG GTCTACTATCCACGATTTAAC |
| | | | Ps | 107 | CCGCTGTGGTAGTTGGA |
| | | | Cs | 108 | CACCAGCTCCAACTACCACAGCGC |
| KRAS-G13C (c.37G > T) | -0.92 | -2.85 | T | 109 | CTTGTGGTAGTTGGAGCTGGTTGC |
| | | | V | 110 | CTTGTGGTAGTTGGAGCTGGTGGC |
| | | | P | 111 | AAGGACGAGCAAATGTACCTG CAACTTGTGGTAGTTGGAG |
| | | | C | 112 | GCAACCAGCTCCAACTACCACAAGTTG GTCTACTATCCACGATTTAAC |
| | | | Ps | 113 | CAGGCTGTGGTAGTTGGA |
| | | | Cs | 114 | CACCAGCTCCAACTACCACAGCCTG |
| KRAS-G13D (c.38G > A) | -0.69 | -6.06 | T | 115 | CTTGTGGTAGTTGGAGCTGGTGACGTAGGC |
| | | | V | 116 | CTTGTGGTAGTTGGAGCTGGTGGCGTAGGC |
| | | | P | 117 | AAGGACGAGCAAATGTACCTG CATGTGGTAGTTGGAGCTGG |
| | | | C | 118 | CTACGTCACCAGCTCCAACTACCACATG GTCTACTATCCACGATTTAAC |
| | | | Ps | 119 | TTAATATGTGGTAGTTGGAGCTGGT |
| | | | Cs | 120 | CTACGCCACCAGCTCCAACTACCACATATTAA |
| KRAS-G13V (c.38G > T) | -0.69 | -6.32 | T | 121 | CTTGTGGTAGTTGGAGCTGGTGTCGTAGGC |
| | | | V | 122 | CTTGTGGTAGTTGGAGCTGGTGGCGTAGGC |
| | | | P | 123 | AAGGACGAGCAAATGTACCTG CATGTGGTAGTTGGAGCTGG |
| | | | C | 124 | CTACGACACCAGCTCCAACTACCACATG GTCTACTATCCACGATTTAAC |
| | | | Ps | 125 | AGGTGTGGTAGTTGGAGCTGGT |
| | | | Cs | 126 | CTACGCCACCAGCTCCAACTACCACACCT |
| KRAS-Q61H (c.183A > C) | -0.64 | -3.29 | T | 127 | GCAGGTCACGAGGAGTACAGTGCAATGAGG |
| | | | V | 128 | GCAGGTCAAGAGGAGTACAGTGCAATGAGG |
| | | | P | 129 | AAGGACGAGCAAATGTACCTG CAAGGTCACGAGGAGTACAG |
| | | | C | 130 | TCATTGCACTGTACTCCTCGTGACCTTG GTCTACTATCCACGATTTAAC |
| | | | Ps | 131 | TGTTAATAAGGTCAAGAGGAGTACAG |
| | | | Cs | 132 | TCATTGCACTGTACTCCTCTTGACCTTATTAACA |
| MAP2K1-K57N (c.171G > T) | -0.32 | -5.87 | T | 133 | ACCCAGAATCAGAAGGTGGGAGAACTGAAG |
| | | | V | 134 | ACCCAGAAGCAGAAGGTGGGAGAACTGAAG |
| | | | P | 135 | AAGGACGAGCAAATGTACCTG CACCAGAATCAGAAGGTGGG |
| | | | C | 136 | TTCAGTTCTCCCACCTTCTGATTCTGGTG GTCTACTATCCACGATTTAAC |
| | | | Ps | 137 | AGGCCAGAAGCAGAAGGTGGG |
| | | | Cs | 138 | TCAGTTCTCCCACCTTCTGCTTCTGGCCT |
| NRAS-G12C (c.34G > T) | 0.20 | -5.30 | T | 139 | GTGGTTGGAGCATGTGGTGTTGGGAAAAGC |
| | | | V | 140 | GTGGTTGGAGCAGGTGGTGTTGGGAAAAGC |
| | | | P | 141 | AAGGACGAGCAAATGTACCTG CAGGTTGGAGCATGTGGTGTT |
| | | | C | 142 | CTTTTCCCAACACCACATGCTCCAACCTG GTCTACTATCCACGATTTAAC |
| | | | Ps | 143 | AGGGGTTGGAGCAGGTGGTGT |
| | | | Cs | 144 | TTTTCCCAACACCACCTGCTCCAACCCCT |
| NRAS-G12D (c.35G > A) | 0.20 | -5.30 | T | 145 | GTGGTTGGAGCAGATGGTGTTGGGAAAAGC |
| | | | V | 146 | GTGGTTGGAGCAGGTGGTGTTGGGAAAAGC |
| | | | P | 147 | AAGGACGAGCAAATGTACCTG CAGGTTGGAGCAGATGGTGTT |
| | | | C | 148 | CTTTTCCCAACACCATCTGCTCCAACCTG GTCTACTATCCACGATTTAAC |
| | | | Ps | 149 | AGGGGTTGGAGCAGGTGGTGT |
| | | | Cs | 150 | TTTTCCCAACACCACCTGCTCCAACCCCT |
| NRAS-G12S (c.34G > A) | 0.55 | -5.24 | T | 151 | TACAAACTGGTGGTGGTTGGAGCAAGTGGT |
| | | | V | 152 | TACAAACTGGTGGTGGTTGGAGCAGGTGGT |
| | | | P | 153 | AAGGACGAGCAAATGTACCTG CTCAAACTGGTGGTGGTTGGA |
| | | | C | 154 | CACTTGCTCCAACCACCACCAGTTTGAG GTCTACTATCCACGATTTAAC |

TABLE 1-continued

Sequences for the Probes, Sinks, Targets, and Variants used in the Experiments of FIG.9A-9D.

| Allele | dGorxn1 | dGorxn2 | Species | SEQ ID NO. | Sequence |
|---|---|---|---|---|---|
| | | | Ps | 155 | CGATCAAACTGGTGGTGGTTGGA |
| | | | Cs | 156 | CACCTGCTCCAACCACCACCAGTTTGATCG |
| NRAS-G13D (c.38G > A) | 0.20 | -5.30 | T | 157 | GTGGTTGGAGCAGGTGATGTTGGGAAAAGC |
| | | | V | 158 | GTGGTTGGAGCAGGTGGTGTTGGGAAAAGC |
| | | | P | 159 | AAGGACGAGCAAATGTACCTG CAGGTTGGAGCAGGTGATGTT |
| | | | C | 160 | CTTTTCCCAACATCACCTGCTCCAACCTG GTCTACTATCCACGATTTAAC |
| | | | Ps | 161 | AGGGGTTGGAGCAGGTGGTGT |
| | | | Cs | 162 | TTTTCCCAACACCACCTGCTCCAACCCCT |
| NRAS-Q61H (c.183A > T) | -0.80 | -3.40 | T | 163 | ATACTGGATACAGCTGGACATGAAGAGTAC |
| | | | V | 164 | ATACTGGATACAGCTGGACAAGAAGAGTAC |
| | | | P | 165 | AAGGACGAGCAAATGTACCTG CAACTGGATACAGCTGGAC |
| | | | C | 166 | ACTCTTCATGTCCAGCTGTATCCAGTTG GTCTACTATCCACGATTTAAC |
| | | | Ps | 167 | TGTTAATAACTGGATACAGCTGGAC |
| | | | Cs | 168 | ACTCTTCTTGTCCAGCTGTATCCAGTTATTAACA |
| NRAS-Q61K (c.181C > A) | -0.28 | -3.40 | T | 169 | ATACTGGATACAGCTGGAAAAGAAGAGTAC |
| | | | V | 170 | ATACTGGATACAGCTGGACAAGAAGAGTAC |
| | | | P | 171 | AAGGACGAGCAAATGTACCTG CAACTGGATACAGCTGGAA |
| | | | C | 172 | ACTCTTCTTTTCCAGCTGTATCCAGTTG GTCTACTATCCACGATTTAAC |
| | | | Ps | 173 | TGTTAATAACTGGATACAGCTGGAC |
| | | | Cs | 174 | ACTCTTCTTGTCCAGCTGTATCCAGTTATTAACA |
| NRAS-Q61L (c.182A > T) | -0.89 | -4.12 | T | 175 | GGACATACTGGATACAGCTGGACTAGAAGA |
| | | | V | 176 | GGACATACTGGATACAGCTGGACAAGAAGA |
| | | | P | 177 | AAGGACGAGCAAATGTACCTG CAACATACTGGATACAGCT |
| | | | C | 178 | TTCTAGTCCAGCTGTATCCAGTATGTTG GTCTACTATCCACGATTTAAC |
| | | | Ps | 179 | GTTAATAACATACTGGATACAGCTG |
| | | | Cs | 180 | TTCTTGTCCAGCTGTATCCAGTATGTTATTAAC |
| NRAS-Q61R (c.182A > G) | -0.20 | -1.98 | T | 181 | ATACTGGATACAGCTGGACGAGAAGAGTAC |
| | | | V | 182 | ATACTGGATACAGCTGGACAAGAAGAGTAC |
| | | | P | 183 | AAGGACGAGCAAATGTACCTG CAACTGGATACAGCTGGACG |
| | | | C | 184 | TACTCTTCTCGTCCAGCTGTATCCAGTTG GTCTACTATCCACGATTTAAC |
| | | | Ps | 185 | GTGTTAATAACTGGATACAGCTGGAC |
| | | | Cs | 186 | ACTCTTCTTGTCCAGCTGTATCCAGTTATTAACAC |
| PIK3CA-E542K (c.1624G > A) | -0.52 | -4.79 | T | 187 | CTCTCTAAAATCACTGAGCAGGAGAAAGAT |
| | | | V | 188 | CTCTCTGAAATCACTGAGCAGGAGAAAGAT |
| | | | P | 189 | AAGGACGAGCAAATGTACCTG CACTCTAAAATCACTGAGCA |
| | | | C | 190 | TCTTTCTCCTGCTCAGTGATTTTAGAGTG GTCTACTATCCACGATTTAAC |
| | | | Ps | 191 | AGGCTCTGAAATCACTGAGCA |
| | | | Cs | 192 | CTTTCTCCTGCTCAGTGATTTCAGAGCCT |
| PIK3CA-E545K (c.1633G > A) | -0.36 | -5.25 | T | 193 | AGATCCTCTCTCTGAAATCACTAAGCAGGA |
| | | | V | 194 | AGATCCTCTCTCTGAAATCACTGAGCAGGA |
| | | | P | 195 | AAGGACGAGCAAATGTACCTG CAATCCTCTCTCTGAAATCAC |
| | | | C | 196 | CCTGCTTAGTGATTTCAGAGAGAGGATTG GTCTACTATCCACGATTTAAC |
| | | | Ps | 197 | TTAATAATCCTCTCTCTGAAATCAC |
| | | | Cs | 198 | CTGCTCAGTGATTTCAGAGAGAGGATTATTAA |
| PIK3CA-H1047L (c.3140A > T) | -0.81 | -3.47 | T | 199 | TGATGCACTTCATGGTGGCTGGACAACAAA |
| | | | V | 200 | TGATGCACATCATGGTGGCTGGACAACAAA |
| | | | P | 201 | AAGGACGAGCAAATGTACCTG CAATGCACTTCATGGTGGCT |
| | | | C | 202 | TGTTGTCCAGCCACCATGAAGTGCATTG GTCTACTATCCACGATTTAAC |
| | | | Ps | 203 | TGTTAATAATGCACATCATGGTGGCT |
| | | | Cs | 204 | TGTTGTCCAGCCACCATGATGTGCATTATTAACA |

TABLE 1-continued

Sequences for the Probes, Sinks, Targets, and Variants used in the Experiments of FIG. 9A-9D.

| Allele | dGorxn1 | dGorxn2 | Species | SEQ ID NO. | Sequence |
|---|---|---|---|---|---|
| PIK3CA-H1047R (c.3140A > G) | -0.81 | -2.05 | T | 205 | TGATGCACGTCATGGTGGCTGGACAACAAA |
| | | | V | 206 | TGATGCACATCATGGTGGCTGGACAACAAA |
| | | | P | 207 | AAGGACGAGCAAATGTACCTG CAATGCACGTCATGGTGGCT |
| | | | C | 208 | TGTTGTCCAGCCACCATGACGTGCATTG GTCTACTATCCACGATTTAAC |
| | | | Ps | 209 | GTGTTAATAATGCACATCATGGTGGCT |
| | | | Cs | 210 | TGTTGTCCAGCCACCATGATGTGCATTATTAACAC |
| STK11-Q37* (c.109C > T) | 1.02 | -3.70 | T | 211 | ATCGACTCCACCGAGGTCATCTACTAGCCG |
| | | | V | 212 | ATCGACTCCACCGAGGTCATCTACCAGCCG |
| | | | P | 213 | AAGGACGAGCAAATGTACCTG CACGACTCCACCGAGGTCAT |
| | | | C | 214 | GCTGGTAGATGACCTCGGTGGAGTCGTG GTCTACTATCCACGATTTAAC |
| | | | Ps | 215 | CACCACGACTCCACCGAGGTCAT |
| | | | Cs | 216 | GCTGGTAGATGACCTCGGTGGAGTCGTGGTG |
| STK11-P281L (c.842C > T) | 0.34 | -3.56 | T | 217 | ATCCCGGGCGACTGTGGCCCCCTGCTCTCT |
| | | | V | 218 | ATCCCGGGCGACTGTGGCCCCCCGCTCTCT |
| | | | P | 219 | AAGGACGAGCAAATGTACCTG CACCCGGGCGACTGTGGCCCC |
| | | | C | 220 | AGAGCAGGGGGCCACAGTCGCCCGGGTG GTCTACTATCCACGATTTAAC |
| | | | Ps | 221 | TGTTAATACCCGGGCGACTGTGGCCCC |
| | | | Cs | 222 | AGAGCGGGGGGCCACAGTCGCCCGGGTATTAACA |
| STK11-F354L (c.1062C > G) | 0.33 | -3.75 | T | 223 | AGGACCTCTTGGACATCGAGGATGACATCA |
| | | | V | 224 | AGGACCTCTTCGACATCGAGGATGACATCA |
| | | | P | 225 | AAGGACGAGCAAATGTACCTG CAGACCTCTTGGACATCGAG |
| | | | C | 226 | ATGTCATCCTCGATGTCCAAGAGGTCTG GTCTACTATCCACGATTTAAC |
| | | | Ps | 227 | GTTAATAGACCTCTTCGACATCGAG |
| | | | Cs | 228 | ATGTCATCCTCGATGTCGAAGAGGTCTATTAAC |
| TP53-R175H (c.524G > A) | 0.00 | -4.23 | T | 229 | GTTGTGAGGCACTGCCCCCACCATGAGCGC |
| | | | V | 230 | GTTGTGAGGCGCTGCCCCCACCATGAGCGC |
| | | | P | 231 | AAGGACGAGCAAATGTACCTG CATGTGAGGCACTGCCCCCAC |
| | | | C | 232 | GCTCATGGTGGGGGCAGTGCCTCACATG GTCTACTATCCACGATTTAAC |
| | | | Ps | 233 | GTCGAGGCGCTGCCCCCACCATG |
| | | | Cs | 234 | AGCGCTCATGGTGGGGGCAGCGCCTCGAC |
| TP53-R213* (c.637C > T) | -1.46 | -3.54 | T | 235 | ACTTTTTTGACATAGTGTGGTGGTGCCCTAT |
| | | | V | 236 | ACTTTTCGACATAGTGTGGTGGTGCCCTAT |
| | | | P | 237 | AAGGACGAGCAAATGTACCTG CATTTTTGACATAGTGTGGTG |
| | | | C | 238 | AGGGCACCACCACACTATGTCAAAAATG GTCTACTATCCACGATTTAAC |
| | | | Ps | 239 | AAGACAATTTTCGACATAGTGTGGTG |
| | | | Cs | 240 | AGGGCACCACCACACTATGTCGAAAATTGTCTT |
| TP53-Y220C (c.659A > G) | 0.08 | -2.92 | T | 241 | CGACATAGTGTGGTGGTGCCCTGTGAGCCG |
| | | | V | 242 | CGACATAGTGTGGTGGTGCCCTATGAGCCG |
| | | | P | 243 | AAGGACGAGCAAATGTACCTG CAACATAGTGTGGTGGTGCCC |
| | | | C | 244 | GCTCACAGGGCACCACCACACTATGTTG GTCTACTATCCACGATTTAAC |
| | | | Ps | 245 | TGTTAATAACATAGTGTGGTGGTGCC |
| | | | Cs | 246 | GCTCATAGGGCACCACCACACTATGTTATTAACA |
| TP53-R248Q (c.743G > A) | -0.38 | -6.06 | T | 247 | TTCCTGCATGGGCGGCATGAACCAGAGGCC |
| | | | V | 248 | TTCCTGCATGGGCGGCATGAACCGGAGGCC |
| | | | P | 249 | AAGGACGAGCAAATGTACCTG CACCTGCATGGGCGGCATGA |
| | | | C | 250 | CCTCTGGTTCATGCCGCCCATGCAGGTG GTCTACTATCCACGATTTAAC |
| | | | Ps | 251 | GCCCTGCATGGGCGGCATGAAC |
| | | | Cs | 252 | CCTCCGGTTCATGCCGCCCATGCAGGGC |

TABLE 1-continued

Sequences for the Probes, Sinks, Targets, and Variants used in the Experiments of FIG. 9A-9D.

| Allele | dGorxn1 | dGorxn2 | Species | SEQ ID NO. | Sequence |
|---|---|---|---|---|---|
| TP53-R248W (c.742C > T) | -0.26 | -2.91 | T | 253 | ATGAACTGGAGGCCCATCCTCACCATCATC |
| | | | V | 254 | ATGAACCGGAGGCCCATCCTCACCATCATC |
| | | | P | 255 | AAGGACGAGCAAATGTACCTG CAGAACTGGAGGCCCATCCT |
| | | | C | 256 | TGATGGTGAGGATGGGCCTCCAGTTCTG GTCTACTATCCACGATTTAAC |
| | | | Ps | 257 | TGTTAATAGAACCGGAGGCCCATCCT |
| | | | Cs | 258 | TGATGGTGAGGATGGGCCTCCGGTTCTATTAACA |
| TP53-R273C (c.817C > T) | 0.18 | -3.18 | T | 259 | ACGGAACAGCTTTGAGGTGTGTGTTTGTGC |
| | | | V | 260 | ACGGAACAGCTTTGAGGTGCGTGTTTGTGC |
| | | | P | 261 | AAGGACGAGCAAATGTACCTG CAGGAACAGCTTTGAGGTGT |
| | | | C | 262 | ACAAACACACACCTCAAAGCTGTTCCTG GTCTACTATCCACGATTTAAC |
| | | | Ps | 263 | TGTTAATAGGAACAGCTTTGAGGTGC |
| | | | Cs | 264 | ACAAACACGCACCTCAAAGCTGTTCCTATTAACA |
| TP53-R273H (c.818G > A) | -1.24 | -5.54 | T | 265 | AGGTGCATGTTTGTGCCTGTCCTGGGAGAG |
| | | | V | 266 | AGGTGCGTGTTTGTGCCTGTCCTGGGAGAG |
| | | | P | 267 | AAGGACGAGCAAATGTACCTG CAGTGCATGTTTGTGCCTGT |
| | | | C | 268 | CTCCCAGGACAGGCACAAACATGCACTG GTCTACTATCCACGATTTAAC |
| | | | Ps | 269 | AGTTGTGCGTGTTTGTGCCTGTC |
| | | | Cs | 270 | CTCCCAGGACAGGCACAAACACGCACAACT |
| TP53-R282W (c.844C > T) | 0.28 | -3.81 | T | 271 | GGGAGAGACTGGCGCACAGAGGAAGAGAAT |
| | | | V | 272 | GGGAGAGACCGGCGCACAGAGGAAGAGAAT |
| | | | P | 273 | AAGGACGAGCAAATGTACCTG CAGAGAGACTGGCGCACAGA |
| | | | C | 274 | TCTCTTCCTCTGTGCGCCAGTCTCTCTG GTCTACTATCCACGATTTAAC |
| | | | Ps | 275 | GTTAATAGAGAGACCGGCGCACAGA |
| | | | Cs | 276 | TCTCTTCCTCTGTGCGCCGGTCTCTCTATTAAC |

TABLE 2

Sequences used for the Third Oligonucleotide (F) and Fourth Oligonucleotide (Q) used with the Probe Sequences of Table 1.

| Species | SEQ ID NO. | Sequence |
|---|---|---|
| F | 1 | GTTAAATCGTGGATAGTAGAC TTCGCAC/3Rox N/ |
| Q | 2 | /5IAbRQ/GTGCGAA CAGGTACATTTGCTCGTCCTT |

TABLE 3

Sequences non-allele specific primers at SMAD7 gene locus.

| Primer | SEQ ID NO. | Sequence |
|---|---|---|
| Forward Primer | 3 | CCATGCTCACAGCCTCATC |
| Reverse Primer | 4 | TGTTTCCTGAGGAGTCTGAGG |

Figure 9C:
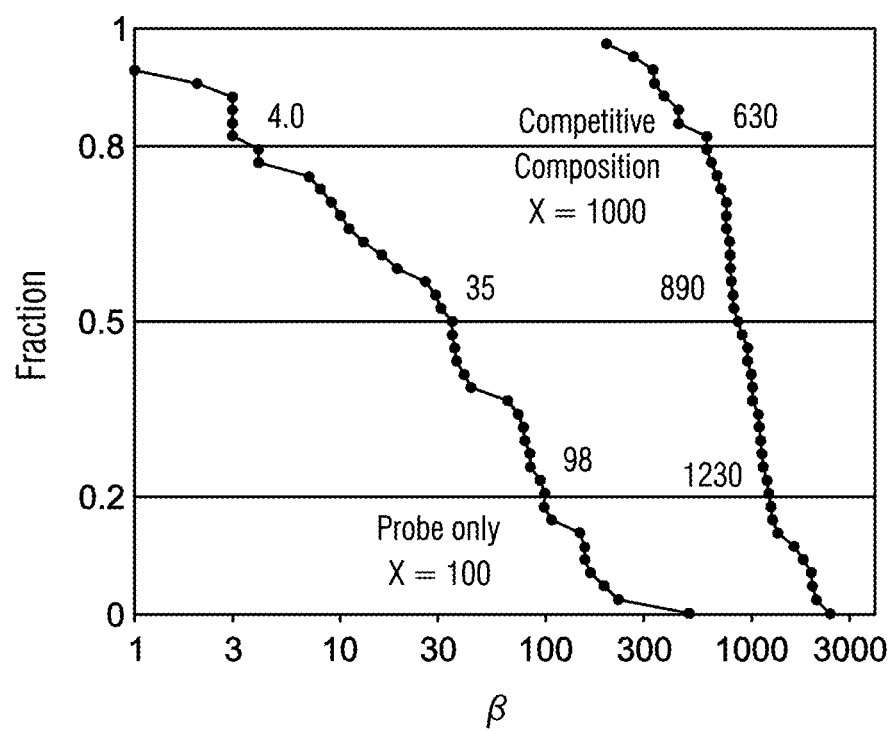
FIG. 9C provides a comparison of fold-change β from experimental results for the same 44 different Target/Variant pairs using only the Probe component of the Competitive Composition without the Sink as compared to the Competitive Composition with Probe and Sink. Here the sample Variant/Target ratio is X=100, a factor of 10 lower than for the Competitive Composition. The median fold-change β is roughly 30, consistent with the best previously reported designs. Thus, the Competitive Composition has improved enrichment by roughly a further factor of 30 to 1000, enabling rare allele detection down to 0.1% load. This is the first report of reliable enzyme-free and homogeneous detection of rare alleles at this sensitivity.
Figure 9B:
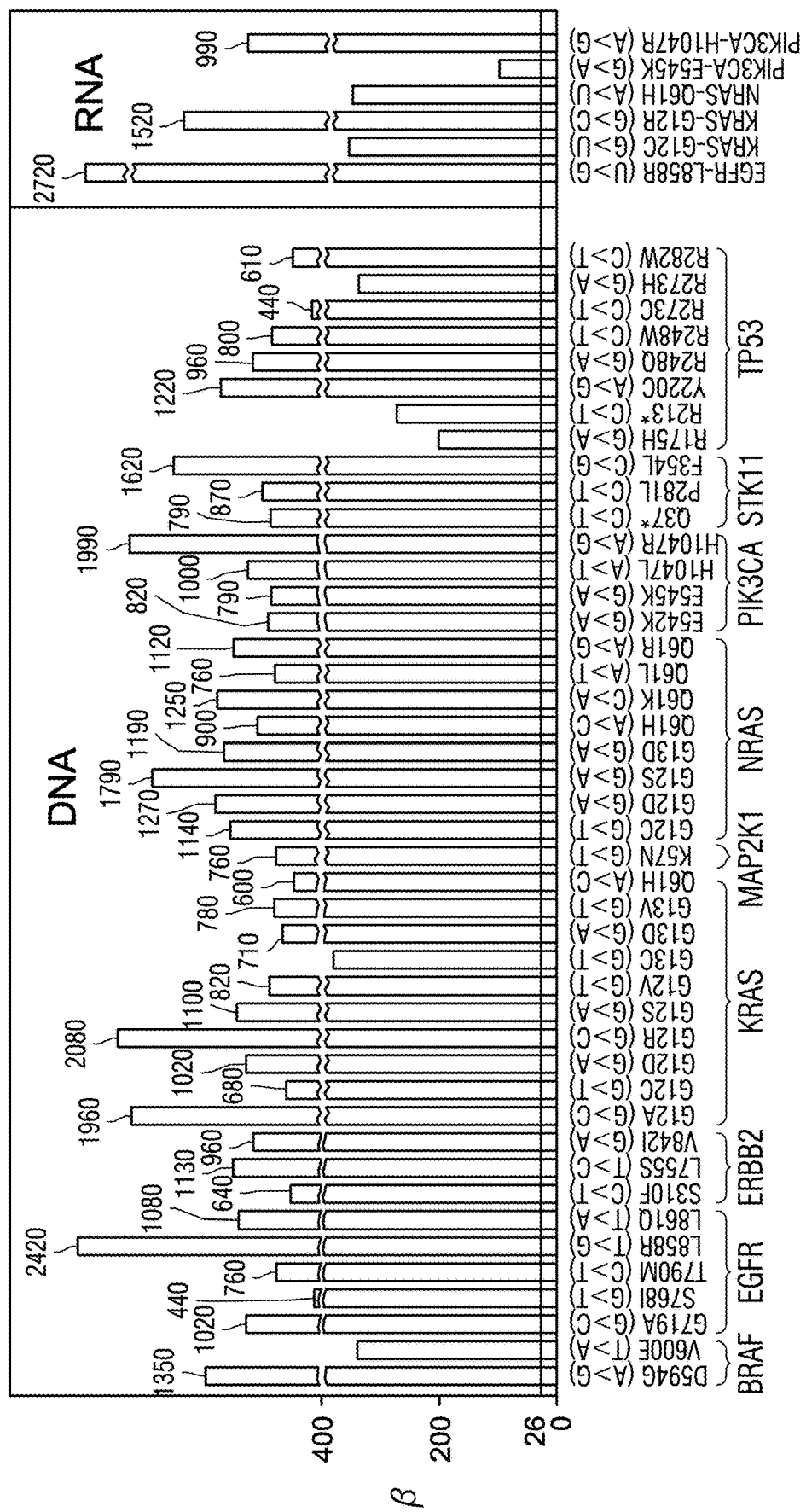
FIG. 9B provides a summary of binding affinity fold-change β from experimental results for 44 different cancer-related Target/Variant pairs using Competitive Compositions of FIG. 9A. Here the sample Variant/Target ratio is 1000:1. The binding affinity fold-change varied between 200 and 2420, with a median of roughly 1000.

The results are summarized in FIG. 9B. β values higher than 400 are showed non-linearly for clarity. As can be seen all experiments imply enrichment factors of over 200, with a median of around 1000. FIG. 9C shows comparison of Competitive Composition experiments and experiments for the same 44 different Target/Variant pairs at X=100 given just the Probe, with no Sink. Performance for Probe only experiments was highly variable, and median enrichment was significantly lower, with median of about 30, consistent with prior reports. Thus, the Competitive Composition significantly improves the enrichment of Target in a homogeneous, enzyme-free manner, facilitating applications in rare allele detection.

The primary reason for the improvement of the Competitive Composition over a good Target-specific Probe alone is that the Competitive Composition captures the enrichment power of both $\Delta\Delta G°_1$ and $\Delta\Delta G°_2$, whereas the Target-specific Probe alone captures only $\Delta\Delta G°_1$.

FIG. 10 shows Competitive Composition assays on PCR amplicons of human genomic DNA samples. Two extracted DNA samples from Coriell Cell Repository (NA18537 and NA18546) bearing single nucleotide polymorphisms at the SMAD7 gene locus are mixed at various ratios to total concentrations of 2 ng/μL (50 μL), and amplified by asymmetric non-allele-specific PCR to generate single-stranded amplicon. Competitive Compositions that are designed to each allele are mixed with the assigned PCR product for detection. As can be seen, Competitive Composition can reliably detect intended Target post PCR down to 1%.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A nucleic acid detection composition comprising:
a target nucleic acid probe comprising a first target probe oligonucleotide and a second target probe oligonucleotide, wherein the first target probe oligonucleotide comprises a target probe complement region that is complementary to a target nucleic acid sequence, wherein the second target probe oligonucleotide comprises a target probe protector region that is complementary to a first target probe complement subsequence of the target probe complement region thereby providing a target double-stranded probe portion and a target single-stranded probe portion, wherein the target double-stranded probe portion comprises the first target probe complement subsequence and the target probe protector region, and the target single-stranded probe portion comprises a second target probe complement subsequence of the target probe complement region;
a target auxiliary oligonucleotide, wherein the target auxiliary oligonucleotide is the second target probe oligonucleotide separate from the target nucleic acid probe;
a variant nucleic acid probe comprising a first variant probe oligonucleotide and a second variant probe oligonucleotide, wherein the first variant probe oligonucleotide comprises a variant probe complement region that is complementary to a variant nucleic acid sequence, wherein the second variant probe oligonucleotide comprises a variant probe protector region that is complementary to a first variant probe complement subsequence of the variant probe complement region thereby providing a variant double-stranded probe portion and a variant single-stranded probe portion, wherein the variant double-stranded probe portion comprises the first variant probe complement subsequence and the variant probe protector region, and the variant single-stranded probe portion comprises a second variant probe complement subsequence of the variant probe complement region; and
a variant auxiliary oligonucleotide, wherein the variant auxiliary oligonucleotide is the second variant oligonucleotide separate from the variant nucleic acid probe,
wherein the target probe complement region and the variant probe complement region share at least two conserved sequences separated by a non-conserved sequence,
wherein the target nucleic acid sequence and the variant nucleic acid sequence are not present on the same nucleic acid molecule,
wherein the target nucleic acid probe has a target reaction standard free energy ($\Delta G°rxn1$) with the target nucleic acid sequence, wherein the variant nucleic acid probe has a variant reaction standard free energy ($\Delta G°rxn2$) with the variant nucleic acid sequence, and wherein $\Delta G°rxn1$ is greater than $\Delta G°rxn2$.

2. The composition of claim 1 wherein the non-conserved sequence is a single nucleotide.

3. The composition of claim 1 wherein the target probe complement region and the variant probe complement region share two conserved sequences separated by a non-conserved sequence.

4. The composition of claim 3 wherein the non-conserved sequence is a single nucleotide.

5. The composition of claim 1 wherein the first target probe oligonucleotide comprises a detectable label or a capture moiety conjugated thereto.

6. The composition of claim 5 wherein the second target probe oligonucleotide comprises a signal quencher sufficient to prevent detection of the detectable label or a binding quencher sufficient to prevent capture of the capture moiety.

7. The composition of claim 1 further comprising a third target probe oligonucleotide hybridized to a target probe non-complement region of the first target probe oligonucleotide, wherein the third target probe oligonucleotide comprises a detectable label or a capture moiety conjugated thereto, and a fourth target probe oligonucleotide hybridized to a target probe non-protector region of the second target probe oligonucleotide, wherein the fourth target probe oligonucleotide comprises a signal quencher sufficient to prevent detection of the detectable label or a binding quencher sufficient to prevent capture of the capture moiety.

8. The composition of claim 1 wherein the ratio of the variant nucleic acid probe relative to the ratio of the target nucleic acid probe is from greater than 1:1 to about less than 100000:1.

9. The composition of claim 1 wherein the ratio of the target auxiliary oligonucleotide relative to the ratio of the target nucleic acid probe is from greater than 1:1000 to less than 100000:1.

10. The composition of claim 1 wherein the ratio of the variant auxiliary oligonucleotide relative to the ratio of the variant nucleic acid probe is from greater than 1:1000 to less than 100000:1.

11. The composition of claim 1 wherein $\Delta G°rxn1$ is greater than the sum of $\Delta G° rxn2 + 1$ kcal/mol.

12. The composition of claim 1 wherein the target nucleic acid probe has a concentration-adjusted target reaction standard free energy defined as $\Delta G°rxn1 + R\tau \ln([Pt]/[PtCt])$, wherein the variant nucleic acid probe has a variant reaction standard free energy defined as $\Delta G°rxn2 + R\tau \ln([Pv]/[PvCv])$, where R is the ideal gas constant, $\tau$ is the temperature in Kelvin, Pt is the initial concentration of the target auxiliary oligonucleotide, PtCt is the initial concentration of the target nucleic acid probe, Pv is the initial concentration of the variant auxiliary oligonucleotide, PvCv is the initial concentration of the variant nucleic acid probe, wherein the concentration-adjusted reaction standard free energy of the target nucleic acid probe is greater than the sum of the concentration-adjusted reaction standard free energy of the variant nucleic acid probe+1 kcal/mol.

13. The composition of claim 1 wherein $\Delta G°rxn2$ is greater than −7 kcal/mol.

14. The composition of claim 1 wherein the target nucleic acid probe further comprises a third oligonucleotide and a fourth oligonucleotide, wherein the third oligonucleotide comprises a first target probe oligonucleotide-specific subsequence and a fourth oligonucleotide specific subsequence, wherein the first target probe oligonucleotide-specific subsequence is complementary to a target probe non-complement region of the first target probe oligonucleotide, wherein the fourth oligonucleotide comprises a second target probe oligonucleotide-specific subsequence and a third oligonucleotide-specific subsequence, wherein the second target probe oligonucleotide-specific subsequence is complementary to a target probe non-protector region of the second target probe oligonucleotide, wherein the target probe non-protector region of the second target probe oligonucleotide does not overlap with the target probe protector region, wherein the fourth oligonucleotide-specific subsequence is complementary to the third oligonucleotide-specific subsequence, and wherein the target auxiliary oligonucleotide further comprises the fourth oligonucleotide.

15. The composition of claim 14 wherein the fourth oligonucleotide-specific subsequence of the third oligonucleotide comprises a detectable label or a capture moiety conjugated thereto, and wherein the third oligonucleotide-specific subsequence of the fourth oligonucleotide comprises a signal quencher sufficient to prevent detection of the detectable label or a binding quencher sufficient to prevent capture of the capture moiety.

16. The composition of claim 1 wherein the variant nucleic acid probe further comprises a third oligonucleotide and a fourth oligonucleotide, wherein the third oligonucleotide comprises a first variant probe oligonucleotide-specific subsequence and a fourth oligonucleotide specific subsequence, wherein the first variant probe oligonucleotide-specific subsequence is complementary to a variant probe non-complement region of the first variant probe oligonucleotide, wherein the fourth oligonucleotide comprises a second variant probe oligonucleotide-specific subsequence and a third oligonucleotide-specific subsequence, wherein the second variant probe oligonucleotide-specific subsequence is complementary to a variant probe non-protector region of the second variant probe oligonucleotide, wherein the variant probe non-protector region of the second variant probe oligonucleotide does not overlap with the variant probe protector region, wherein the fourth oligonucleotide-specific subsequence is complementary to the third oligonucleotide-specific subsequence, and wherein the variant auxiliary oligonucleotide further comprises the fourth oligonucleotide.

17. A nucleic acid detection composition comprising:
a target nucleic acid probe comprising a first target probe oligonucleotide and a second target probe oligonucleotide, wherein the first target probe oligonucleotide comprises a target probe complement region that is complementary to a target nucleic acid sequence, wherein the second target probe oligonucleotide comprises a target probe protector region that is complementary to a first target probe complement subsequence of the target probe complement region thereby providing a target double-stranded probe portion and a target single-stranded probe portion, wherein the target double-stranded probe portion comprises the first target probe complement subsequence and the target probe protector region, and the target single-stranded probe portion comprises a second target probe complement subsequence of the target probe complement region;
a target auxiliary oligonucleotide, wherein the target auxiliary oligonucleotide is the second target probe oligonucleotide separate from the target nucleic acid probe; and
a variant nucleic acid probe comprising a first variant probe oligonucleotide, wherein the first variant probe oligonucleotide comprises a variant probe complement region that is complementary to a variant nucleic acid sequence,
wherein the target probe complement region and the variant probe complement region share at least two conserved sequences separated by a non-conserved sequence,
wherein the target nucleic acid sequence and the variant nucleic acid sequence are not present on the same nucleic acid molecule,
wherein the target nucleic acid probe has a target reaction standard free energy ($\Delta G°rxn1$) with the target nucleic acid sequence, wherein the variant nucleic acid probe has a variant reaction standard free energy ($\Delta G° rxn2$) with the variant nucleic acid sequence, and wherein $\Delta G°rxn1$ is greater than $\Delta G° rxn2$.

18. The composition of claim 17 wherein the target nucleic acid probe further comprises a third oligonucleotide and a fourth oligonucleotide, wherein the third oligonucleotide comprises a first target probe oligonucleotide-specific subsequence and a fourth oligonucleotide specific subsequence, wherein the first target probe oligonucleotide-specific subsequence is complementary to a target probe non-complement region of the first target probe oligonucleotide, wherein the fourth oligonucleotide comprises a second target probe oligonucleotide-specific subsequence and a third oligonucleotide-specific subsequence, wherein the second target probe oligonucleotide-specific subsequence is complementary to a target probe non-protector region of the second target probe oligonucleotide, wherein the target probe non-protector region of the second target probe oligonucleotide does not overlap with the target probe protector region, wherein the fourth oligonucleotide-specific subsequence is complementary to the third oligonucleotide-specific subsequence, and wherein the target auxiliary oligonucleotide further comprises the fourth oligonucleotide.

19. A nucleic acid detection composition comprising:

a target nucleic acid probe comprising a first target probe oligonucleotide, wherein the first target probe oligonucleotide comprises a target probe complement region that is complementary to a target nucleic acid sequence;

a variant nucleic acid probe comprising a first variant probe oligonucleotide and a second variant probe oligonucleotide, wherein the first variant probe oligonucleotide comprises a variant probe complement region that is complementary to a variant nucleic acid sequence, wherein the second variant probe oligonucleotide comprises a variant probe protector region that is complementary to a first variant probe complement subsequence of the variant probe complement region thereby providing a variant double-stranded probe portion and a variant single-stranded probe portion, wherein the variant double-stranded probe portion comprises the first variant probe complement subsequence and the variant probe protector region, and the variant single-stranded probe portion comprises a second variant probe complement subsequence of the variant probe complement region; and a variant auxiliary oligonucleotide, wherein the variant auxiliary oligonucleotide is the second variant oligonucleotide separate from the variant nucleic acid probe, wherein the target probe complement region and the variant probe complement region share at least two conserved sequences separated by a non-conserved sequence, wherein the target nucleic acid sequence and the variant nucleic acid sequence are not present on the same nucleic acid molecule, wherein the target nucleic acid probe has a target reaction standard free energy ($\Delta G°rxn1$) with the target nucleic acid sequence, wherein the variant nucleic acid probe has a variant reaction standard free energy ($\Delta G°rxn2$) with the variant nucleic acid sequence, and wherein $\Delta G°rxn1$ is greater than $\Delta G°rxn2$.

20. The composition of claim 19 wherein the variant nucleic acid probe further comprises a third oligonucleotide and a fourth oligonucleotide, wherein the third oligonucleotide comprises a first variant probe oligonucleotide-specific subsequence and a fourth oligonucleotide specific subsequence, wherein the first variant probe oligonucleotide-specific subsequence is complementary to a variant probe non-complement region of the first variant probe oligonucleotide, wherein the fourth oligonucleotide comprises a second variant probe oligonucleotide-specific subsequence and a third oligonucleotide-specific subsequence, wherein the second variant probe oligonucleotide-specific subsequence is complementary to a variant probe non-protector region of the second variant probe oligonucleotide, wherein the variant probe non-protector region of the second variant probe oligonucleotide does not overlap with the variant probe protector region, wherein the fourth oligonucleotide-specific subsequence is complementary to the third oligonucleotide-specific subsequence, and wherein the variant auxiliary oligonucleotide further comprises the fourth oligonucleotide.

* * * * *